(12) United States Patent
Schneider

(10) Patent No.: US 10,743,906 B2
(45) Date of Patent: Aug. 18, 2020

(54) TISSUE-REMOVING CATHETER INCLUDING FORCE-TRANSMITTING MEMBER FOR ACTUATING A CUTTER HOUSING

(71) Applicant: Covidien LP, Mansfield, MA (US)

(72) Inventor: Lucas Schneider, Champlin, MN (US)

(*) Notice: Subject to any disclaimer, the term of this patent is extended or adjusted under 35 U.S.C. 154(b) by 490 days.

(21) Appl. No.: 15/484,530

(22) Filed: Apr. 11, 2017

(65) Prior Publication Data

US 2017/0215915 A1 Aug. 3, 2017

Related U.S. Application Data

(63) Continuation of application No. 14/101,958, filed on Dec. 10, 2013, now Pat. No. 9,636,138.

(60) Provisional application No. 61/736,182, filed on Dec. 12, 2012.

(51) Int. Cl.
*A61B 17/3207* (2006.01)
*A61B 17/00* (2006.01)

(52) U.S. Cl.
CPC .......... *A61B 17/320758* (2013.01); *A61B 17/320783* (2013.01); *A61B 2017/00685* (2013.01); *A61B 2017/320775* (2013.01); *A61B 2017/320791* (2013.01)

(58) Field of Classification Search
CPC .... A61B 17/320758; A61B 17/320783; A61B 2017/00685; A61B 2017/320775; A61B 2017/320791

See application file for complete search history.

(56) References Cited

U.S. PATENT DOCUMENTS

| | | |
|---|---|---|
| 4,290,427 A | 9/1981 | Chin |
| 4,631,052 A | 12/1986 | Kensey |
| 4,765,332 A | 8/1988 | Fischell et al. |
| 4,790,813 A | 12/1988 | Kensey |
| 4,926,858 A | 5/1990 | Gifford, III et al. |
| 4,950,277 A | 8/1990 | Farr |
| 5,026,383 A | 6/1991 | Nobles |
| 5,085,662 A | 2/1992 | Willard |
| 5,100,424 A | 3/1992 | Jang et al. |
| 5,123,904 A | 6/1992 | Shimomura et al. |
| 5,176,693 A | 1/1993 | Pannek, Jr. |
| 5,192,291 A | 3/1993 | Pannek, Jr. |
| 5,226,909 A | 7/1993 | Evans et al. |
| 5,242,460 A | 9/1993 | Klein et al. |
| 5,350,390 A | 9/1994 | Sher |
| 5,507,760 A | 4/1996 | Wynne et al. |
| 5,507,795 A | 4/1996 | Ciang et al. |
| 5,556,408 A | 9/1996 | Farhat |
| 5,569,277 A | 10/1996 | Evans et al. |
| 5,601,580 A | 2/1997 | Goldberg et al. |
| 5,620,456 A | 4/1997 | Sauer et al. |

(Continued)

*Primary Examiner* — Jing Rui Ou

(57) ABSTRACT

A tissue-removing catheter includes a cutter. The catheter also includes a longitudinal force-transmitting member extending along a catheter body and being longitudinally movable relative to the catheter body. A distal end portion of the longitudinal force-transmitting member is operatively connected to a distal longitudinal portion of a cutter housing such that distal movement of the longitudinal force-transmitting member relative to the catheter body and the cutter imparts pivoting of the distal longitudinal portion to its open position to expose the cutter.

20 Claims, 55 Drawing Sheets

(56) References Cited

U.S. PATENT DOCUMENTS

| | | |
|---|---|---|
| 5,776,156 A | 7/1998 | Shikhman |
| 5,857,982 A | 1/1999 | Milliman et al. |
| 6,053,923 A | 4/2000 | Veca et al. |
| 6,068,603 A | 5/2000 | Suziki |
| 6,110,127 A | 8/2000 | Suziki |
| 6,428,539 B1 | 8/2002 | Baxter et al. |
| 6,503,263 B2 | 1/2003 | Adams |
| RE38,018 E | 3/2003 | Anctil et al. |
| 6,579,298 B1 | 6/2003 | Bruneau et al. |
| RE38,335 E | 11/2003 | Aust et al. |
| 7,329,267 B2 | 2/2008 | Weber et al. |
| 7,344,546 B2 | 3/2008 | Wulfman et al. |
| 7,485,125 B2 | 2/2009 | Sjostrom |
| 7,520,886 B2 | 4/2009 | Surti |
| 7,635,340 B2 | 12/2009 | Vetter et al. |
| 7,699,790 B2 | 4/2010 | Simpson |
| 7,862,518 B2 | 1/2011 | Parihar |
| 7,918,803 B2 | 4/2011 | Ritchart et al. |
| 7,927,784 B2 | 4/2011 | Simpson |
| 7,951,161 B2 | 5/2011 | Bonnette et al. |
| 7,981,128 B2 | 7/2011 | To et al. |
| 8,012,164 B1 | 9/2011 | Donohoe et al. |
| 8,052,704 B2 | 11/2011 | Olson |
| 8,062,316 B2 | 11/2011 | Patel et al. |
| 8,070,762 B2 | 12/2011 | Escudero et al. |
| 2003/0120295 A1 | 6/2003 | Simpson |
| 2003/0125757 A1* | 7/2003 | Patel ............... A61B 17/320758 606/159 |
| 2004/0006358 A1 | 1/2004 | Wulfman et al. |
| 2007/0055259 A1 | 3/2007 | Norton et al. |
| 2007/0265647 A1 | 11/2007 | Bonnette |
| 2007/0276419 A1 | 11/2007 | Rosenthal |
| 2007/0282358 A1 | 12/2007 | Remiszewski et al. |
| 2008/0004646 A1 | 1/2008 | To |
| 2008/0045986 A1 | 2/2008 | To et al. |
| 2008/0065124 A1 | 3/2008 | Olson |
| 2008/0065125 A1 | 3/2008 | Olson |
| 2008/0140104 A1 | 6/2008 | Bender et al. |
| 2010/0198240 A1 | 8/2010 | Simpson et al. |
| 2010/0280316 A1 | 11/2010 | Dietz |
| 2011/0004107 A1 | 1/2011 | Rosenthal et al. |
| 2011/0087258 A1 | 4/2011 | Sluss |
| 2011/0130777 A1 | 6/2011 | Zhang et al. |
| 2011/0144673 A1 | 6/2011 | Zhang et al. |
| 2011/0152906 A1 | 6/2011 | Escudero et al. |
| 2011/0190801 A1 | 8/2011 | Mark et al. |
| 2011/0301626 A1 | 12/2011 | To et al. |
| 2011/0306995 A1 | 12/2011 | Moberg |
| 2012/0046679 A1* | 2/2012 | Patel ................. A61B 1/00179 606/159 |
| 2013/0096589 A1 | 4/2013 | Spencer |

\* cited by examiner

TISSUE-REMOVING CATHETER INCLUDING FORCE-TRANSMITTING MEMBER FOR ACTUATING A CUTTER HOUSING

CROSS-REFERENCE TO RELATED APPLICATIONS

The present application is a continuation of U.S. patent Ser. No. 14/101,958, filed Dec. 10, 2013, now U.S. Pat. No. 9,636,138, which claims priority to U.S. Provisional Application Ser. No. 61/736,182, filed Dec. 12, 2012, the entirety of each of which is hereby incorporated by reference.

FIELD OF THE DISCLOSURE

The present invention generally relates to a tissue-removing catheter for removing tissue from a body lumen including a force-transmitting member for actuating a cutter housing.

BACKGROUND OF THE DISCLOSURE

Vascular disease frequently arises from the accumulation of atheromatous material on the inner walls of vascular lumens, particularly arterial lumens of the peripheral and other vasculature, especially peripheral arteries, resulting in a condition known as atherosclerosis. Atherosclerosis occurs naturally as a result of aging but may also be aggravated by factors such as diet, hypertension, heredity, vascular injury, and the like. Atheromatous deposits can have widely varying properties, with some deposits being relatively soft and others being fibrous and/or calcified. In the latter case, the deposits are frequently referred to as plaque.

Vascular disease can be treated in a variety of ways, including drugs, bypass surgery, and a variety of catheter-based approaches, including those which rely on intravascular debulking or removal of the atheromatous or other material occluding a blood vessel. A variety of methods for cutting or dislodging material and removing such material from the blood vessel have been proposed, generally being referred to as atherectomy procedures. Atherectomy catheters intended to cut or excise material from the blood vessel lumen may employ a rotatable cutting blade (or other tissue-removing element) which can be advanced into or past the occlusive material in order to cut and separate such material from the blood vessel lumen.

It is desirous to provide catheters which can access small, tortuous regions of body lumens and which can remove tissue and/or other occluding materials from within body lumens in a controlled fashion. In one instance, it may be desired to provide atherectomy catheters which can facilitate capturing atheromatous materials. The catheters and methods for use in a variety of body lumens, including but not limited to coronary, peripheral, and other arteries, and other body lumens.

SUMMARY OF THE DISCLOSURE

The present disclosure is directed to a tissue-removing catheter including a cutter. In one aspect, the catheter includes a longitudinal force-transmitting member extending along a catheter body and being longitudinally movable relative to the catheter body. A distal end portion of the longitudinal force-transmitting member is operatively connected to a distal longitudinal portion of a cutter housing such that distal movement of the longitudinal force-transmitting member relative to the catheter body and the cutter imparts pivoting of the distal longitudinal portion to its open position to expose the cutting edge of the cutter.

In another aspect, the catheter includes a torque-transmitting member extending along the catheter body and being rotatable relative to the catheter body. A distal end portion of the torque-transmitting member is operatively connected to the distal longitudinal portion of the cutter housing such that rotation of the torque-transmitting member about a longitudinal axis relative to the catheter body and the cutter imparts rotation of the distal longitudinal portion to its open position to expose the cutting edge of the cutter.

In yet another aspect, the catheter includes an expandable member connected to the cutter housing. The expandable member is configured such that selective expansion of the expandable member from a contracted state to an expanded state imparts pivoting of the distal longitudinal portion of the cutter housing about a hinge axis to its closed position.

In another aspect, the catheter includes an electrical conductor electrically connected to the hinge portion and extending along the catheter body. The electrical conductor is configured to supply electrical current from a power source to the hinge portion to heat the hinge portion, wherein heating of the hinge portion activates heat-activating, shape-memory material and imparts pivoting of the distal longitudinal portion about a hinge axis to one of the open and closed positions.

Yet another aspect is directed to a tissue director of the catheter that is distal of the cutter and configured to direct tissue removed by the cutter proximally through an axial cavity of the cutter.

Other features will be in part apparent and in part pointed out hereinafter.

BRIEF DESCRIPTION OF THE DRAWINGS

Corresponding reference characters indicate corresponding parts throughout the drawings.

Corresponding reference characters indicate corresponding parts throughout the drawings.

DETAILED DESCRIPTION OF THE DRAWINGS

Figure 1:
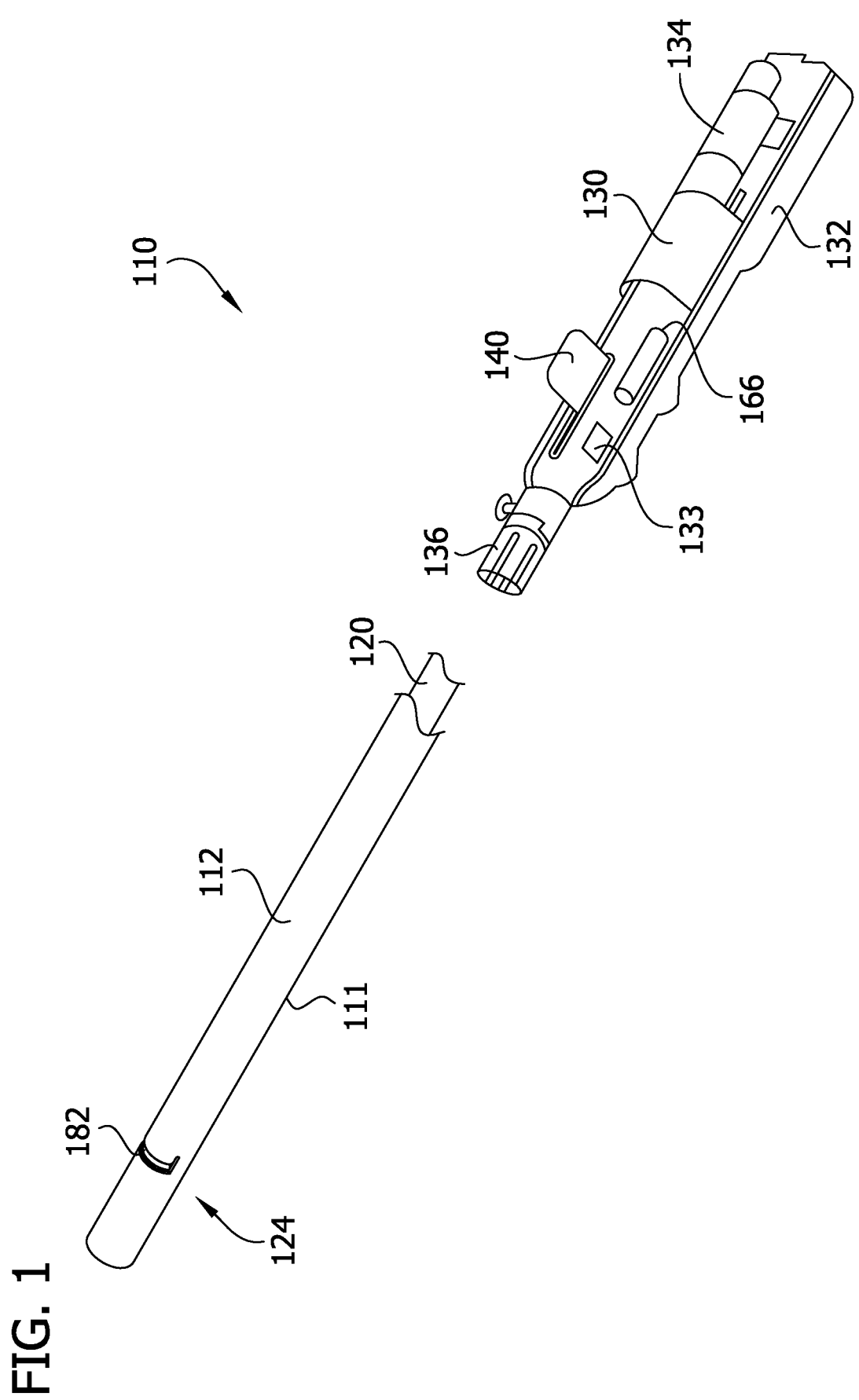
FIG. 1 is a fragmentary perspective of a first embodiment of a tissue-removing catheter.

Referring now to the drawings, several embodiments of a tissue-removing catheter for removing tissue from a body lumen are disclosed. In particular, the illustrated catheter embodiments are suitable for removing tissue from a body lumen, and are particularly suitable for removing (i.e., excising) plaque tissue from a blood vessel (e.g., peripheral arterial or peripheral venous wall). Features of the disclosed embodiments, however, may also be suitable for treating chronic total occlusion (CTO) of blood vessels, particularly peripheral arteries, and stenoses of other body lumens and other hyperplastic and neoplastic conditions in other body lumens, such as the ureter, the billary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from and penetrating occlusions in blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Referring now to FIGS. 1-12, a first embodiment of a tissue-removing catheter for removing tissue from a body lumen is generally indicated at 110. Briefly, the tissue-removing catheter 110 includes an elongate tubular catheter body 112 having opposite proximal and distal ends, a central longitudinal axis $LA_2$ (FIG. 4) extending between the distal and proximal ends. A rotatable cutter, generally indicated at 116, is operatively connected adjacent the distal end of the catheter body 112 for removing tissue from body lumen. In particular, in the illustrated embodiment the cutter 116 is operatively connected to a cutter housing generally indicated at 118, which is received in the catheter body 112 and forms part of a deployment mechanism, generally indicated at 124, as explained below. The catheter 110 also includes a hollow cutter driveshaft 120 (FIGS. 3 and 5), which drives rotation of the cutter 116, and a separate screw conveyor, generally indicated at 122 (also known as an auger conveyor), which transports or moves removed tissue proximally within the catheter body 112. The cutter driveshaft 120 defines an internal, tissue-transport passage 123 through which a screw blade 125 (or flighting) of the screw conveyor extends and through which the removed tissue is transported proximally.

Referring still to FIG. 1, the catheter body 112 is configured (e.g., sized and shaped) for intravascular introduction into the target artery, although as explained above, the catheter body may be configured for intraluminal introduction into other target body lumens other than a target artery. The catheter body 112 includes an outer polymer jacket 111 (e.g., an overmold) that is disposed along at least a longitudinal portion of the catheter 110. In the illustrated embodiment, the jacket 111 defines a guidewire channel 111a adjacent the distal end portion of the catheter body 112 that is configured for introduction of the catheter body 112 over a guidewire to a target site within the vasculature. In particular, the catheter 110 is configured for "rapid exchange" introduction because the guidewire channel 111a extends only through a distal portion of the catheter body, although the catheter may be configured for "over-the-wire" introduction where the guidewire channel extends fully through the catheter body 112. In other cases, it may be possible to provide a fixed or integral coil tip or guidewire tip on the distal portion of the catheter 110 or even dispense with the guidewire entirely. Moreover, a flexible distal tip (not shown) may be secured to the distal end of the illustrated catheter to facilitate insertion of the catheter. For convenience of illustration, guidewires will not be shown in any embodiment, but it should be appreciated that they can be incorporated into any of these embodiments.

The dimensions and other physical characteristics of the catheter body 112 may vary depending on the artery (or other body lumen) of the subject which is to be accessed. The catheter body 112 is generally flexible and may in one embodiment have a length in the range from 50 cm to 200 cm and an outer diameter in the range from 1 French to 12 French (0.33 mm:1 French), such as from 3 French to 9 French. The catheter body 112 (e.g., the jacket 111) may be composed of an organic polymer which is fabricated by extrusion techniques. Suitable polymers, such as for the jacket 111, include polyvinylchloride, polyurethanes, polyesters, polytetrafluoroethylenes (PTFE), silicone rubbers, natural rubbers, and the like. Optionally, the catheter body 112 may be reinforced with a braid, helical wires, coils, axial filaments, or the like, in order to increase rotational strength, column strength, toughness, pushability, and the like. For example, the catheter body 112 may include a torque tube, as is generally known in the art. The outer diameter of the catheter body 112 can be modified by heat expansion and shrinkage using conventional techniques. It will be appreciated that the construction and dimensions of the catheter body may be other than described without departing from the scope of the present invention.

The catheter body 112 of the present embodiment may include an urging mechanism (not shown) to urge the cutter into engagement with the body lumen wall (e.g., blood vessel wall) during treatment. For example, the urging mechanism may comprise a portion of the catheter body adjacent to and proximal of the cutter that is biased to (e.g., permanently deformed in) a double-bent or double-curved shape to urge the cutter toward a wall of a body lumen to enhance treatment. A suitable urging mechanism is disclosed in U.S. Pat. No. 7,708,749, the entirety of which is hereby incorporated by reference. In other embodiments, the urging mechanism may take many other suitable forms. The catheter may have no urging mechanism without departing from the scope of the present invention.

Figure 12:
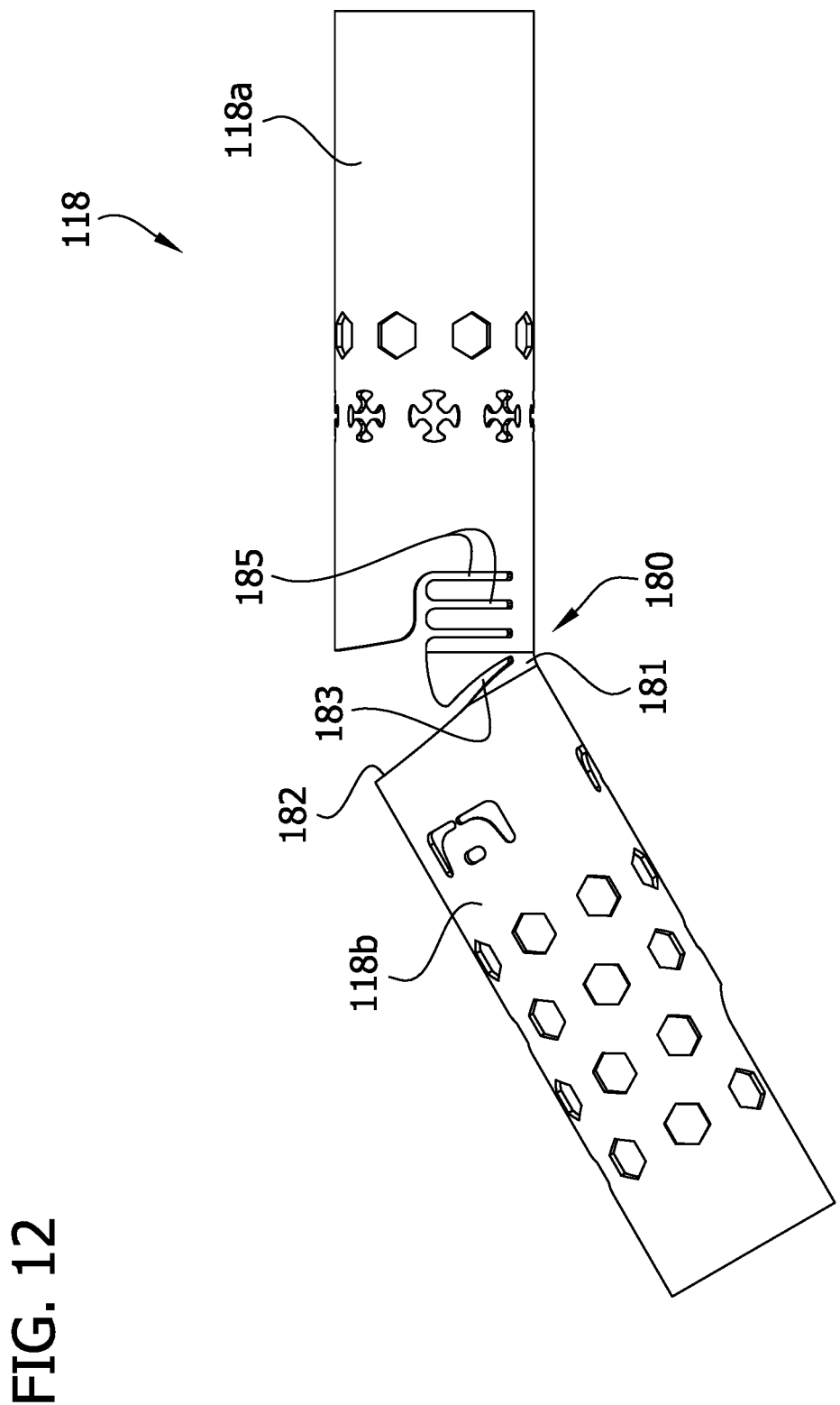
FIG. 12 is a side elevation of the cutter housing of FIG. 11.
Figure 14:
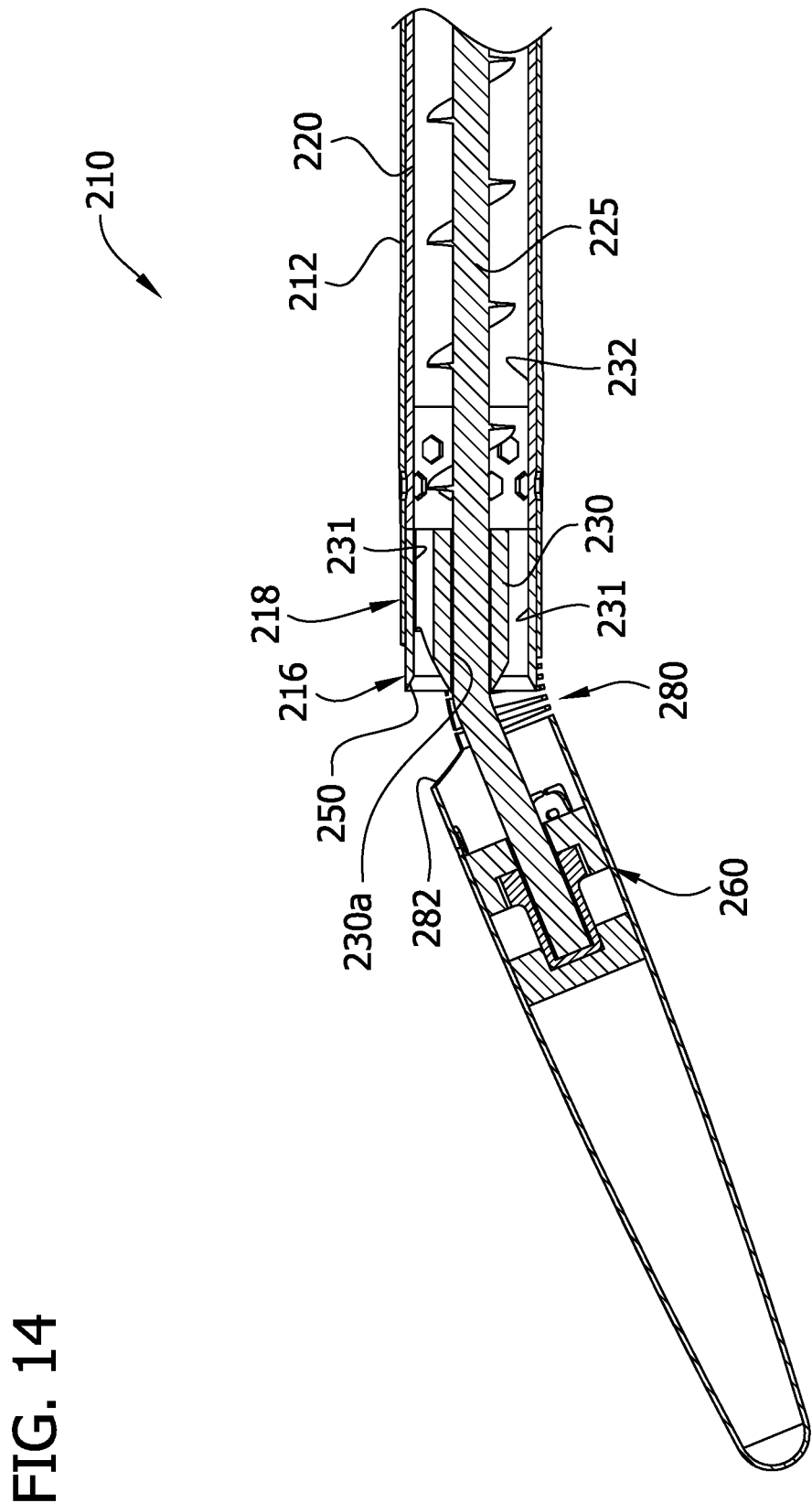
FIG. 14 is similar to FIG. 13, but with the cutter housing being in an open position.
Figure 15:
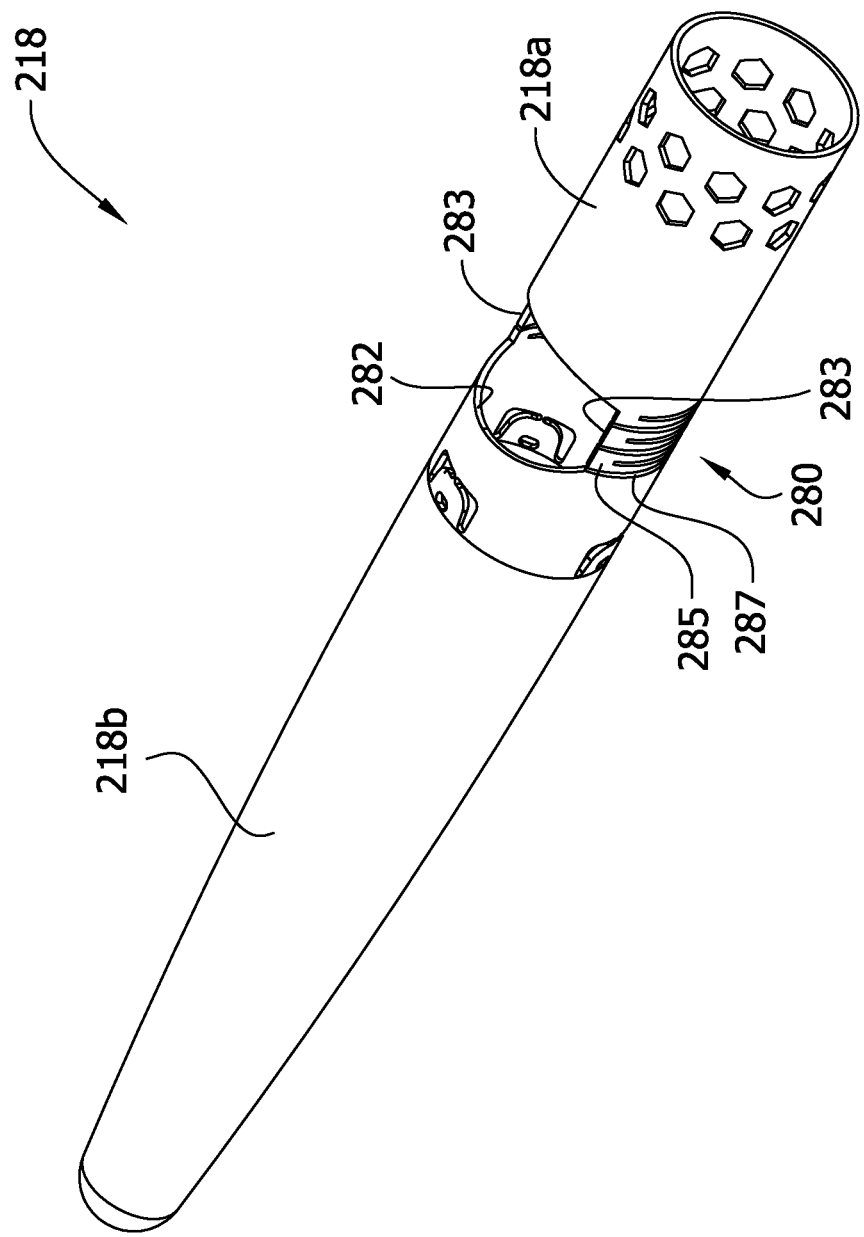
FIG. 15 is an enlarged perspective of the cutter housing.
Figure 16:
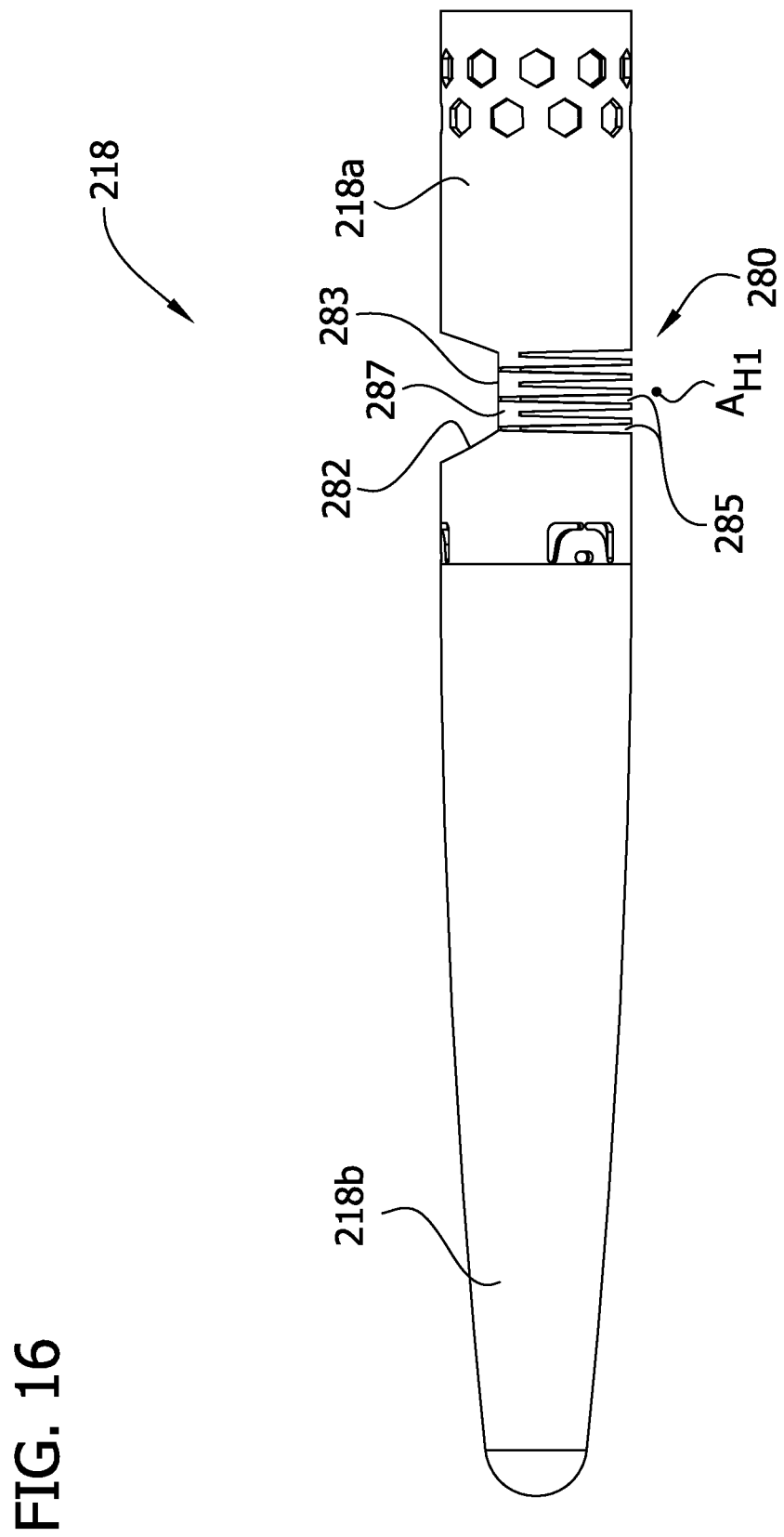
FIG. 16 is a side elevational view of the cutter housing of FIG. 15.
Figure 17:
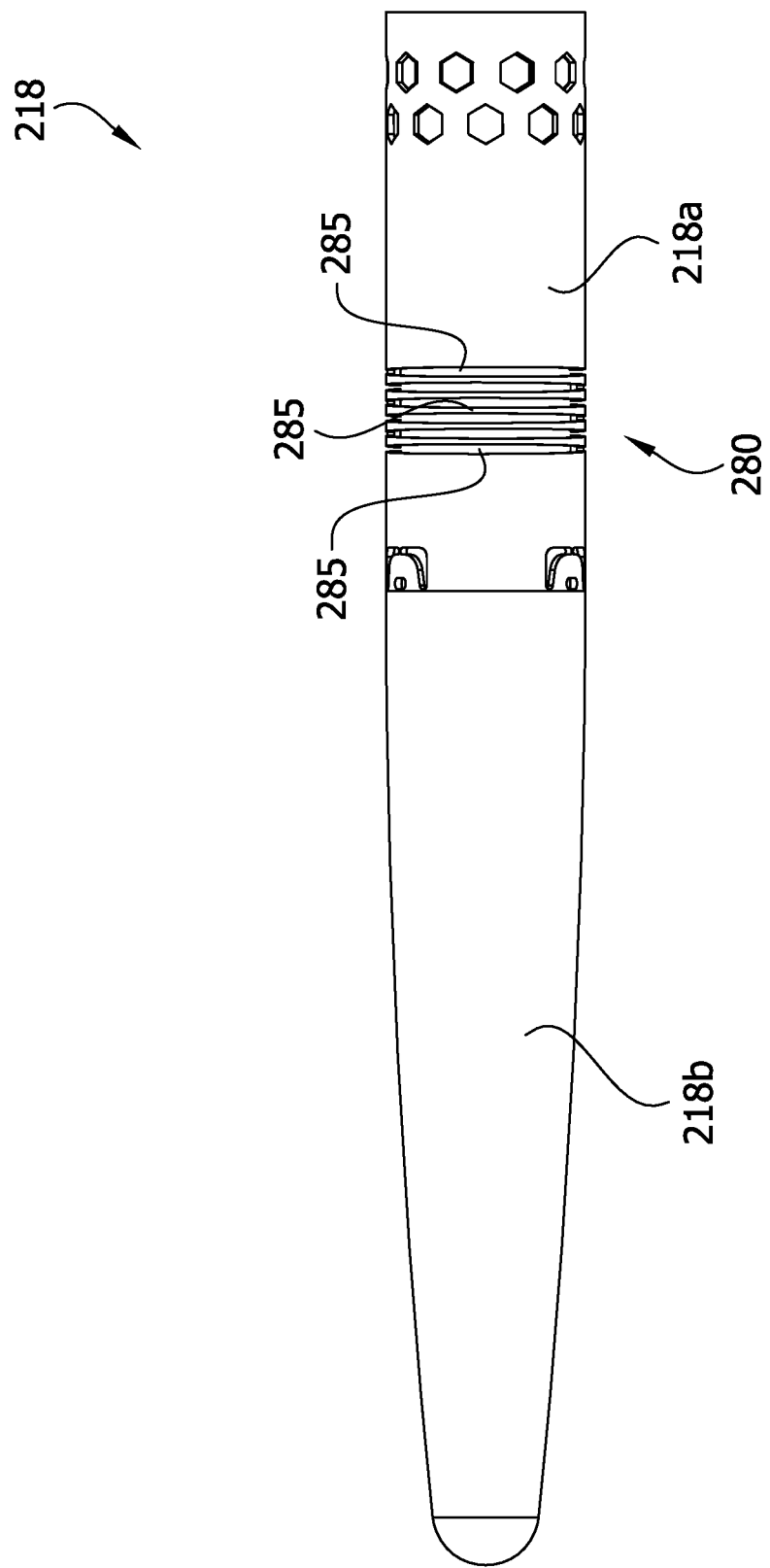
FIG. 17 is a bottom plan view of the cutter housing of FIG. 15.
Figure 18:
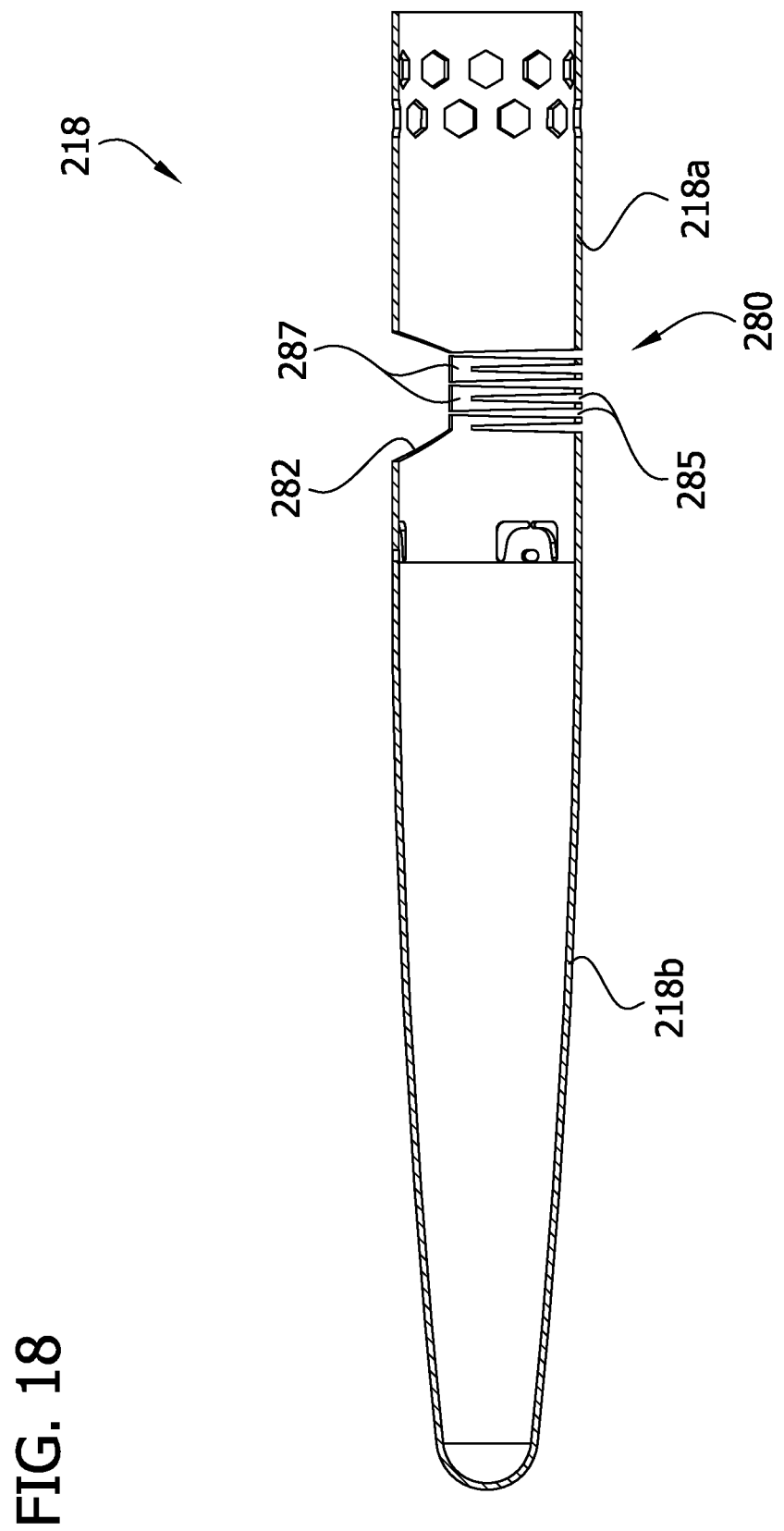
FIG. 18 is a longitudinal section of the cutter housing of FIG. 15.

Referring to FIGS. 12 and 14, as set forth above, the catheter 110 includes the rotatable cutter 116 and the driveshaft 120 for imparting rotation of the cutter. The driveshaft 120 extends along a longitudinal passage 126 in the catheter body 112 such that the driveshaft is generally coaxial with the catheter body. As explained below, in the illustrated embodiment the driveshaft 120 is rotatable about its axis independent of the screw blade 125, and the screw blade is rotatable about its axis independent of the driveshaft. A distal end portion of the driveshaft 120 is operatively connected to the rotatable cutter 116 for selectively driving rotation of the cutter generally about the longitudinal axis $LA_1$ of the catheter body 112. The shank of the driveshaft 120 is generally flexible and may be formed from one or more coils (e.g., stainless steel coil(s)), or a torque tube (e.g., a polyimide tube with a layer of braided stainless steel wire embedded therein). The shank of the driveshaft 120 may have a very high torsional stiffness and sufficient tensile strength, but which is generally laterally flexible. Depending upon the desired torque transmission, diameter and flexibility, any of a variety of other materials and constructions may also be used.

Referring to FIG. 1, the proximal end of the driveshaft 120 is operably connected to a cutter motor 130 (broadly, a cutter driver) to impart rotation of the driveshaft 120 relative to catheter body 112. In one example, the cutter motor 130 is disposed within a handle 132 (shown with a cover removed in FIG. 1) that is releasably connectable to the proximal end of the catheter 110. For example, in addition to the cutter motor 130, the handle 132 may house a power source 134 (e.g., batteries) for the cutter motor 130, a microswitch (not shown) for activating cutter motor, and a catheter connector 136 for use in connecting the motor to the proximal end portion of the driveshaft 120. In some embodiments, the cutter motor 130 can rotate the driveshaft 120 between 1,000 rpm and 10,000 rpm or more, if desired. As explained in more detail below, the handle 132 may include one or more input devices, such as actuator 133 (e.g., a switch or button), which is used to turn on (and turn off) the cutter driver 130 to selectively impart rotation of the driveshaft 120 and the cutter 116. It is understood that the driveshaft 120 may be driven in other ways without departing from the scope of the present invention.

Figure 5:
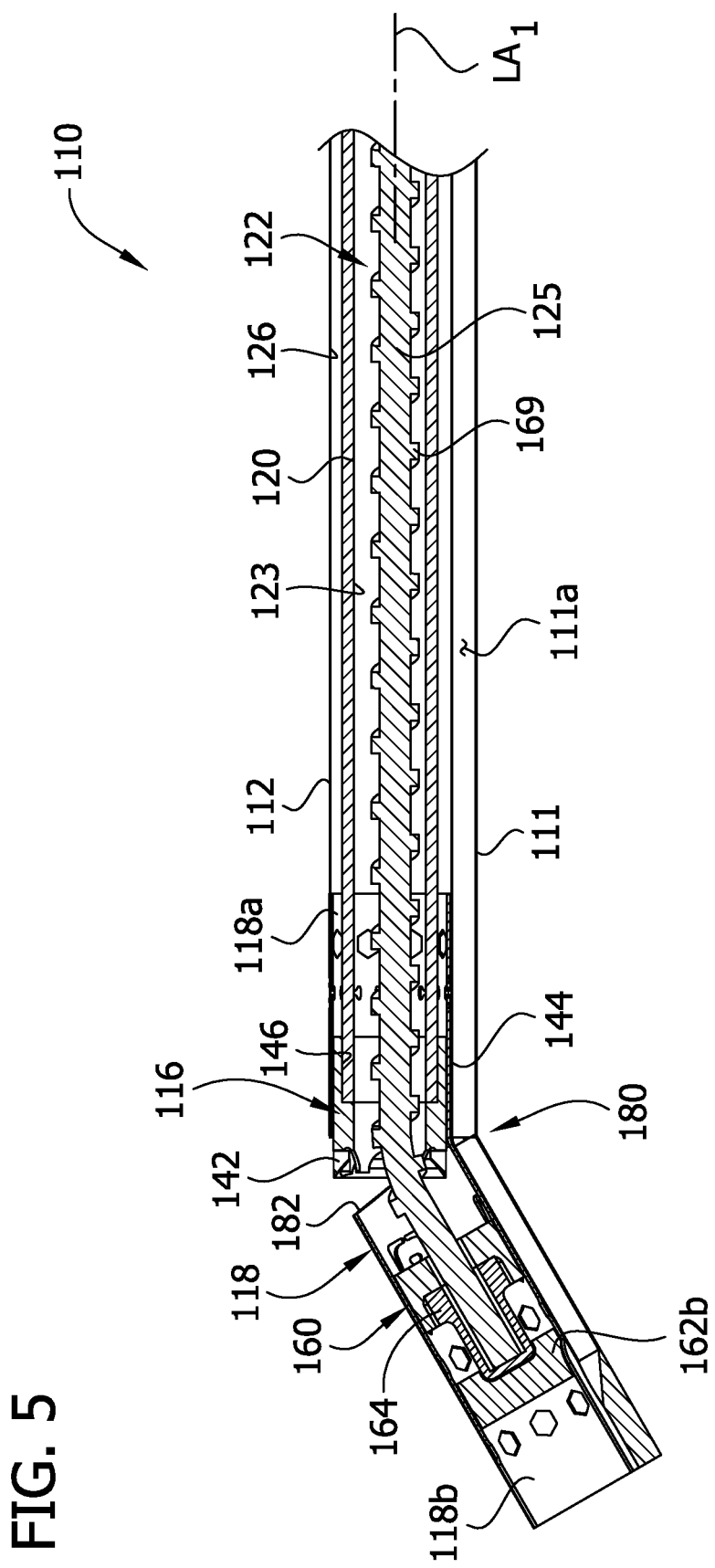
FIG. 5 is a longitudinal section of the distal end portion of the tissue-removing catheter of FIG. 4.
Figure 7:
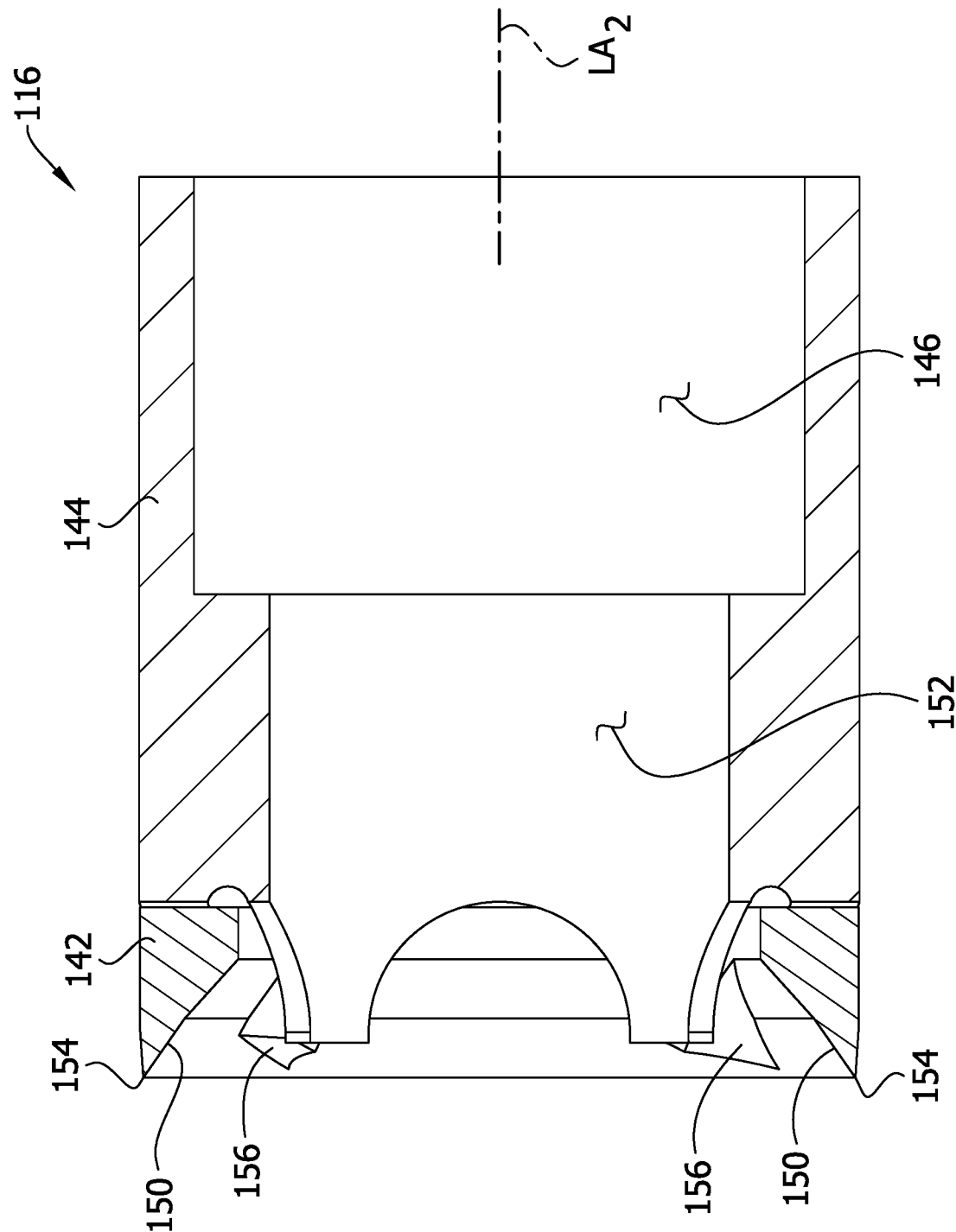
FIG. 7 is an enlarged, longitudinal section of the cutter of FIG. 6.

As seen best in FIGS. 5 and 7, the rotatable cutter 116 has opposite proximal and distal ends and a longitudinal axis $LA_2$ (FIG. 7) extending therebetween. The cutter 116 has a generally cylindrical distal cutting portion 142 and a proximal stem 144 (broadly, a driveshaft-connection portion). The cutter 116 is fixed axially within the cutter housing 118. For example, the cutter housing 118 may function as a rotary bearing for supporting the cutter 116 while allowing the cutter to rotate within the cutter housing. The cutter 116 may be formed as a single, one-piece construction, or may be formed from separate components secured to one another in a suitable manner, such as welding, soldering, adhesives, mechanical interference fit, threaded engagement and the like. As a non-limiting example, the cutter 116 may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, electro-discharge machining (EDM), laser cutting, heat treating, precipitation hardening, casting or other methods.

Figure 6:
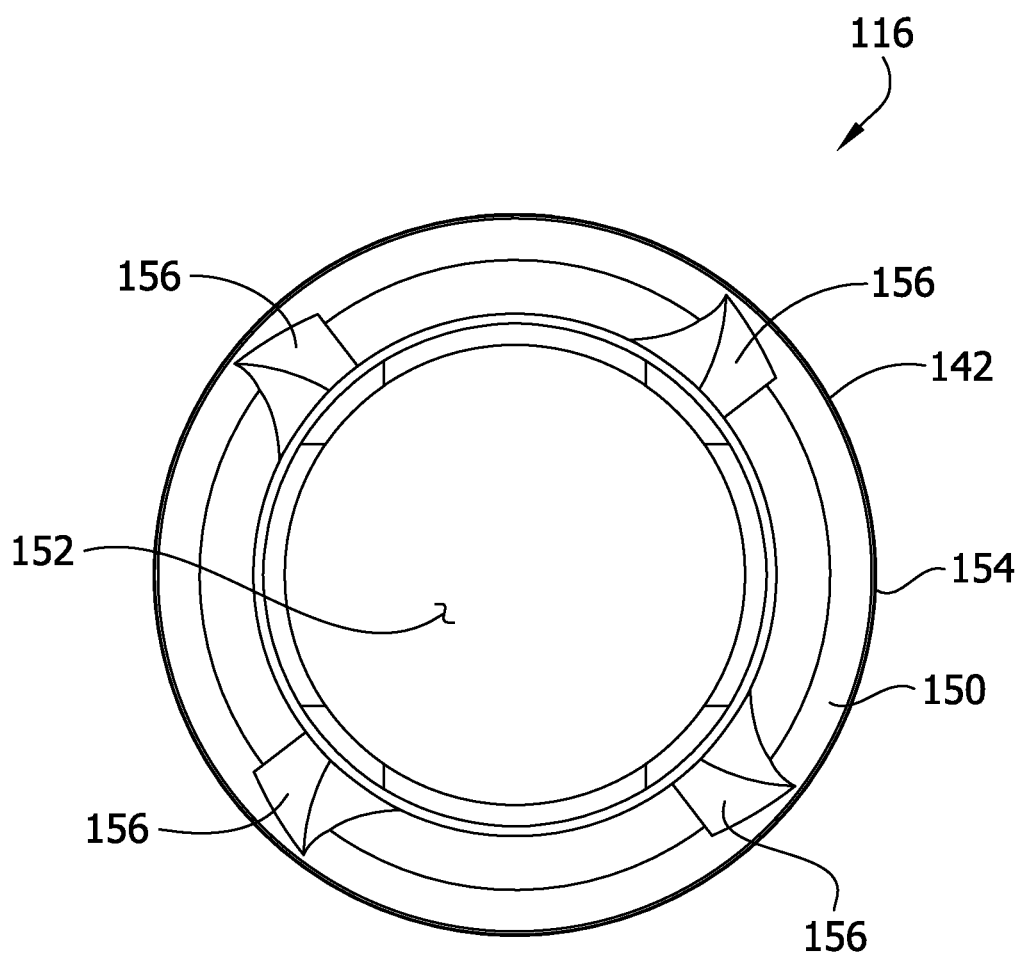
FIG. 6 is an enlarged, front elevation of a cutter of the tissue-removing catheter.

Referring still to FIGS. 6 and 7, the distal cutting portion 142 of the cutter 116 includes an annular cutting edge 150 at the distal end thereof, and an axial, through cavity 152, defined by an interior surface of the cutter 116, extending from the cutting edge through the stem 144 of the cutter. In one non-limiting example, the annular cutting edge 150 is beveled from an exterior surface of the cutter toward the interior surface to define a sharp, distal cutting edge 154. The cutting edge 150 may be formed separately from the distal cutting portion 142 of cutter 116 and attached thereto, or the cutting edge may be formed integrally with the distal cutting portion of cutter. In the embodiment illustrated, shown best in FIG. 6, the beveled, annular cutting edge 150 includes one or more raised elements 156 (e.g., breakers), although the cutting cutter 116 may have no raised elements without departing from the scope of the present invention. In the illustrated embodiment, four raised elements 156 are formed on the beveled, annular cutting edge 150, although in other embodiments more than four or fewer than four raised elements may be present. During removal of tissue from the target body lumen, the raised elements 156 produce a hammer-like impact against the tissue to be removed as the cutter 116 is rotated. In the case where the tissue to be removed has brittle characteristics (e.g., has become calcified), the tissue will be crushed into smaller particles thereby facilitating its removal. Repeated rotation of cutter 116 will produce repeated hammer-like blows of the cutter raised elements 156 against the tissue to be removed. Exemplary raised elements 156 are disclosed in U.S. Published Patent Application No. 2011/0130777 (Ser. No. 12/958,488), filed Dec. 2, 2010, the entirety of which relating to the raised elements disclosed thereon are incorporated by reference herein. In other embodiments, the annular cutting edge 150 may have a generally smooth surface. The cutting edge may be of other configurations without departing from the scope of the present invention.

The stem 144 connects the cutter 116 to the distal end of the driveshaft 120 such that rotation of the driveshaft imparts rotation of the cutter 116 about its longitudinal axis $LA_2$ (i.e., the rotational axis of the cutter is coincident with the central longitudinal axis of the cutter). In the illustrated embodiment, the distal end of the driveshaft 120 is received in an axial cavity 146 in the stem 144 and is secured therein, such as by soldering, welding, or in other ways. The axial cavity 152 defined by the cutter 116 extends generally axially through the proximal end of the cutter 116 and is in communication with the tissue-transport passage 123 defined by the driveshaft 120 so that tissue removed by the cutter passes through the axial cavity and into the tissue-transport passage, where it is picked up and transported proximally by the screw blade 125, as explained in more detail below.

Figure 2:
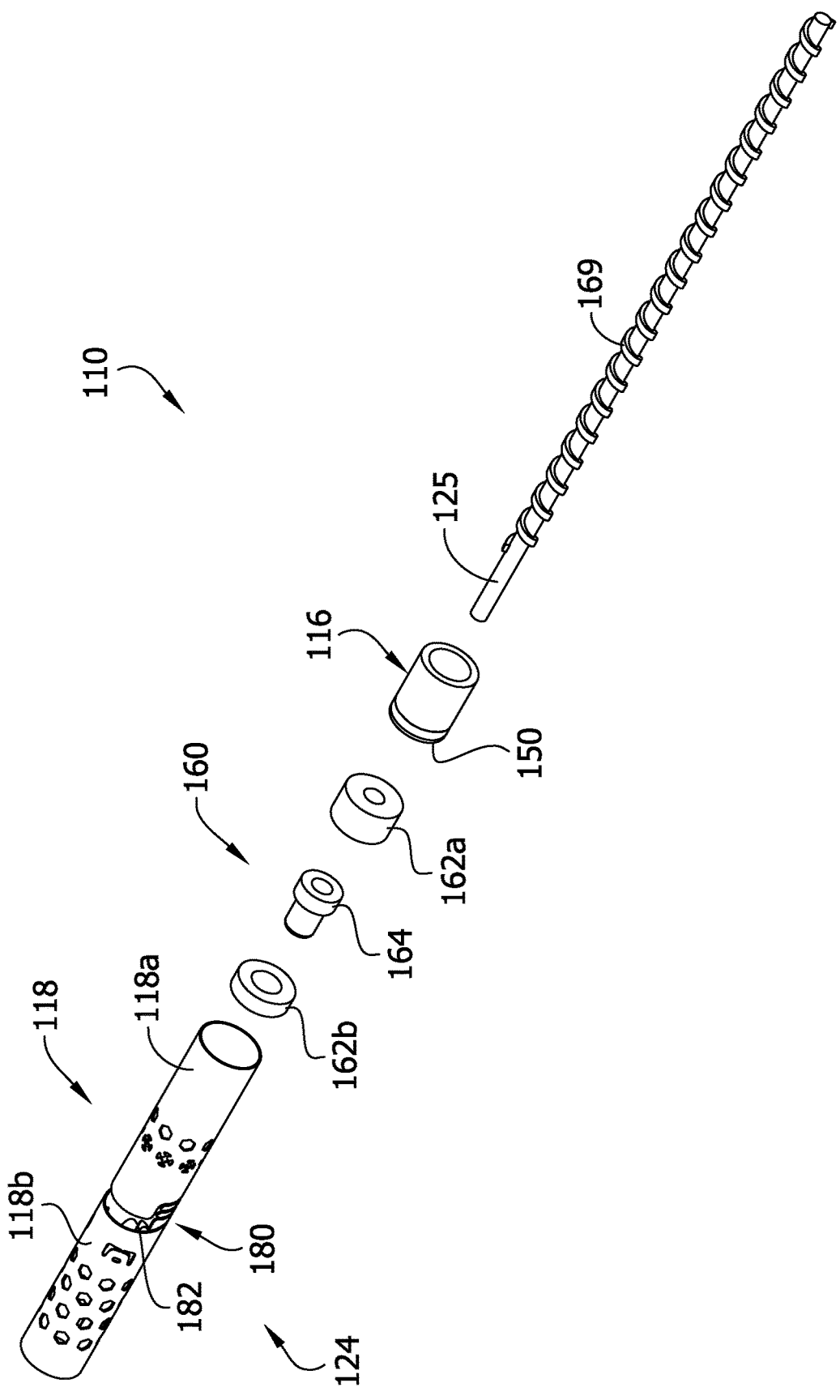
FIG. 2 is an enlarged exploded perspective of distal end portion of the tissue-removing catheter, with a polymer jacket removed.
Figure 3:
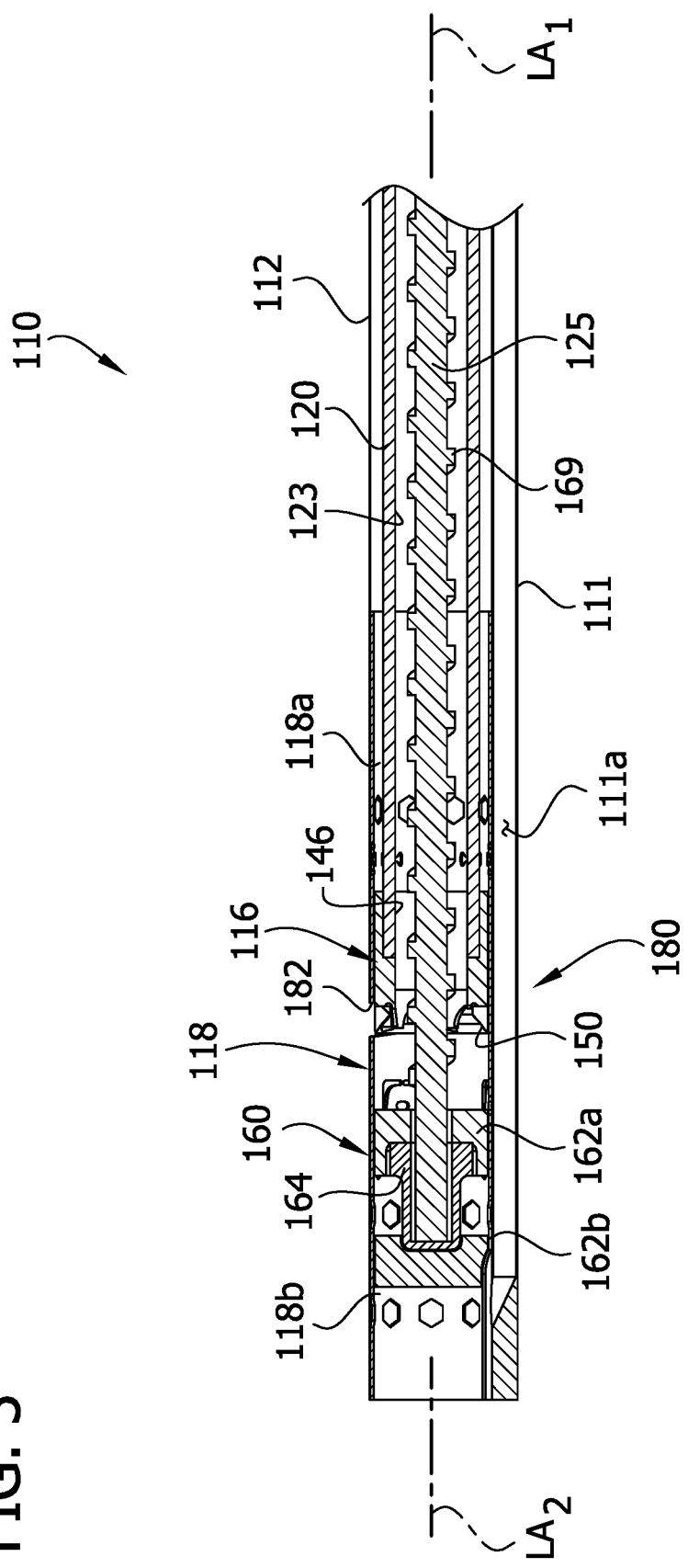
FIG. 3 is a longitudinal section of the distal end portion of the tissue-removing catheter.

Referring to FIGS. 2, 3, and 5, the screw blade 125 extends through the driveshaft 120 and the axial cavity 152 of the cutter 116. In one embodiment (as shown in FIGS. 3 and 5), distal end portion of the screw blade 125 is operably connected to the cutter housing 118 at a location distal of the cutter 116. In particular, the distal end portion of the screw blade 125 is connected to the cutter housing 118 via a rotary bearing mechanism, generally indicated at 160. The Illustrated bearing mechanism 160 constrains axial movement of the screw blade 125 relative to the cutter housing 118, while allowing for the screw blade to rotate about its axis relative to the cutter housing. The bearing mechanism 160 also transmits axial force imparted by the screw blade 125 to the cutter housing 118 to allow for opening and closing of the cutter housing, as explained in more detail below. In the illustrated embodiment, the bearing mechanism 160 includes a pair of longitudinally spaced apart bearings 162a, 162b, and a roller fitting 164 secured to the distal end of the screw blade 125, and rotatably coupled to the bearings. The distal end portion of the screw blade 125 may be connected to cutter housing 118 in other ways.

The screw blade 125 includes a helical thread 169 on the exterior of its shank and extending longitudinally thereon so that rotation of the screw blade 125 about its axis moves removed tissue proximally within the tissue-transport passage 123 of the driveshaft 120. In the illustrated embodiment, the thread 169 is a right-handed thread (as viewed from the proximal end of the driveshaft screw blade 125), such that rotation of the screw blade clockwise (as viewed from the proximal end of the screw conveyor) relative to the tissue-transport passage 123 transports the tissue proximally. The tissue transport passage 123 and the screw conveyor thread 169 may extend back to the proximal end portion of the catheter body 112 and may empty into a tissue receptacle (not shown). The tissue transport passage 123 and screw conveyor thread 169 may stop short of the proximal end portion of the catheter body 112. The thread 169 may be formed on the shank of the screw blade 125 in a suitable manner.

In one example, the cross-sectional dimension (e.g., inner diameter) of the tissue-transport passage 123 is slightly greater than the major diameter of the exterior thread 169 on the screw blade 125 so that there is a small radial gap (or play) between the thread on the screw blade and interior surface of the body 112 defining the tissue-transport passage 123. In this example, the radial gap is such so as not to inhibit or impede rotation and axial movement of the screw blade 125 in tissue-transport passage 123, and at the same time, substantially inhibit tissue from passing between the thread 122 on the screw blade and the interior surface of the driveshaft 130 defining the tissue-transport passage. For example, the diameter of the tissue-transport passage 123 may be from about 0.001 in (0.025 mm) to about 0.020 in (0.508 mm) greater than the major diameter of the exterior thread 169. In another embodiment, the radial gap between the thread 169 on the screw blade 125 and interior surface of driveshaft 120 defining the tissue-transport passage 123 is such that removed tissue is pinched between the thread and the interior surface, without substantially macerating the tissue, to facilitate proximal movement of the tissue. For this embodiment, the radial gap may measure from about 0.005 in (0.127 mm) to about 0.020 in (0.508 mm), and in one example, from about 0.010 in (0.254 mm) to about 0.015 in (0.381 mm). It is understood that in some embodiments the screw conveyor 122 may be omitted without departing from the scope of the present invention.

Referring to FIG. 1, the proximal end of the screw blade 125 is operably connected to a conveyor motor 166 (broadly, a conveyor driver) to impart rotation of the screw blade 125 relative to catheter body 112. In one example, the conveyor motor 166 is disposed within the handle 132 (shown with a cover removed in FIG. 10) that is releasably connectable to the proximal end of the catheter 110. The power source 134 (e.g., batteries) may also power the conveyor motor 166, or a different power source may be provided. A different microswitch (not shown) may be used to activate the conveyor motor 166. A lever 140 (or other actuator) controls rotation of the screw blade 125 via the conveyor motor 166. In the Illustrated embodiment, the lever 140 also imparts axial movement of the screw blade 125 relative to the catheter body 112 in order to actuate the deployment mechanism 124, as explained below. In one embodiment, the conveyor motor 166 is operable independent of the cutter motor 130 to allow for transportation of removed tissue even if the cutter 116 is not in operation. It is understood that the screw blade 125 may be driven in other ways without departing from the scope of the present invention.

As set forth above, the tissue removed from the blood vessel by the cutting edge 150 passes proximally through the cutter 116, toward the tissue-transport passage 123 of the cutter driveshaft 130. In the illustrated embodiment, the screw blade 125 picks up removed tissue within the axial cavity 152 in the cutter 116 because the screw blade and the screw blade thread 169 extend through the cutter to a distal location. Thus, as can be seen from FIG. 14, as the tissue is being removed, it enters the axial cavity 152 in the cutter 116, where it is picked up by the screw blade 125, and transported proximally through the stem 144 of the cutter and into the tissue-transport passage 123, where it continues to be transported proximally by the screw blade. It is understood that the screw blade 125 may be of other configurations in other embodiments of the catheter without departing from the scope of the present invention.

Figure 4:
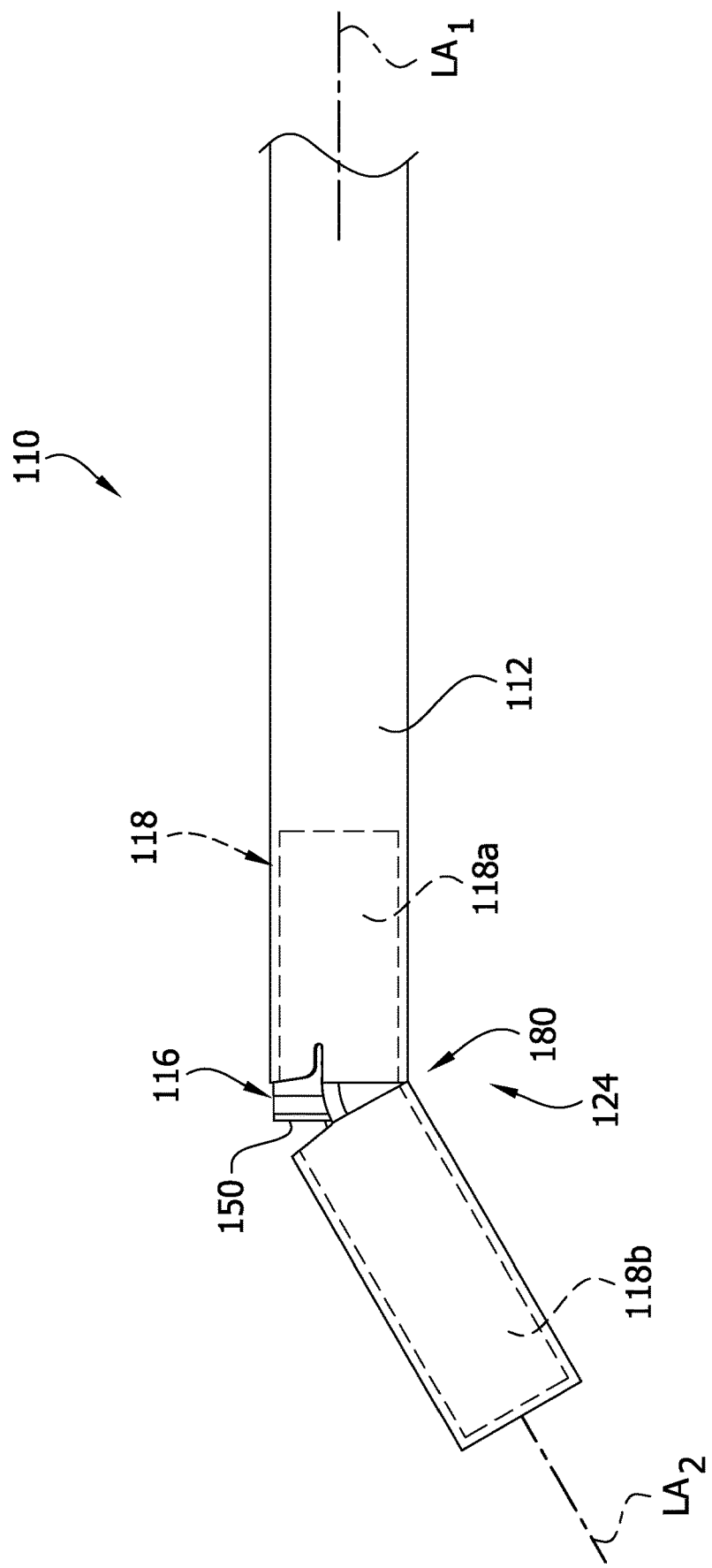
FIG. 4 is an enlarged side elevation of the distal end portion of the tissue-removing catheter, with the cutter of the tissue-removing catheter in a deployed, cutting position.

As set forth above, the catheter 110 includes the deployment mechanism 124 for configuring the cutter 116 between the retracted position (FIGS. 1 and 3) and the deployed, cutting position (FIGS. 4 and 5). For purposes of the disclosure, the deployment mechanism 124 is considered part of the catheter body 12, and in particular, part of the distal end portion of the catheter body. As also set forth above, the deployment mechanism 124 includes the cutter housing 118. The cutter housing 118 is generally tubular and includes a proximal longitudinal portion 118a, a distal longitudinal portion 118b, a hinge portion 180 interconnecting the proximal and distal longitudinal portions, and a cutter window 182 generally diametrically opposite the hinge portion and intermediate the proximal and distal longitudinal portions. In general, the distal longitudinal portion 118a is pivotable relative to the proximal longitudinal portion 118b about the hinge portion 180 (generally having a hinge axis $A_{H2}$) (FIG. 10) to selectively open the deployment mechanism 124 and expose at least a portion of the cutting edge 150 through the cutter window 182 (FIG. 5), and selectively close the deployment mechanism so that cutting edge is stored in the cutter housing (FIG. 3). More specifically, axial movement of the screw blade 125 imparts a longitudinal or axial force to the bearing mechanism 160, which transmits the force to the distal longitudinal portion 118b of the cutter housing 118. Because of the hinge portion 180, the axial force transmitted to the distal longitudinal portion 118b is translated into rotational movement of the distal longitudinal portion about the hinge portion (generally about the hinge axis $A_H$). It is understood that the polymer jacket 111, if one is present on the catheter body 112, does not substantially inhibit bending of the cutter housing 118 at the hinge portion 180.

To open the cutter housing 118 so that the cutting edge 150 is exposed through the window 182, the screw blade 125 is moved distally within the catheter body 112, such as by moving the lever 140 distally on the handle 132, whereby the distal longitudinal portion 118b pivots about the hinge portion 180, away from the cutter 116, and the cutting edge 150 protrudes through the window. As shown in FIG. 4, in the open position, a longitudinal axis $LA_2$ of the distal longitudinal portion 118b extends at an offset angle relative to a longitudinal axis of the catheter body 212 (and the proximal longitudinal portion 118a, which is generally coaxial with the catheter body). This offset angle may measure from about 15 degrees to about 45 degrees, or from about 20 degrees to about 30 degrees. To close the cutter housing 174 so that the cutting edge 150 does not protrude through the window 182 (e.g., the cutting edge is housed within the housing), the screw blade 125 is moved proximally within the catheter body 112, such as by moving the lever 140 proximally on the handle 132, whereby the distal longitudinal portion 118b pivots about the hinge portion 180, toward the cutter 116. As shown in FIG. 3, in the closed configuration, the longitudinal axis $LA_2$ of the distal longitudinal portion 118b may be generally coaxial with the longitudinal axis $LA_1$ of the catheter body 212 (and the proximal longitudinal portion 118a). Although in the illustrated embodiment the screw blade 125 functions as a longitudinal force-transmitting component to transmit a longitudinal or axial force to the cutter housing 118 to impart pivoting of the cutter housing 118 at the hinge portion 180, in other embodiments the screw blade may be replaced with another type of longitudinal force-transmitting component to perform the same function. For example, in another embodiment an elongate, flexible member may replace the screw blade 125. This member may be capable transmitting longitudinal forces to the cutter housing 118 due to compressive and tensile loads applied to the member to actuate opening and closing of the cutter housing.

Figure 8:
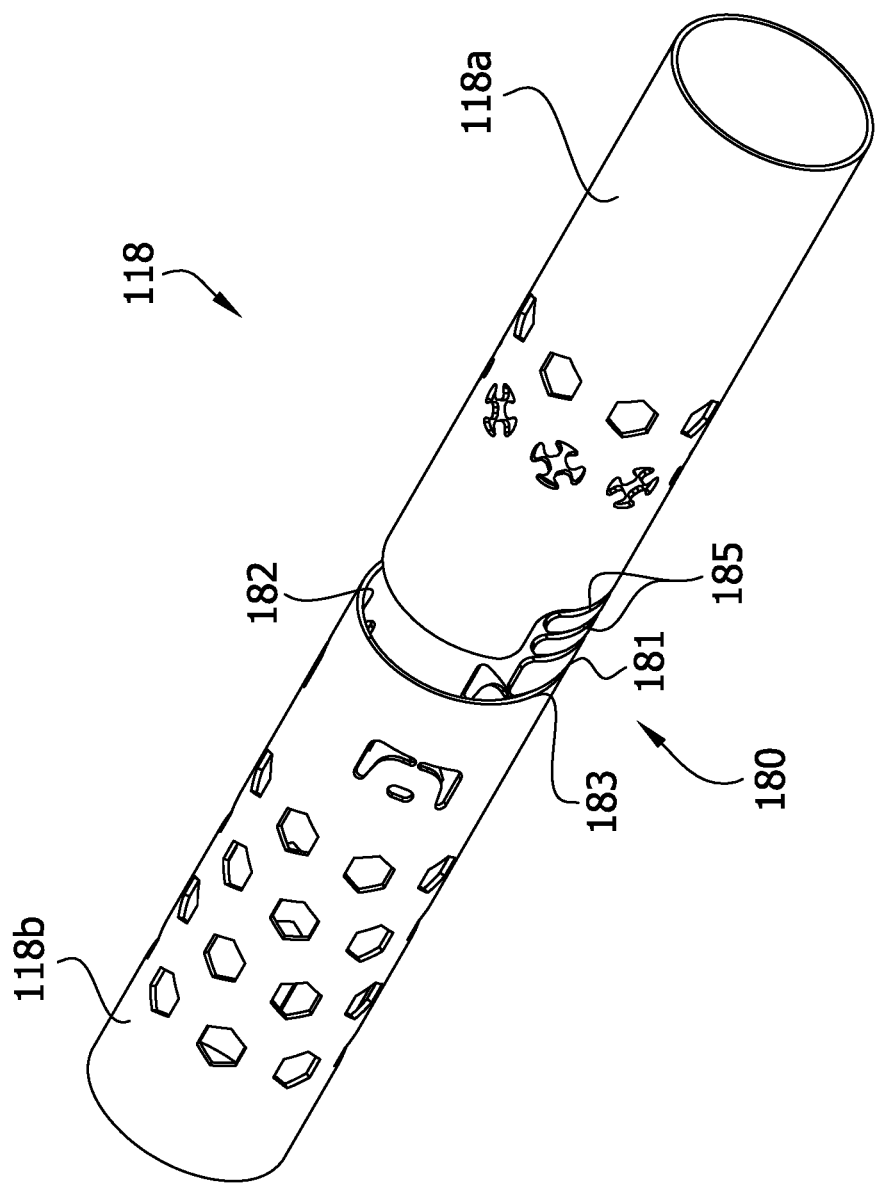
FIG. 8 is an enlarged perspective of a cutter housing of the tissue-removing catheter, the cutter housing being in a closed position.
Figure 9:
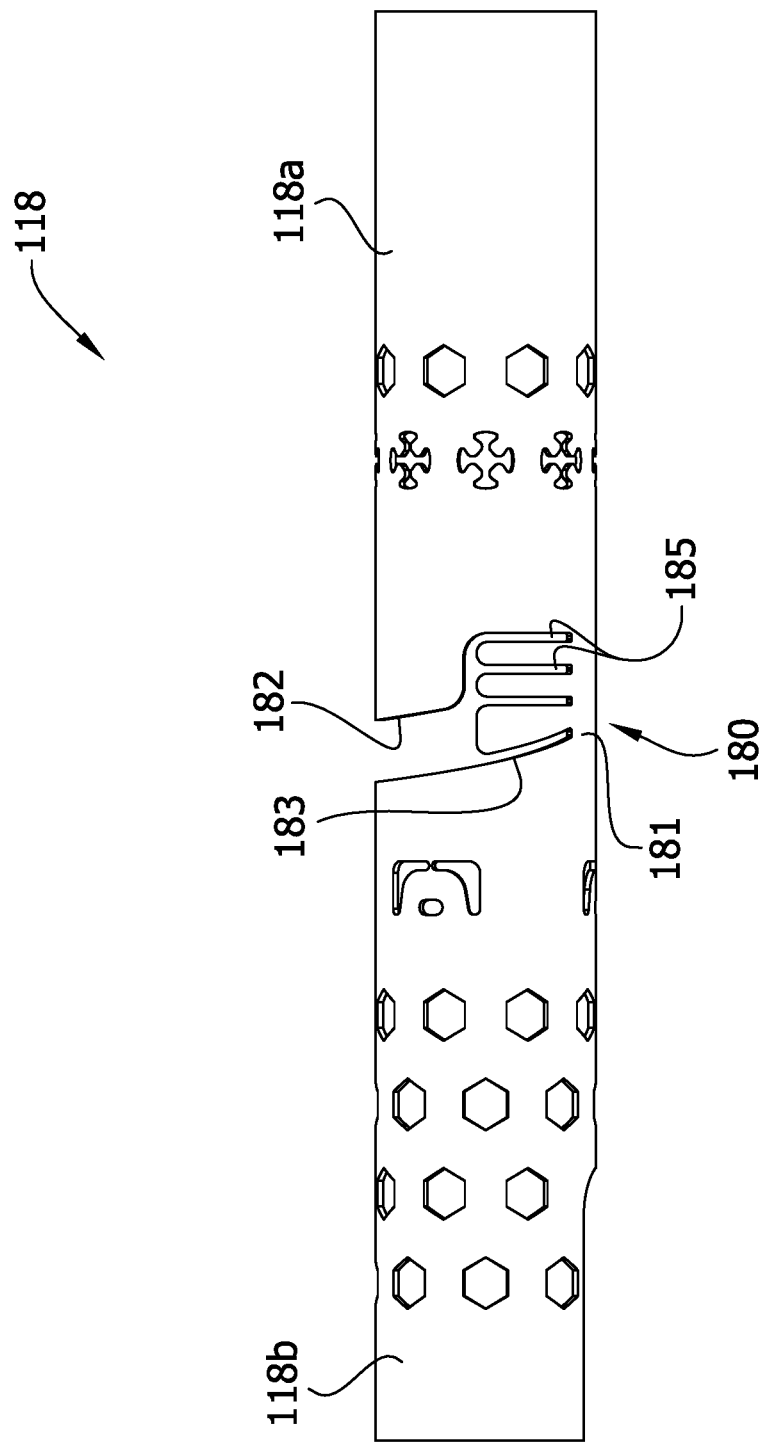
FIG. 9 is a side elevational view of the cutter housing of FIG. 8.
Figure 10:
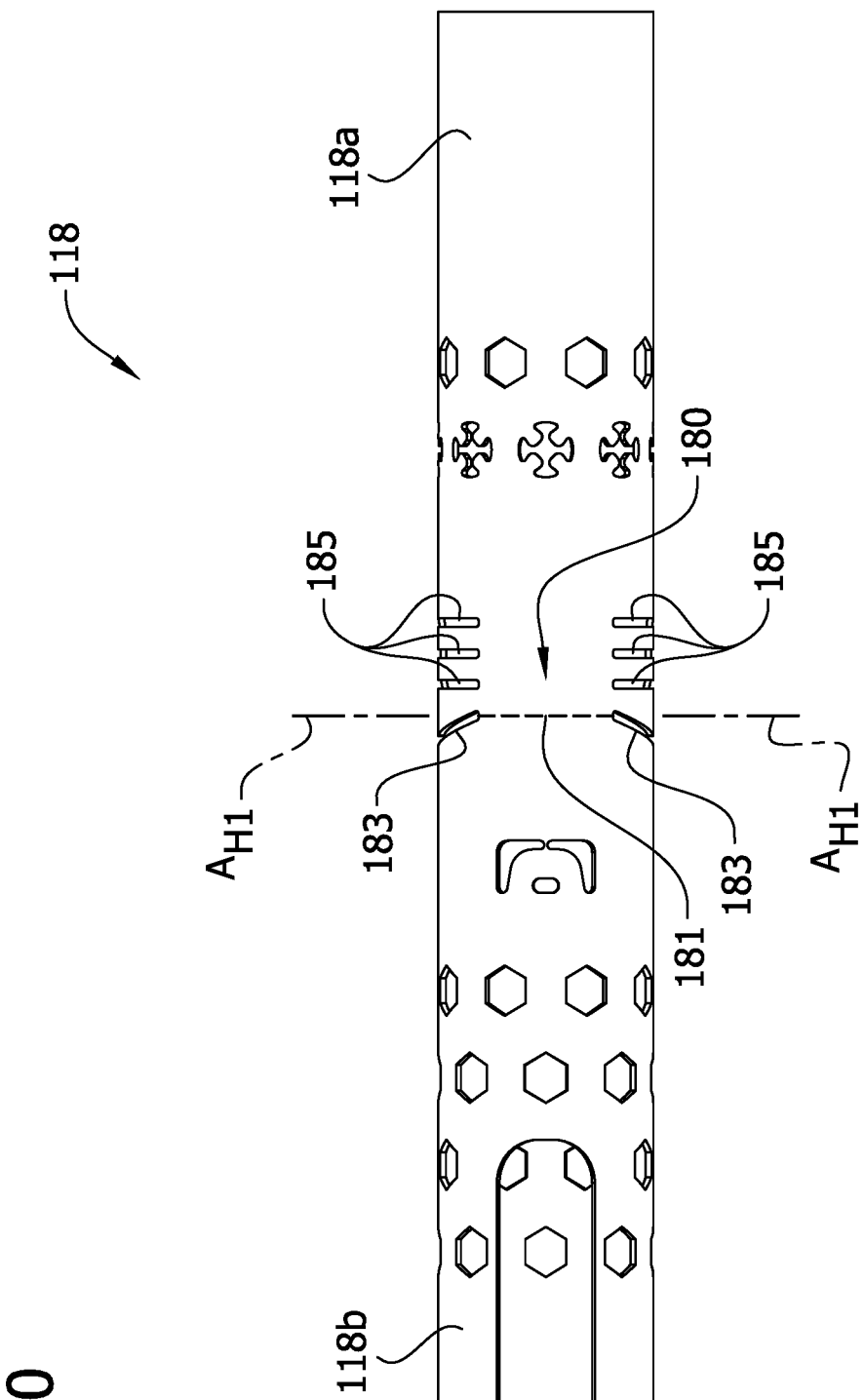
FIG. 10 is a bottom plan view of the cutter housing of FIG. 8.
Figure 11:
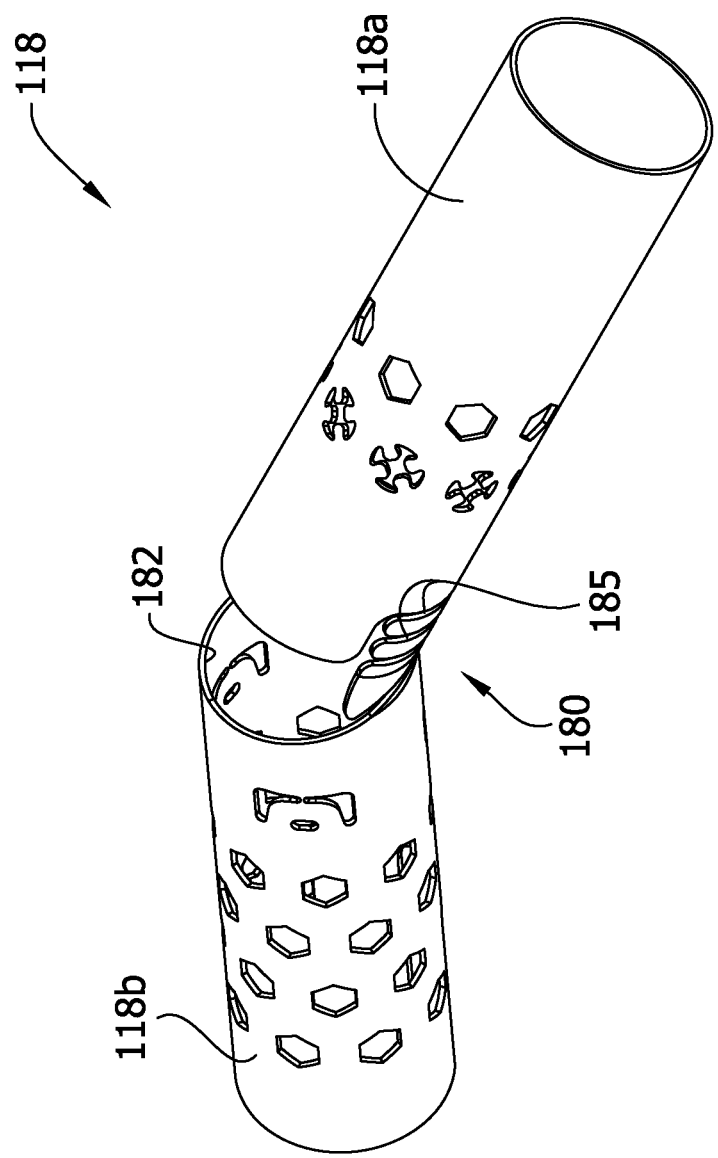
FIG. 11 is similar to FIG. 8, but with the cutter housing in an open position.

As shown best in FIG. 8, the proximal and distal longitudinal portions 118a, 118b, respectively, of the cutter housing 118 are generally tubular, although each may be of other shapes. The window 182 comprises a generally arcuate cutout or opening extending around a partial circumference of the cutter housing 118. The hinge portion 180 comprises an arcuate line of weakness (e.g., a living hinge) 181 that runs around a partial circumference of the cutter housing 118, generally diametrically opposite that of the window 182. For example, the line or weakness 181 may extend circumferentially between two, circumferentially spaced apart arcuate slots 183 in the tubular housing 118. Additional, spaced apart arcuate slots 185 may be formed proximal of the arcuate slots 183, to allow for bending at the hinge portion 180. The cutter housing 118 may comprise an integral, one-piece component. The window 182 and arcuate slots 183 (and other openings) may be formed by cutting (e.g., laser cutting).

It is understood that in other embodiments, the hinge portion 180 may be of other configurations to allow for pivoting of the distal longitudinal portion 118b relative to the proximal longitudinal portion 118a. For example, the hinge portion 180 may comprise a hinge pin, a trunnion, another type of living hinge, or the like, that enables the distal longitudinal portion 118b to pivot (broadly, deflect)

relative to the proximal longitudinal portion 118a, generally transverse to the longitudinal axis $LA_1$.

Figure 13:
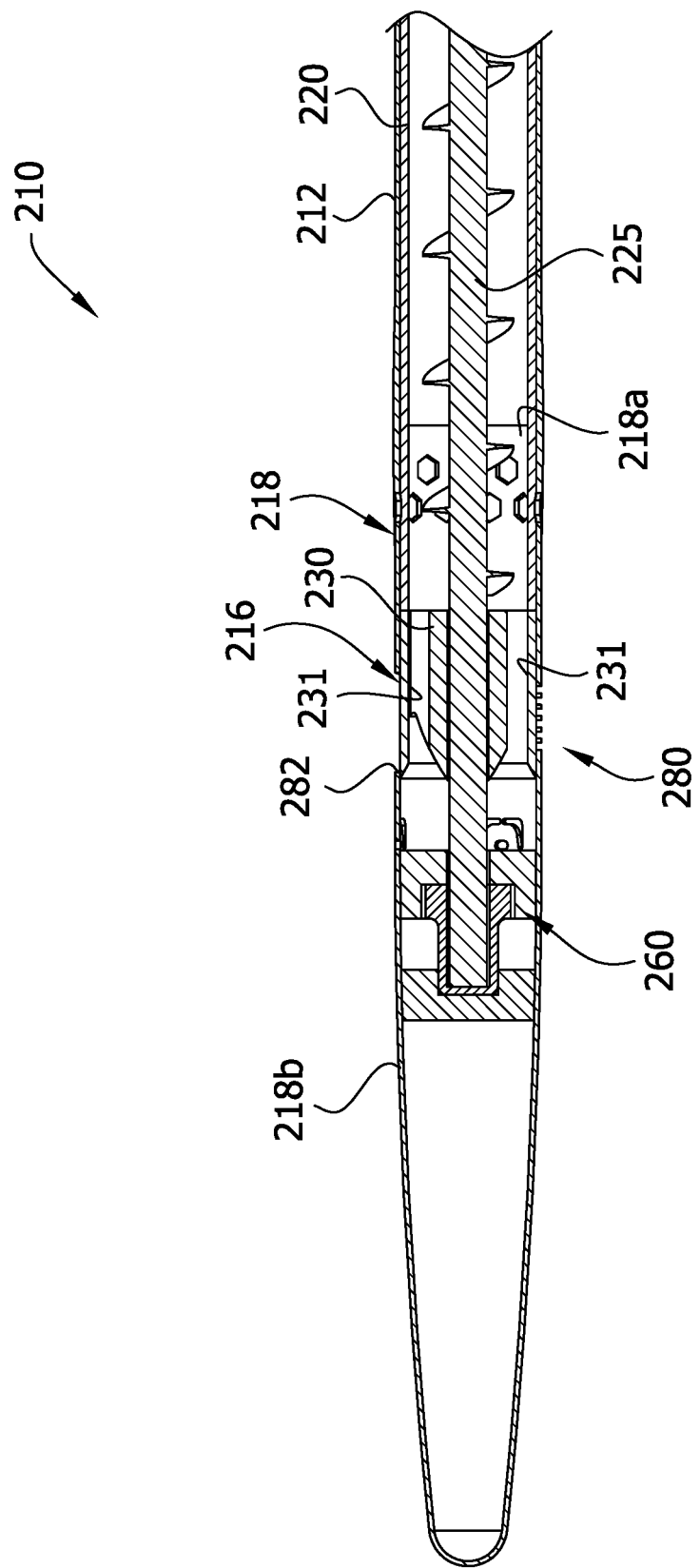
FIG. 13 is an enlarged longitudinal section of a distal portion of a second embodiment of a tissue-removing catheter, a cutter housing of the catheter being in a closed position.

Referring to FIGS. 13-18 and FIGS. 54-55, a second embodiment of a cutter housing is generally indicated at 218. As shown in FIGS. 13 and 14, the cutter housing 218 is installed in a second embodiment of the catheter, generally indicated at 210, that is constructed similar to the catheter 110, including a catheter body 212, a cutter driveshaft 220, and a screw blade 225, each of which may be similar or identical to the corresponding components of the first catheter 110, and therefore, corresponding disclosure set forth with respect to the first catheter is equally applicable to the present embodiment. Referring to FIGS. 13-14 and FIGS. 54-55, the cutter 216 is different than the cutter 116 of the first embodiment, although the cutter may also be similar or identical to the cutter 116 of the first catheter 110. Unlike the cutter 116, the present cutter 216 includes a center hub 230 defining a central, longitudinal passage 230a through which the screw blade 225 extends. A plurality of longitudinal flutes 231 (e.g., two flutes) extend longitudinally through the cutter 216. The flutes 231 are spaced apart around the center hub 230. Tissue removed by the cutting edge 250 pass through the flutes 231 and enter the tissue-transport passage 232 defined by the driveshaft 220, where the removed tissue is picked up by the rotating screw blade 225.

As with the first cutter housing 118, the present cutter housing 218 includes a proximal longitudinal portion 218a, a distal longitudinal portion 218b, a hinge portion, generally indicated at 280, interconnecting the proximal and distal longitudinal portions, and a cutter window 282 generally diametrically opposite the hinge portion and intermediate the proximal and distal longitudinal portions. The distal longitudinal portion 118b includes a nosecone. Moreover, the screw blade 225 is rotatably secured to the distal longitudinal portion 118b of the cutter housing 218 by a bearing mechanism 260, that may be identical to the bearing mechanism set forth above with respect to the first catheter. In general, the distal longitudinal portion 218b is pivotable relative to the proximal longitudinal portion 218a about the hinge portion 280 (generally having a hinge axis $A_{H2}$, FIG. 16) to selectively open the cutter housing 218 (broadly, to open the deployment mechanism 224) and expose at least a portion of the cutting edge 250 through the cutter window 282 (FIG. 14), and selectively close the cutter housing so that cutting edge is stored in the cutter housing (FIG. 13).

Referring to FIGS. 15-18, the cutter housing 218 is formed from a one-piece hypotube, such as a plastic or metal hypotube (e.g., stainless steel) or other type of hypotube. The window 282 is generally arcuate, extending generally circumferentially along a portion of the circumference of the cutter housing 218, and has opposite circumferential sides 283. For example, the window 282 may extend along less than 50% of the circumference of the cutter housing 218. The hinge portion 280 comprises a plurality of arcuate slots 285 spaced apart along the length of the hypotube. Each arcuate slot 285 extends generally circumferentially from one circumferential side 283 of the window 282 toward the opposite circumferential side of the window and terminates adjacent to, but not in communication with, the opposite circumferential side of the window. Adjacent arcuate slots 285 alternate such that adjacent slots do not extend from the same side of the window 282 so as to form longitudinally spaced apart connecting portions 287 adjacent the opposite sides of the window. As such, the hinge portion 280 comprises a plurality of interconnected z-shape segments extending along the length of the cutter housing 218, which forms a metallic skeleton. A polymer jacket (not shown), such as disclosed above with respect to the first embodiment, may be provided over the metallic skeleton. The window 282 and the hinge portion 280 (e.g., the slots or other openings forming the metallic skeleton) may be formed by cutting, such as laser cutting, the hypotube. In the illustrated embodiment, the cutter housing 218 is biased in its closed position, although the cutter housing may be formed such that it is biased in its closed position.

An exemplary operation of the first catheter 110 is set forth below, with the understanding the disclosed operation is applies equally to the second catheter 210. The catheter 110 is inserted into the body lumen (e.g., artery) such that the cutter 116 is positioned adjacent the target site. Fluoroscopy or other imaging techniques may be used to facilitate placement of the catheter 110 in the body lumen. During placement of the catheter 110 in the body lumen, the cutter housing 118 (broadly, the deployment mechanism 124) is closed and the cutter 116 is in the covered position. At the target site, the cutter housing 118 is opened, such as by moving the lever 140 on the handle 132 distally, to impart distal movement of the screw blade 125 relative to the catheter body 112 and the cutter housing 118. As the screw blade 125 moves distally, the distal longitudinal portion 118b of the cutter housing 118 pivots relative to the proximal longitudinal portion 118a about the hinge axis $A_{H1}$ at the hinge portion 180 such that a portion of the cutting edge 150 of the cutter 116 extends through the cutter window 180 defined by the cutter housing. As explained above, an urging mechanism (not shown) may urge the cutting edge 150 toward the wall of the body lumen, and the offset distal longitudinal portion 118b of the cutter housing 118 may also facilitate urging of the cutting edge toward the lesion site.

With the cutter housing 118 open and the cutting edge 150 at least partially exposed through the window 180, the cutter driver 130 may be activated to actuate rotation of the cutter driveshaft 120 and the cutter 116 relative to the catheter body 112. The screw blade 125 may also be activated, such as by moving the switch 133, or alternatively, the screw blade may be automatically activated upon moving the lever 140 distally, which opens the cutter housing 118. The catheter 110 is moved distally through the body lumen, whereby the rotating cutter 116 removes tissue from the lesion site. The removed tissue is picked up by the rotating screw blade 125 and transported proximally within the tissue-transport passage 123 in the catheter body 112. After making a pass through the lesion site, the cutter housing 118 may be closed by moving the screw blade 125 proximally, such as by moving the lever 140 proximally, to impart pivoting of the distal longitudinal portion 118b of the cutter housing 118 toward the cutter 116 about the hinge axis $A_{H1}$ at the hinge portion 180. The cutter driver 130 may be deactivated before or after closing the cutter housing 118, or the cutter driver may remain on. In one example, the screw blade 125 may remain on (e.g., the user may keep the conveyor driver 133 on) after closing the cutter housing 118 so that screw blade continues to transport the removed tissue proximally within the catheter body 112. With the cutter housing 118 closed, the catheter 110 is moved proximally within the body lumen, to allow the practitioner to take another pass through the lesion site.

Figure 19:
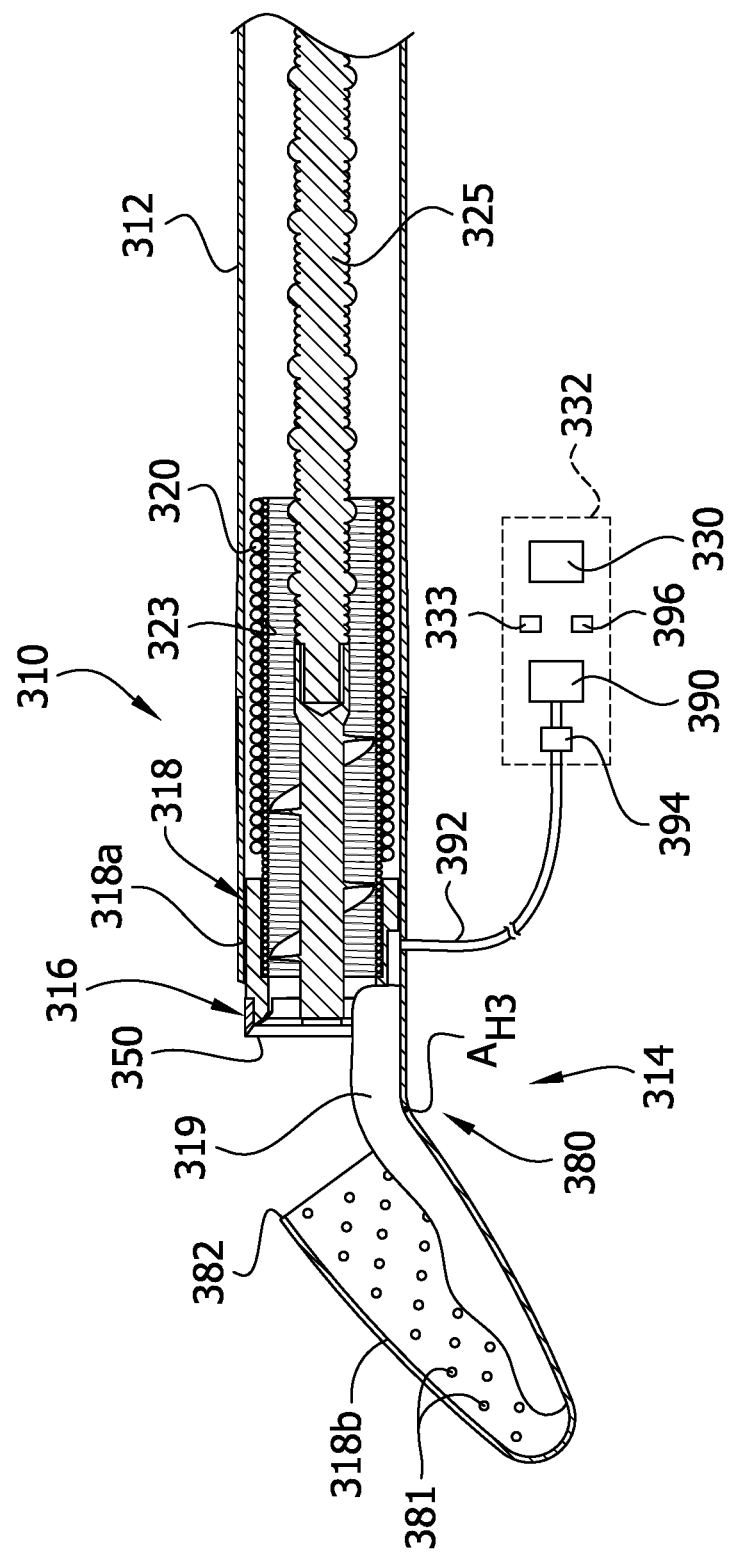
FIG. 19 is a side elevational view of a distal end portion of a third embodiment of a tissue-removing catheter, with a cutter housing of the catheter being in an open position, and the cutter housing and the cutter driveshaft being partially transparent.
Figure 20:
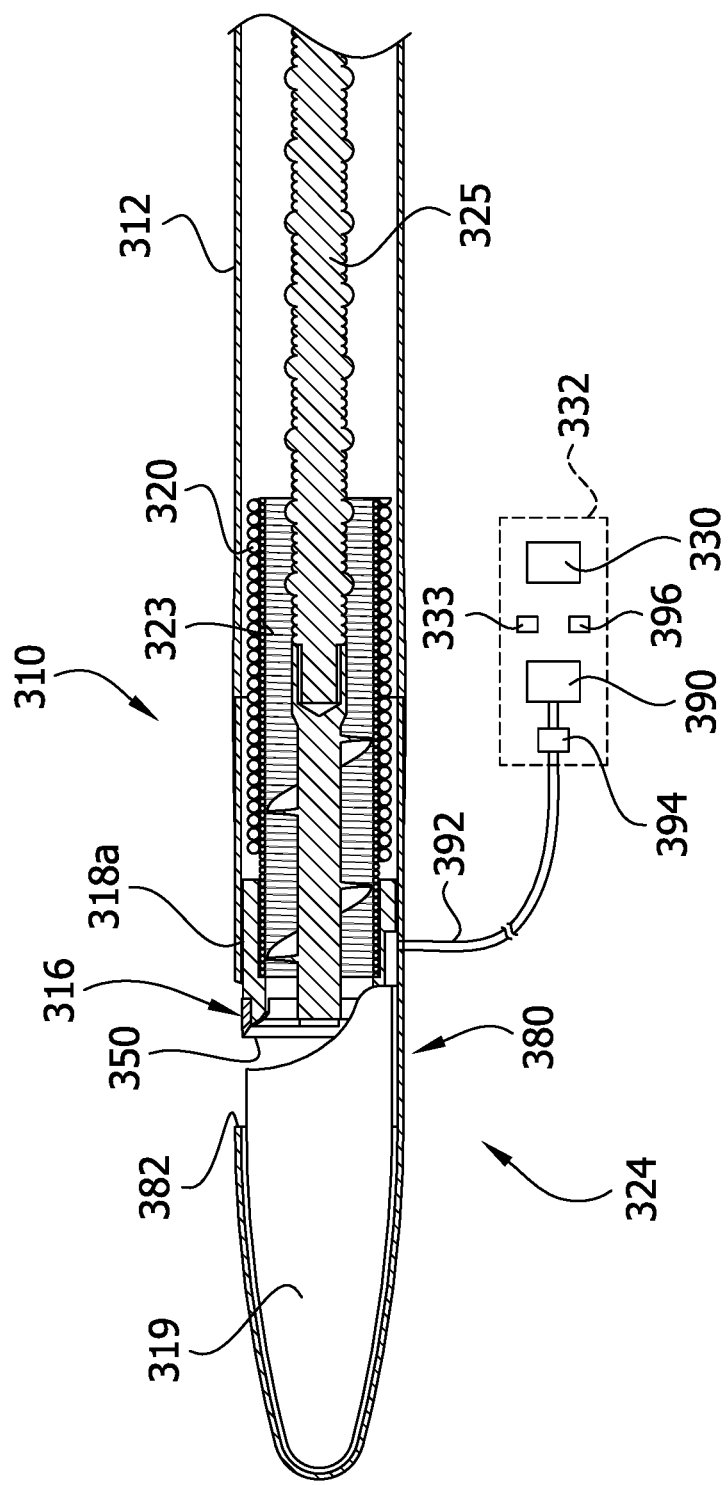
FIG. 20 is similar to FIG. 19, but with the cutter housing in a closed position.

Referring to FIGS. 19 and 20, a third embodiment of a tissue-removing catheter is generally indicated at 310. With the exception of a deployment mechanism 324, the third catheter 310 may be constructed similar to the catheter 110, including a catheter body 312, a cutter 316 (including a cutting edge 350), and a cutter driveshaft 320, each of which may be similar or identical to the corresponding components of the first catheter 110, and therefore, corresponding disclosure set forth with respect to the first catheter is equally applicable to the present embodiment. In the illustrated embodiment, the catheter includes a screw blade 325 received in tissue-transport passage 323 defined by an interior surface of the driveshaft 320. Unlike the previous catheter embodiments 110, 210, a distal end of the screw blade 325 terminates proximal of the cutting edge 350 of the cutter 316. In other embodiments, the cutter 316 and the driveshaft 320 may be of different configurations, such as the driveshaft being solid.

The deployment mechanism 324 of the present catheter 310 comprises a cutter housing 318 and an expandable member 319 that is configured to selectively expand in volume. The cutter housing 318 may be substantially similar to the cutter housing 118 or 218, in that the cutter housing includes a proximal longitudinal portion 318a, a distal longitudinal portion 318b, a hinge portion 380 interconnecting the proximal and distal longitudinal portions, and a cutter window 382 generally diametrically opposite the hinge portion and intermediate the proximal and distal longitudinal portions. The distal longitudinal portion 318b includes a nosecone, which may include openings 381, such that the nosecone functions as an embolic basket. That is, the nosecone may function to catch tissue (e.g., debris) that is cut by the cutter 316 but did not enter the cutter and the tissue. In general, the distal longitudinal portion 318b is pivotable relative to the proximal longitudinal portion 318a about the hinge portion 380 (generally having a hinge axis $A_{H3}$) to selectively open the cutter housing 318 (broadly, to open the deployment mechanism 224) and expose at least a portion of the cutting edge 350 through the cutter window 382 (FIG. 19), and selectively close the cutter housing so that cutting edge is stored in the cutter housing (FIG. 20).

The expandable member 319 is operatively connected to the cutter housing 318 such that selective expansion of the expandable member from a contracted state (FIG. 19) to an expanded state (FIG. 20) imparts rotation or pivoting of the distal longitudinal portion 318b of the cutter housing about the hinge axis $A_{H3}$ at the hinge portion 380. In the illustrated embodiment, the cutter housing 318 is biased in an open position (FIG. 19), whereby the distal longitudinal portion 318b extends at an offset angle relative to the proximal longitudinal portion 318a (similar to the previous cutter housings 118, 218). Thus, when the expandable member 319 is in its contracted state, the cutter housing 318 is open and the cutting edge 350 of the cutter 316 is exposed, and when the expandable member is in its expanded state, the cutter housing is closed and the cutting edge is covered by the distal longitudinal portion 318b.

In the illustrated embodiment, the expandable member 319 comprises an inflatable balloon in fluid communication with a source of fluid (e.g., saline) 390 via tubing 392 extending along the catheter body 312. In the drawings, the tubing 392 is illustrated schematically and shown extending outside the catheter body 312 for ease of illustration, with the understanding that the tubing may extend within the catheter body. The source of fluid 390 may be provided within a handle 332, which may be similar to the handle 232, or separate from the handle. In the drawings, the handle 332 is shown schematically and is not shown operatively connected to the catheter body for ease of illustration, with the understanding that the handle would be operatively connected to the catheter body similar to the previous embodiments. The handle includes a cutter driver 330 similar to the cutter driver 230, and an actuator 333 (e.g., a button) for activating the cutter driver to drive rotation of the driveshaft 325 and the cutter 316. A fluid pump 394 may be used to deliver the fluid into the balloon. The handle (or some other device) may include an actuator 396 (e.g., a button or switch) for selectively activating the fluid pump to deliver the fluid to the balloon, thereby inflating the balloon and closing the cutter housing 318. To open the cutter housing 318, the fluid pump 394 or some other device (e.g., a vacuum) may be selectively activated to withdrawal the fluid from the balloon, whereby the balloon deflates and the cutter housing 318 opens.

An exemplary use of the catheter 310 may be similar to the exemplary uses of the first catheter 110 set forth above, with the exception being that the cutter housing 318 is opened and closed using the expandable member 319, as disclosed above.

Figure 21:
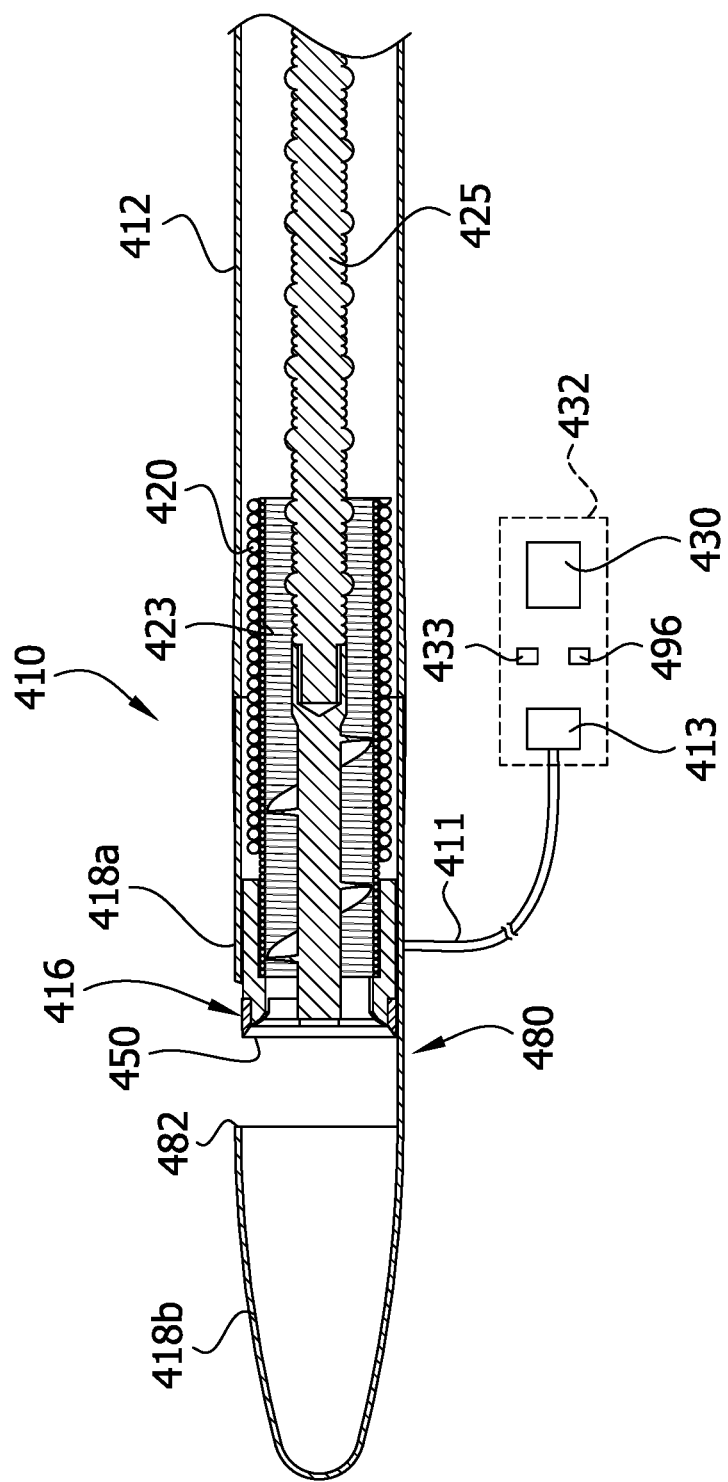
FIG. 21 is a side elevational view of a distal end portion of a fourth embodiment of a tissue-removing catheter, with a cutter housing of the catheter being in an closed position, and the cutter housing and the cutter driveshaft being partially transparent.
Figure 22:
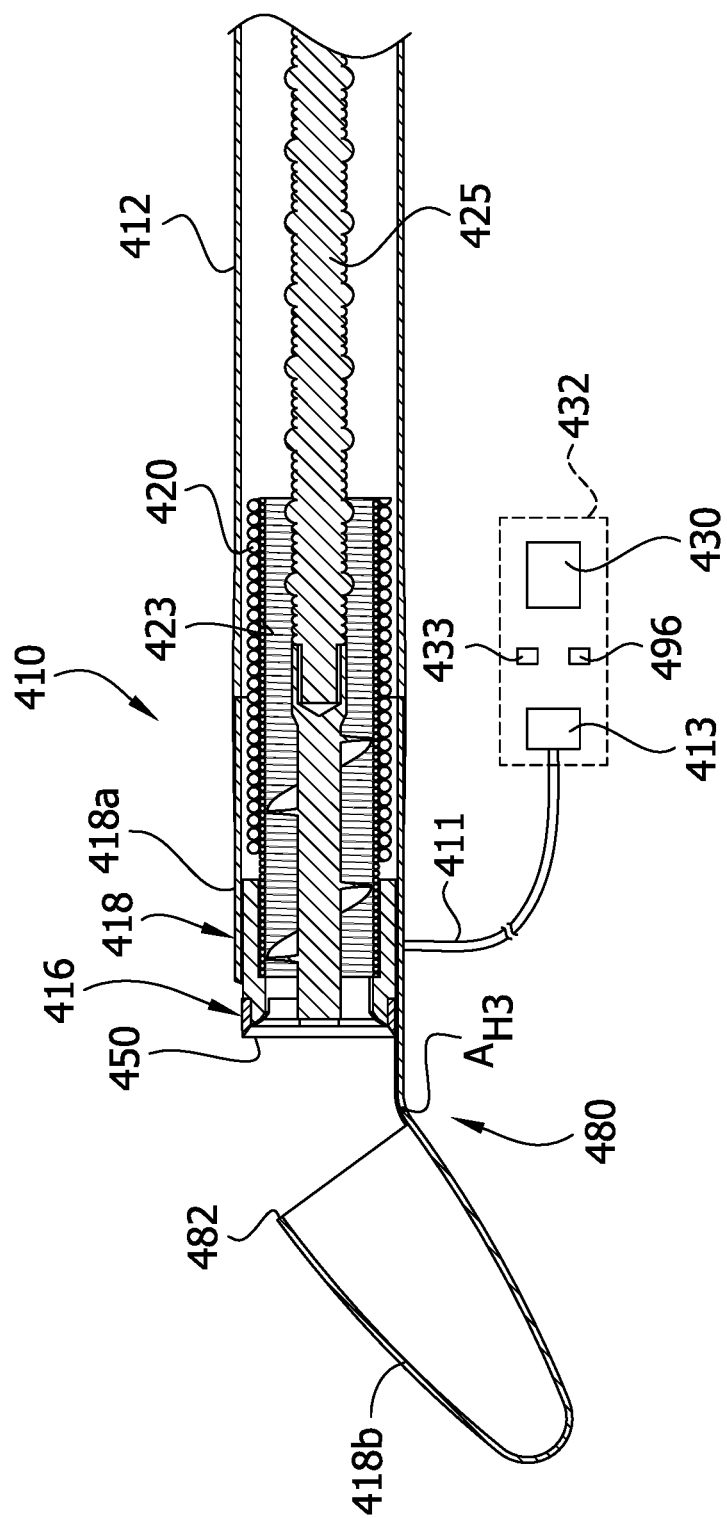
FIG. 22 is similar to FIG. 21, but with the cutter housing in an open position.

Referring to FIGS. 21 and 22, a fourth embodiment of a tissue-removing catheter is generally indicated at 410. The illustrated tissue-removing catheter 410 is similar to the tissue-removing catheter 210, except that a cutter housing, generally indicated at 418, comprises heat-activating, shape-memory material, such as nitinol or other shape-memory material, and an electrical conductor 411 electrically connected to the cutter housing 418 for delivering electrical current to the cutter housing for opening and closing the cutter housing, as explained below. With than these differences, the fourth catheter 410 may be constructed similar to the catheter 210, including a catheter body 412; a cutter 416 having a cutting edge 450; a cutter housing 418 having a window 482 and proximal and distal longitudinal portions 418a, 418b connected by a hinge portion 480; and a cutter driveshaft 420, each of which may be similar or identical to the corresponding components of the second catheter 210, and therefore, corresponding disclosure set forth with respect to the first catheter is equally applicable to the present embodiment. In the illustrated embodiment, the catheter 410 includes a screw blade 425 received in tissue-transport passage 423 defined by an interior surface of the driveshaft 420. Like the third catheter embodiment 310, a distal end of the screw blade 425 terminates proximal of the cutting edge 450 of the cutter 416. In other embodiments, the cutter 416 and the driveshaft 420 may be of different configurations, such as the driveshaft being solid.

In one example, the entire cutter housing 418 may comprise a single, one-piece construction comprising the shape-memory material (e.g., nitinol). For example, the cutter housing 418 may be formed from a hypotube comprising nitinol or another shape-memory material. In another example, only the hinge portion 480 comprises nitinol or another shape-memory material, and the hinge portion 480 may be secured to the proximal and distal longitudinal portions 418a, 418b in a suitable fashion. The proximal and distal longitudinal portions 418a, 418b may be formed from a different material, such as a rigid metal or plastic.

In the illustrated embodiment, the cutter housing 418 is configured such that the original, non-activated shape of the cutter housing is its closed position (FIG. 21) and the activated shape of the cutter housing is its open position (FIG. 22). The catheter 410 may include an electrical power source 413 (e.g., a battery) that is electrically connected to the electrical conductor 411 (e.g., a cable or wire), which is, in turn, electrical connected to the shape-memory material of the cutter housing 418. In the drawings, the electrical conductor 411 is illustrated schematically and shown extending outside the catheter body 412 for ease of illustration. The power source 413 may be provided within a handle 432, which may be similar to the handle 232, or separate from the handle. In the drawings, the handle 432 is shown schematically and is not shown operatively connected to the catheter body 412 for ease of illustration, with the understanding that the handle would be operatively connected to the catheter body similar to the previous embodiments. The handle 432 includes a cutter driver 430 similar to the cutter driver 230, and an actuator 433 (e.g., a button) for activating the cutter driver to drive rotation of the driveshaft 425 and the cutter 416. The handle (or some other device) includes an actuator 496 (e.g., a button or switch) for selectively activating the power source 413 to supply electrical current to the cutter housing 418.

When electrical current is applied to the cutter housing 418, the shape-memory material is heated by resistive heating to a temperature at or above its transformation temperature, whereby the cutter housing 418 bends at the hinge portion 480 (generally about a hinge axis $A_{H4}$) to open the cutter housing and expose the cutter 416 (FIG. 22). To close the cutter housing 418, the electrical power source 413 is deactivated to cease the supply of electrical current to the cutter housing, whereupon the shape-memory material cools and rebounds to its original, closed position (FIG. 21).

An exemplary use of the catheter 410 may be similar to the exemplary uses of the first catheter 110 set forth above, with the exception being that the cutter housing 418 is opened and closed by supplying electrical current to the shape-memory material, as set forth above.

Figure 23:
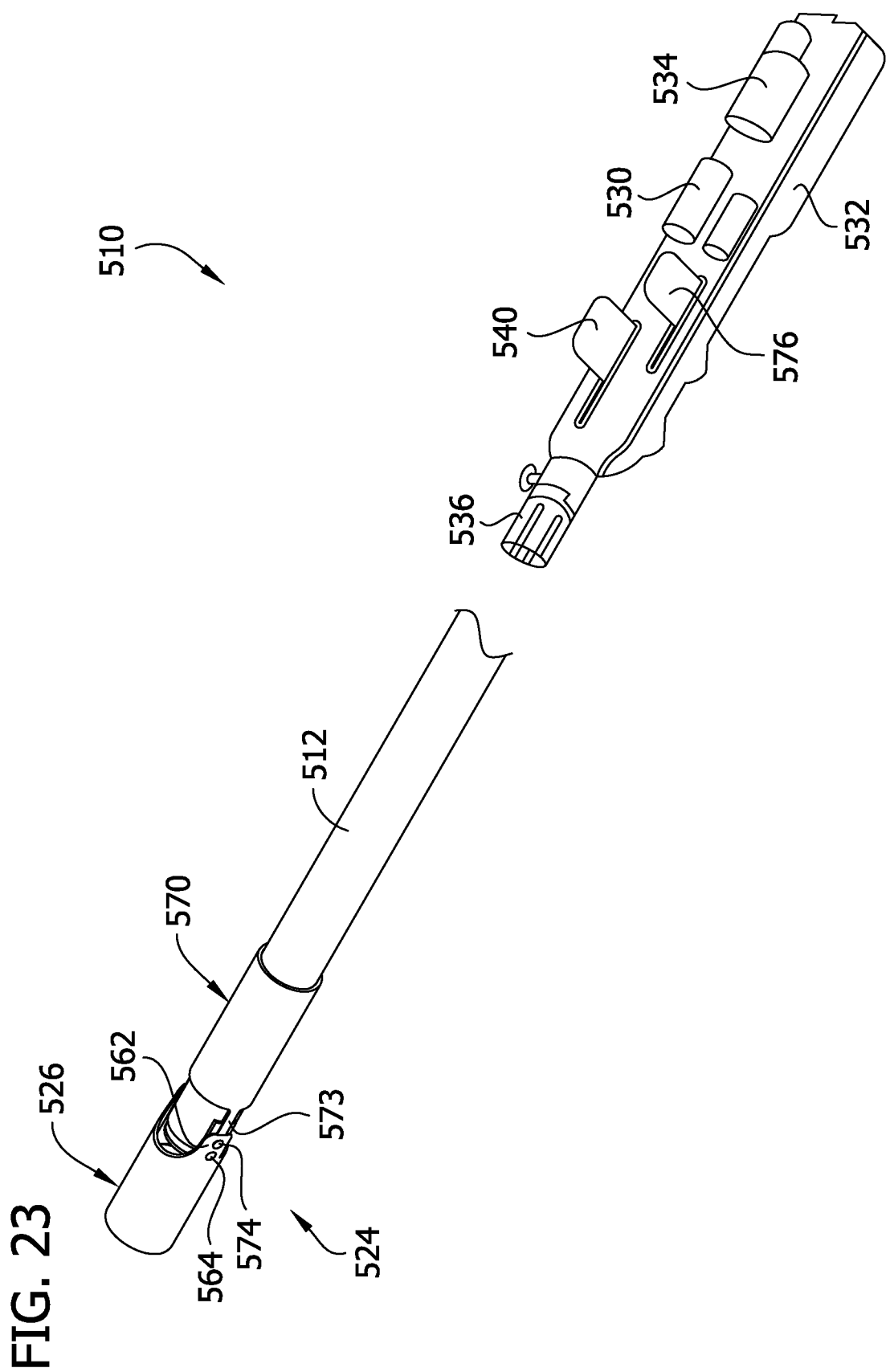
FIG. 23 is a fragmentary perspective of a fifth embodiment of a tissue-removing catheter, including a removable handle attachable to a proximal end of the catheter.
Figure 24:
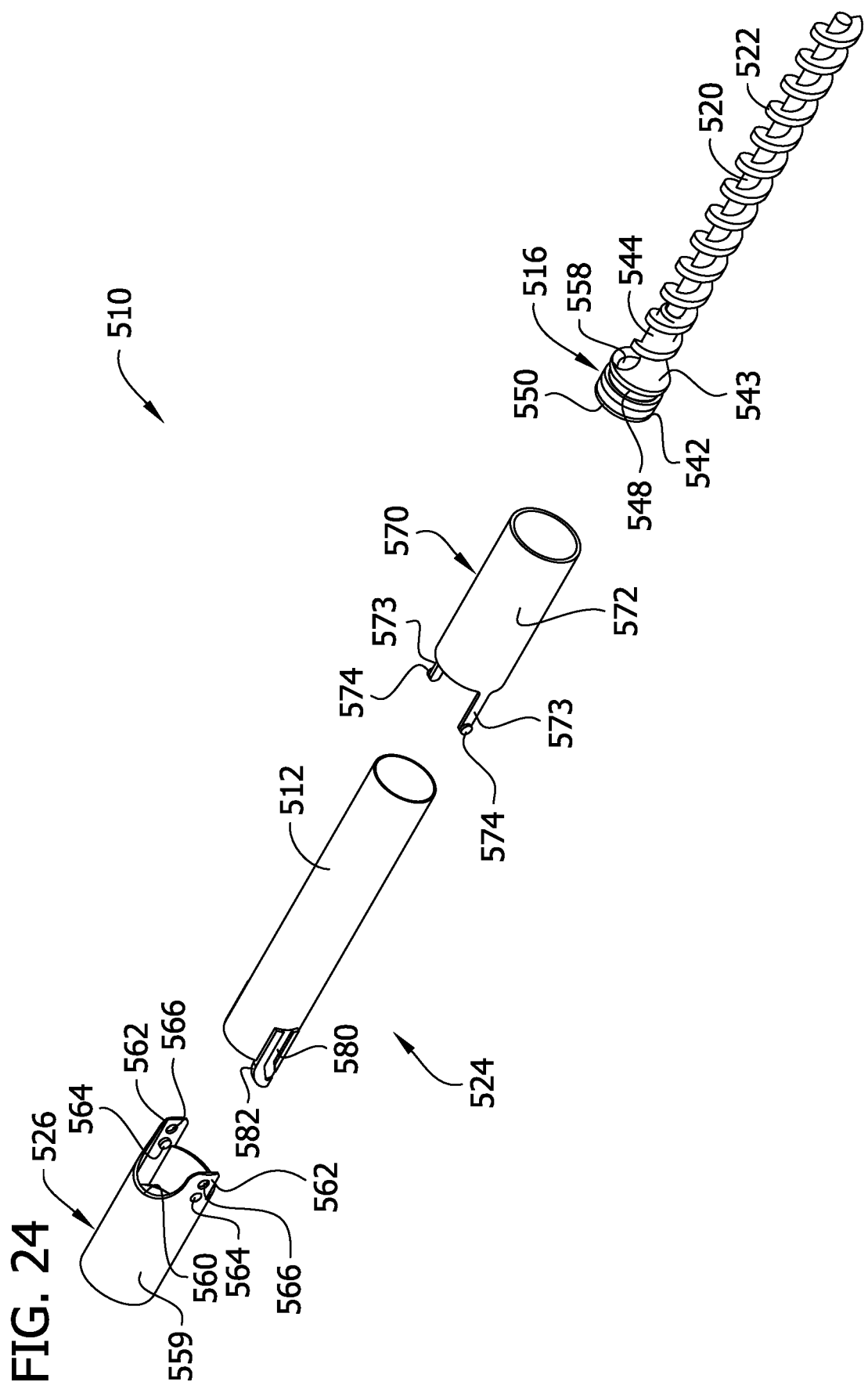
FIG. 24 is an enlarged exploded view of a distal end portion of the tissue-removing catheter of FIG. 23.
Figure 25:
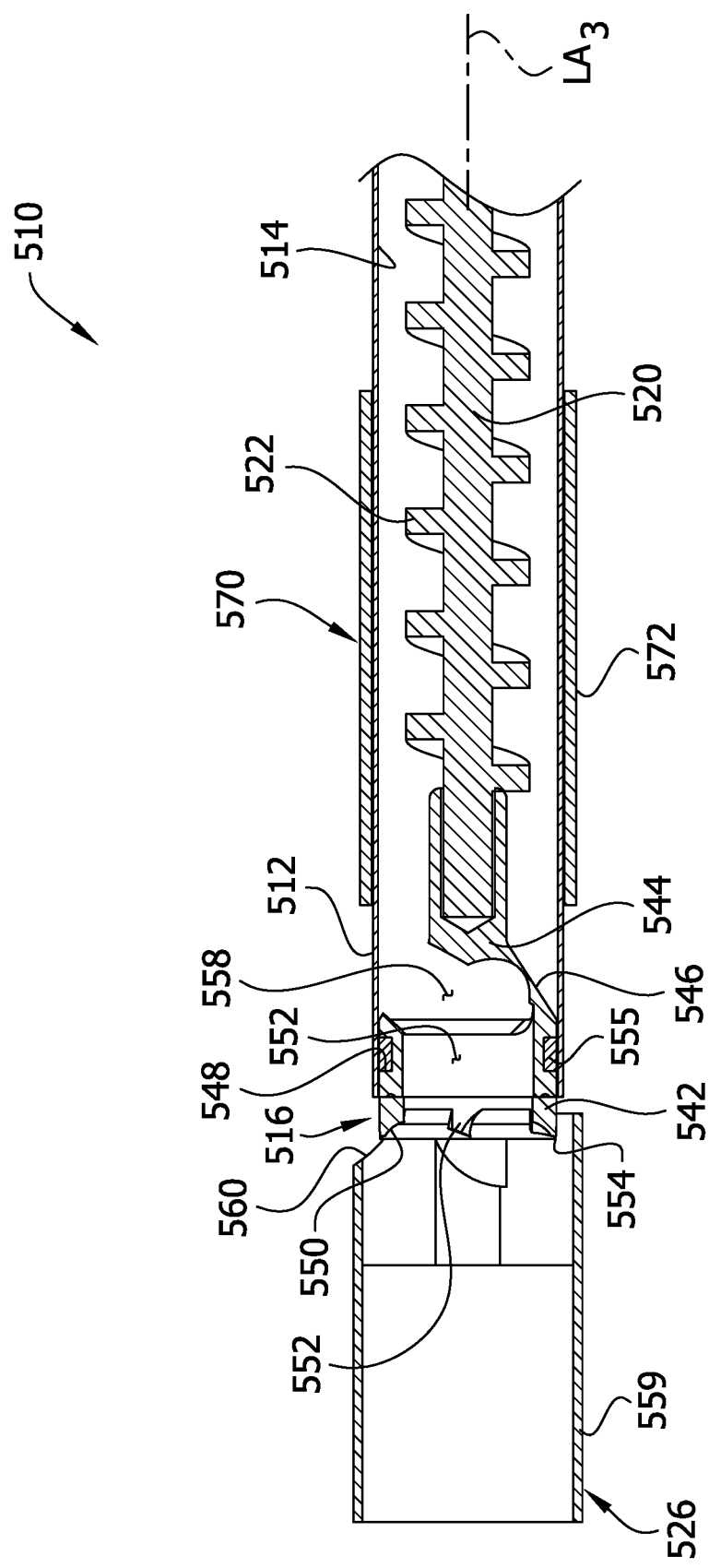
FIG. 25 is an enlarged longitudinal section of the distal end portion of the tissue-removing catheter of FIG. 23, including a cutter housing of the catheter in a closed position.
Figure 26:
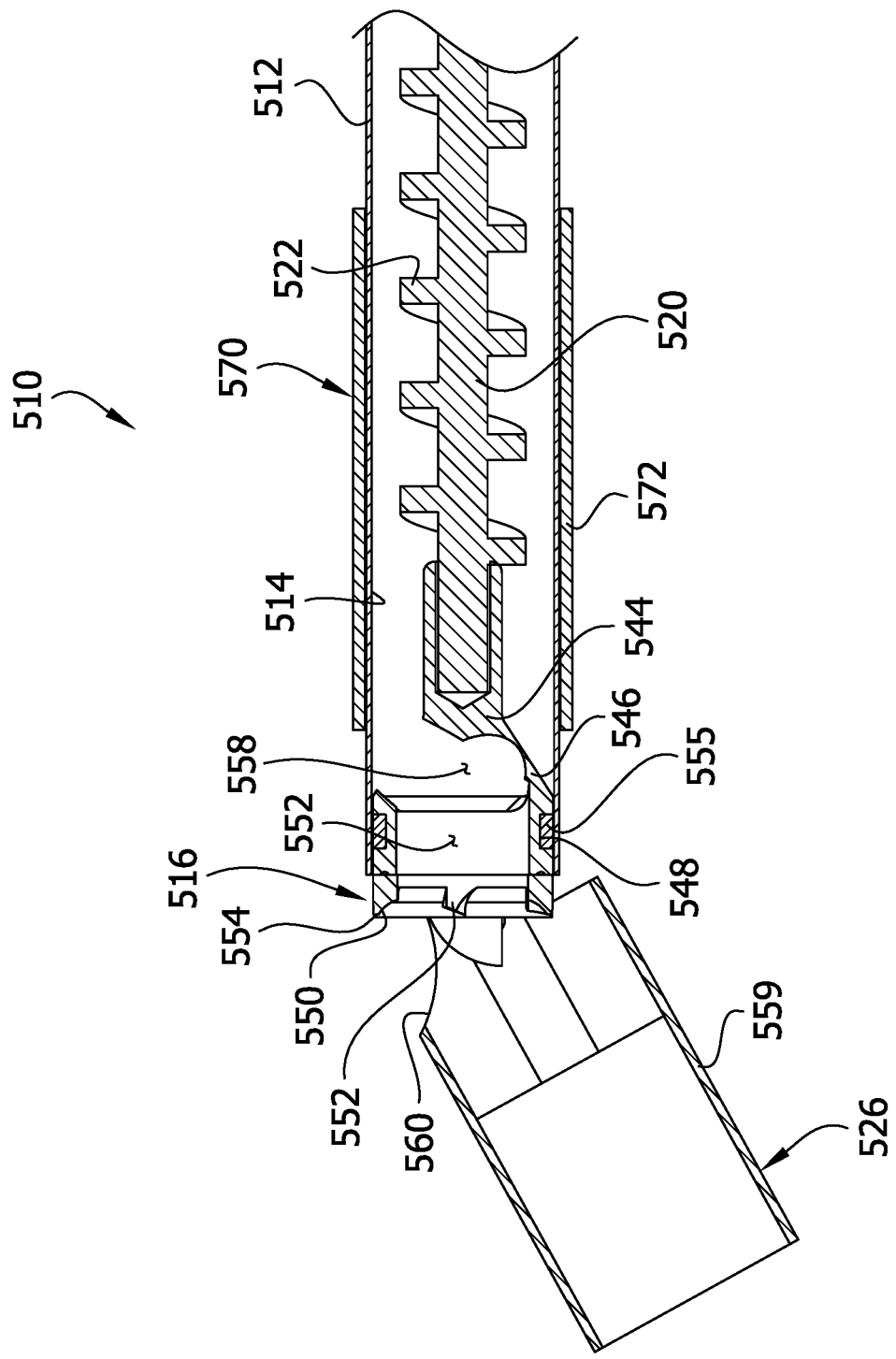
FIG. 26 is similar to FIG. 25, but with a cutter housing of the catheter in an open position.

Referring to FIGS. 23-28, a fifth embodiment of a tissue-removing catheter is generally indicated at 510. Briefly, the catheter 510 includes an elongate tubular catheter body 512 having opposite proximal and distal ends, a central longitudinal axis $LA_3$ (FIG. 25) extending between the distal and proximal ends, and an internal tissue-transport passage 514 (FIGS. 21 and 22) extending generally along the longitudinal axis of the body. The catheter body 512 may be similar to the catheter body 110 of the first catheter 110, and therefore, corresponding disclosure set forth with respect to catheter body of the first catheter is equally applicable to the present embodiment. Referring to FIGS. 24-26, a rotatable cutter, generally indicated at 516, is operatively connected to the distal end of the catheter body 512 for removing tissue from a body lumen. A driveshaft 520 (FIGS. 24-26), which includes an external helical thread 522, drives rotation of the cutter 516 and also transports or moves removed tissue proximally within the tissue-transport passage 514 of the catheter body 512. A deployment mechanism, generally indicated at 524, comprises a cutter housing 526 that is configurable between a closed position (FIGS. 23 and 25), in which the cutter 516 is not exposed for cutting, and an open position (FIGS. 26 and 28), in which the cutter is exposed for cutting.

Referring to FIGS. 24-26, as set forth above, the catheter 510 includes the rotatable cutter 516 and the driveshaft 520 for imparting rotation of the cutter. The driveshaft 520 extends along the tissue-transport passage 514 of the catheter body 512 and, in the illustrated embodiment, is substantially fixed axially with respect to the catheter body. A distal end portion of the driveshaft 520 is operatively connected to the rotatable cutter 516 for selectively driving rotation of the cutter generally about the longitudinal axis $LA_3$ of the catheter body 512. In the illustrated embodiment, the distal end portion of the driveshaft 520 is fixedly secured to the cutter 516. The shank of the driveshaft 520 (i.e., the part of the driveshaft not including the thread 522) is generally flexible and may be formed from one or more coils (e.g., stainless steel coil(s)), or a torque tube (e.g., a polyimide tube with a layer of braided stainless steel wire embedded therein). The shank of the driveshaft 520 may have a very high torsional stiffness and sufficient tensile strength, but which is generally laterally flexible. Depending upon the desired torque transmission, diameter and flexibility, any of a variety of other materials and constructions may also be used.

In the illustrated embodiment, the helical thread 522 on the exterior of the driveshaft 520 extends along the length of the driveshaft and functions as a transport mechanism for transporting removed tissue proximally within the tissue-transport passage 514 of the catheter body 512. Accordingly, the threaded driveshaft 520 functions as an auger or a screw conveyer, whereby rotation of the driveshaft imparts rotation of the helical thread 522, which moves removed tissue proximally within the catheter body 512. In the illustrated embodiment, the thread 522 is a right-handed thread (as viewed from the proximal end of the driveshaft 520), such that rotation of the driveshaft 520 clockwise (as viewed from the proximal end of the driveshaft 520) transports the tissue proximally. The tissue transport passage 514 and driveshaft thread 522 may extend back to the proximal end portion of the catheter body 512 and may empty into a tissue receptacle (not shown). The tissue transport passage 512 and driveshaft thread 522 may stop short of the proximal end portion of the catheter body 512. The thread 522 may be formed on the driveshaft 20 in a suitable manner.

Referring to FIG. 23, the proximal end of the driveshaft 520 is operably connected to a cutter motor 530 (broadly, a cutter driver) to impart rotation of the driveshaft 520 relative to catheter body 512. In one example, the cutter motor 530 is disposed within a handle 532 (shown with a cover removed in FIG. 23) that is releasably connectable to the proximal end of the catheter 510. For example, in addition to the cutter motor 530, the handle 532 may house a power source 534 (e.g., batteries) for the cutter motor 530, a microswitch (not shown) for activating cutter motor, and a catheter connector 536 for operatively connecting the motor to the proximal end portion of the driveshaft 520. In some embodiments, the cutter motor 30 can rotate the driveshaft 520 between 1,000 rpm and 10,000 rpm or more, if desired. As explained in more detail below, the handle 532 may include one or more input devices, such as lever 540, which controls operation of the cutter motor 530. It is understood that the driveshaft 520 may be driven in other ways without departing from the scope of the present invention.

As seen best in FIGS. 24-26, the rotatable cutter 516 has opposite proximal and distal ends and a longitudinal axis extending therebetween. The cutter 516 has a generally cylindrical distal cutting portion 542, a proximal stem 544 (broadly, a driveshaft-connection portion) for connecting the cutter to the driveshaft 524, and a transitional portion 546 intermediate the distal cutting portion and the stem. The distal cutting portion 542 of the cutter 516 includes an annular cutting edge 550 at the distal end thereof, and an axial cavity 552, defined by an interior surface of the cutter 516, extending from the cutting edge toward the stem 544 of the cutter. In one non-limiting example, the annular cutting edge 550 is beveled from an exterior surface of the cutter toward the interior surface to define a sharp, distal cutting edge 554. A plurality of raised element 556 (FIGS. 25 and 26) are also formed on the annular cutting edge 550, the details of which are disclosed in U.S. patent application Ser. No. 12/958,488, filed Dec. 2, 2010, the relevant teachings of which relating to the raised elements disclosed thereon are incorporated by reference herein, although the raised elements may be omitted. The exterior surface of the distal cutting portion 542 has a circumferential groove 548 formed therein in which bearing pins 555 on the interior surface of the catheter body 512 are received to allow the cutter 516 to rotate about its axis, while restricting axial movement of the cutter relative to the catheter body. It is understood that a separate bearing member (not shown) may be provided for the cutter 516. This bearing member would be considered part of the catheter body 522.

The cutter 516 has an eccentric opening 558 in communication with the axial cavity 552 to allow removed tissue to pass through the cutter. Together, the eccentric opening 558 and the axial cavity 552 define a tissue passage extending through the cutter 516. As can be seen from FIGS. 25 and 26, as the tissue is being removed, it enters the axial cavity 552, and then passes through the eccentric opening 558 and into the tissue-transport passage 514, where it can be picked up by the driveshaft thread 522 (or other transport mechanism), and transported proximally within the catheter body 512. The eccentric opening 558 in the cutter 516 is offset with respect to the longitudinal axis (and rotational axis) of the cutter.

The cutter 516 may be formed as a single, one-piece construction, or may be formed from separate components secured to one another in a suitable manner, such as welding, soldering, adhesives, mechanical interference fit, threaded engagement and the like. As a non-limiting example, the cutter 516 may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, electro-discharge machining (EDM), laser cutting, heat treating, precipitation hardening, casting or other methods. The cutter 516 may be of other configurations without departing from the scope of the present invention.

As set forth above, the deployment mechanism 524 includes a cutter housing 526 that opens to expose the cutter 516, and closes to cover the cutter. As shown best in FIG. 24, the cutter housing 526 includes a generally cylindrical housing body 559, a cutter window 560, and links or housing arms 562 (e.g., two arms) extending longitudinally outward from a proximal end of the housing body. For reasons explained below, each housing arm 562 includes an inner pin 564 extending inward toward the opposite housing arm and a pin opening 566 disposed proximal of the corresponding pin. The cutter housing 526 is operatively connected to a longitudinal force-transmitting member, generally indicated at 570, for imparting movement of the cutter housing between its open and closed positions. The force-transmitting member 570 includes a sleeve 572 slidably fitted over the catheter body 512, and slide arms 573—which include pivot pins 574 rotatable received in the respective pin openings 566, as explained below—extending longitudinally outward from the distal end of the sleeve. Although in the drawings the sleeve 572 is illustrated as having a proximal end that terminates distal of the handle, the sleeve is operatively connected to the handle 532 (e.g., the sleeve may extend to the handle) for imparting longitudinal movement of the sleeve relative to the catheter body 512 and the cutter 516. In particular, in the illustrated embodiment (FIG. 1) the sleeve 572 is operatively connected to an actuator 576 (e.g., a lever) on the handle 532 for imparting longitudinal movement of the sleeve. For example, movement of the lever 576 proximally imparts proximal movement of the sleeve 572, and movement of the lever distally imparts distal movement of the sleeve. It is understood that the force-transmitting member 570 may be of other configurations.

Figure 27:
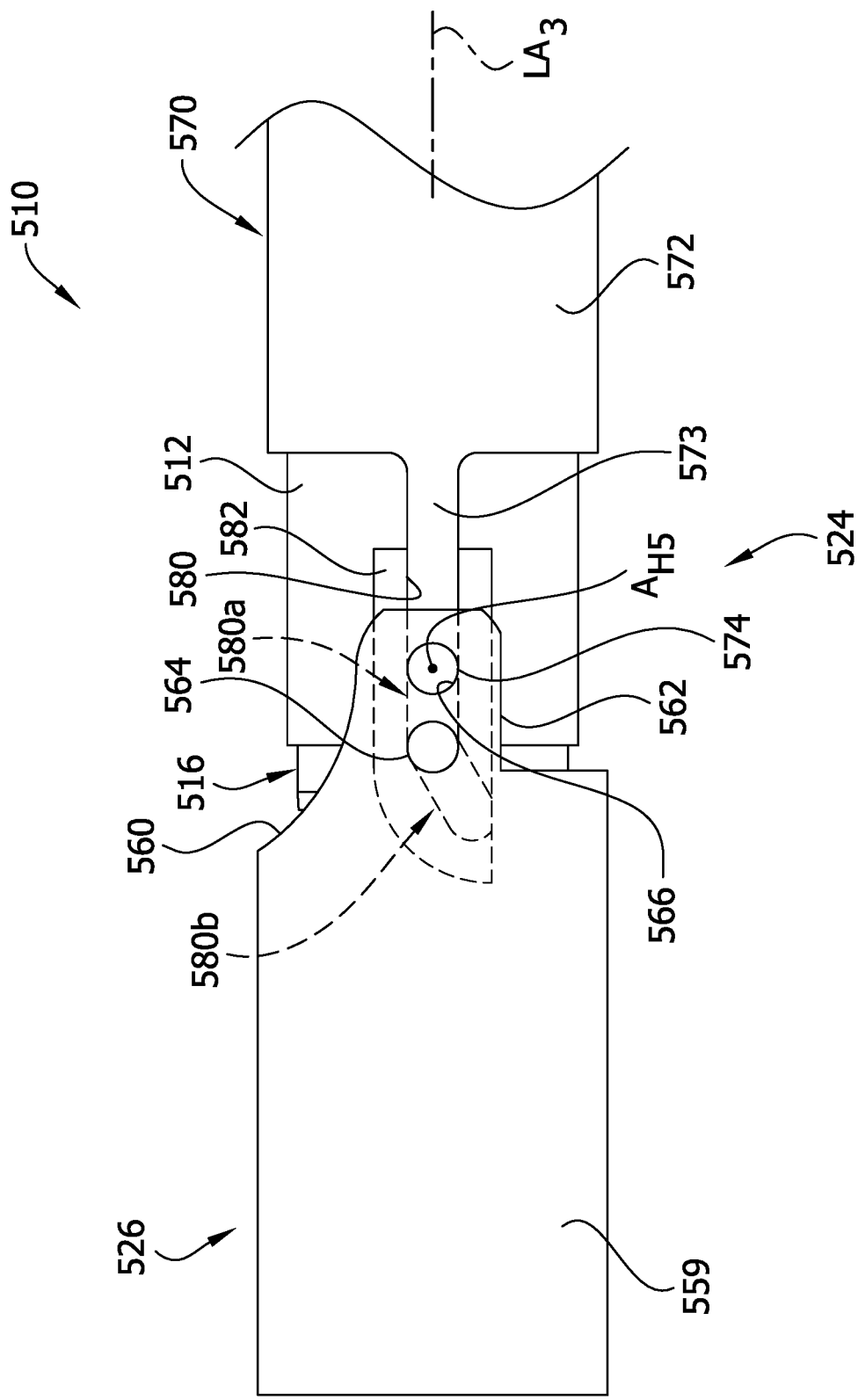
FIG. 27 is an enlarged, side elevation of a distal end portion of the tissue-removing catheter, the cutter housing being in the closed position.
Figure 28:
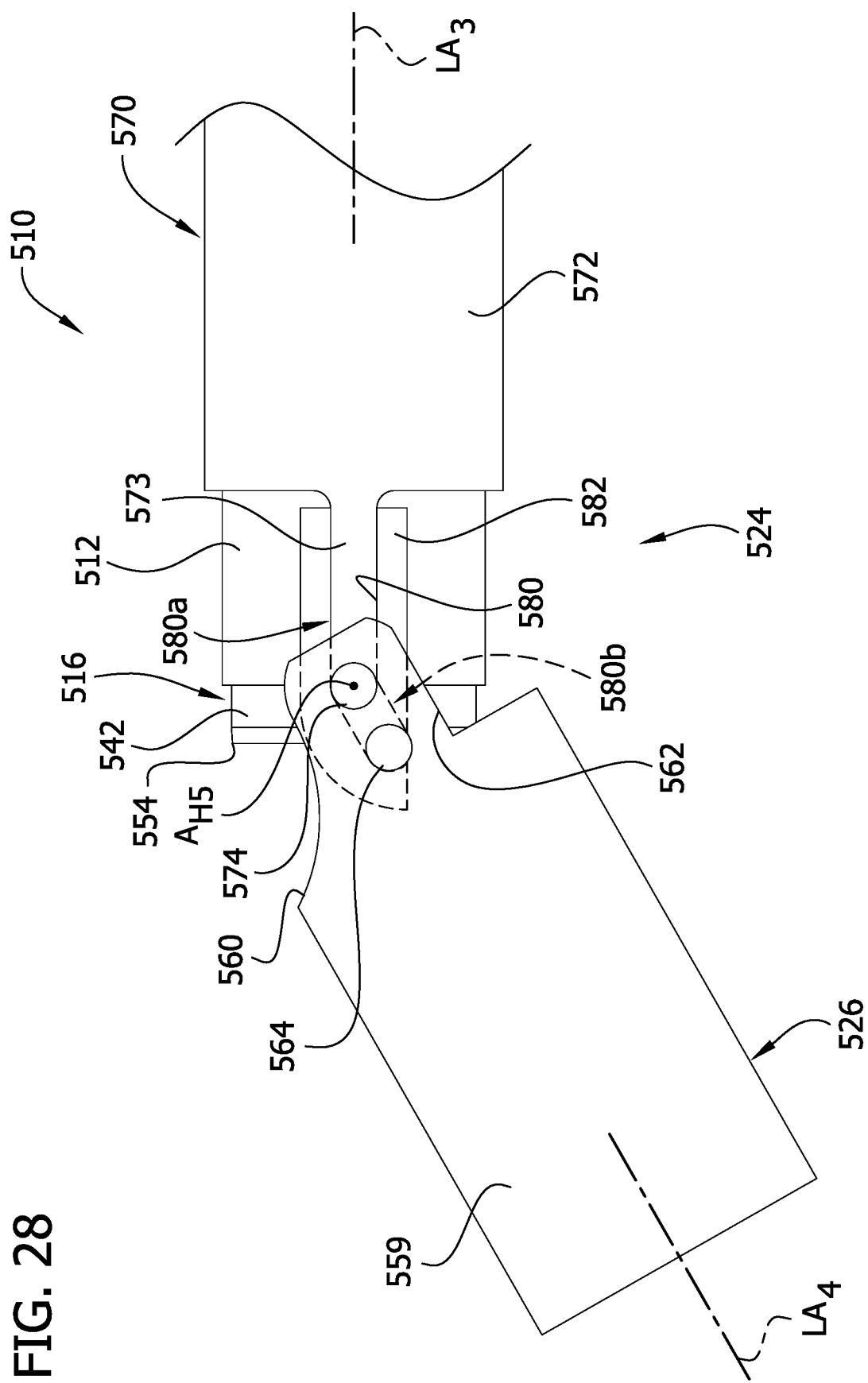
FIG. 28 is similar to FIG. 27, but with the cutter housing in the open position.

As shown best in FIGS. 24, 27, and 28, the housing pins 564 and the slide arms 573 are slidably received in slots 580 defined by corresponding tracks 582 secured adjacent to and extending longitudinally outward from the distal end of the catheter body 512. Only one track 582 is visible in FIGS. 24, 27, and 28, with the other track being generally diametrically opposite the visible track and substantially identical. As shown in FIGS. 27 and 28, the slot 580 has a proximal portion, generally indicated at 580a, extending generally longitudinally relative to the catheter body 512, and a distal portion, generally indicated at 580b, extending at an angle offset from the proximal portion and the longitudinal axis of the catheter body. The corresponding slide arm 573 is slidably translatable in the proximal portion 580a for generally longitudinal movement therein. The slide arm 573 is generally not slidably translatable in the distal portion 580b. The corresponding housing pin 564 is slidably translatable in the distal portion 580b and may be slidably translatable in the proximal portion 580b, although this is not necessary.

As shown in FIG. 27, when the cutter housing 526 is in its closed position, each housing pin 564 is substantially aligned longitudinally, with respect to the catheter body 512, with the corresponding pivot pin 574 associated with the same housing arm 562. In this closed position, the lever 576 of the illustrated embodiment is in the proximal position. To open the cutter housing 526, the longitudinal force-transmitting member 570 is moved distally, such as by moving the lever 576 on the handle 532 distally. As the longitudinal force-transmitting member 570 moves distally, each slide arm 573 slides distally within the corresponding track 582 and imparts distal movement of the cutter housing 526 by virtue of connection of the pivot pins 574 with the corresponding housing arms 562 of the cutter housing. As the cutter housing 526 moves distally, the housing pins 564 track along the distal portions 580b of the respective track slots 580, while simultaneously, the cutter housing pivots or rotates about the pivot pins 574 on the slide arms 573 of the force-transmitting member 570. In effect, the cutter housing 526 rotates away from the cutter 516 about a hinge axis $A_5$ extending through the pins 574, such that a longitudinal axis $LA_4$ of the cutter housing extends at an offset angle relative to the longitudinal axis $LA_3$ of the catheter body 512 (FIG. 28). This offset angle may measure from about 15 degrees to about 45 degrees, or from about 20 degrees to about 30 degrees. With the cutter housing extending at the offset angle, a portion of the cutting edge is exposed through the cutter window 560, as shown in FIGS. 26 and 28. To close the cutter housing 526, the longitudinal force-transmitting member 570 is moved proximally, such as by moving the lever 576 proximally, whereby the pins 564 track proximally in the distal portions 580b of the slots 580 and the pins 574 track proximally in the proximal portions 580a of the slots to impart rotation of the cutter housing toward the cutter 516 about the hinge axis $A_{H5}$.

An exemplary use of the catheter 510 may be similar to the exemplary uses of the first catheter 110 set forth above, with the exception being that the cutter housing 518 is opened and closed by longitudinally moving the force-transmitting member 570, as set forth above.

Figure 29:
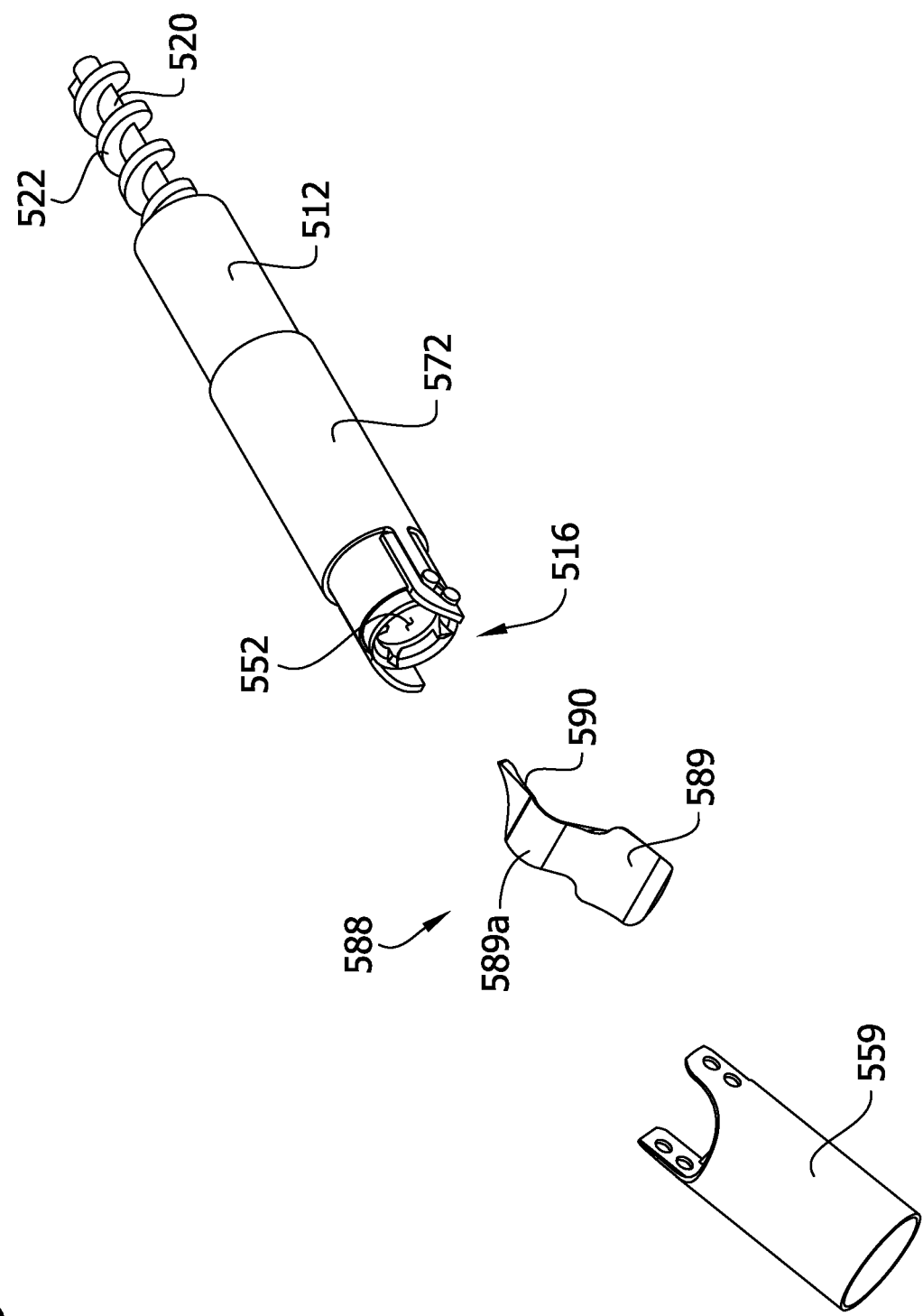
FIG. 29 is an exploded perspective view of the tissue-removing catheter of the fifth embodiment, but further including a tissue director.
Figure 30:
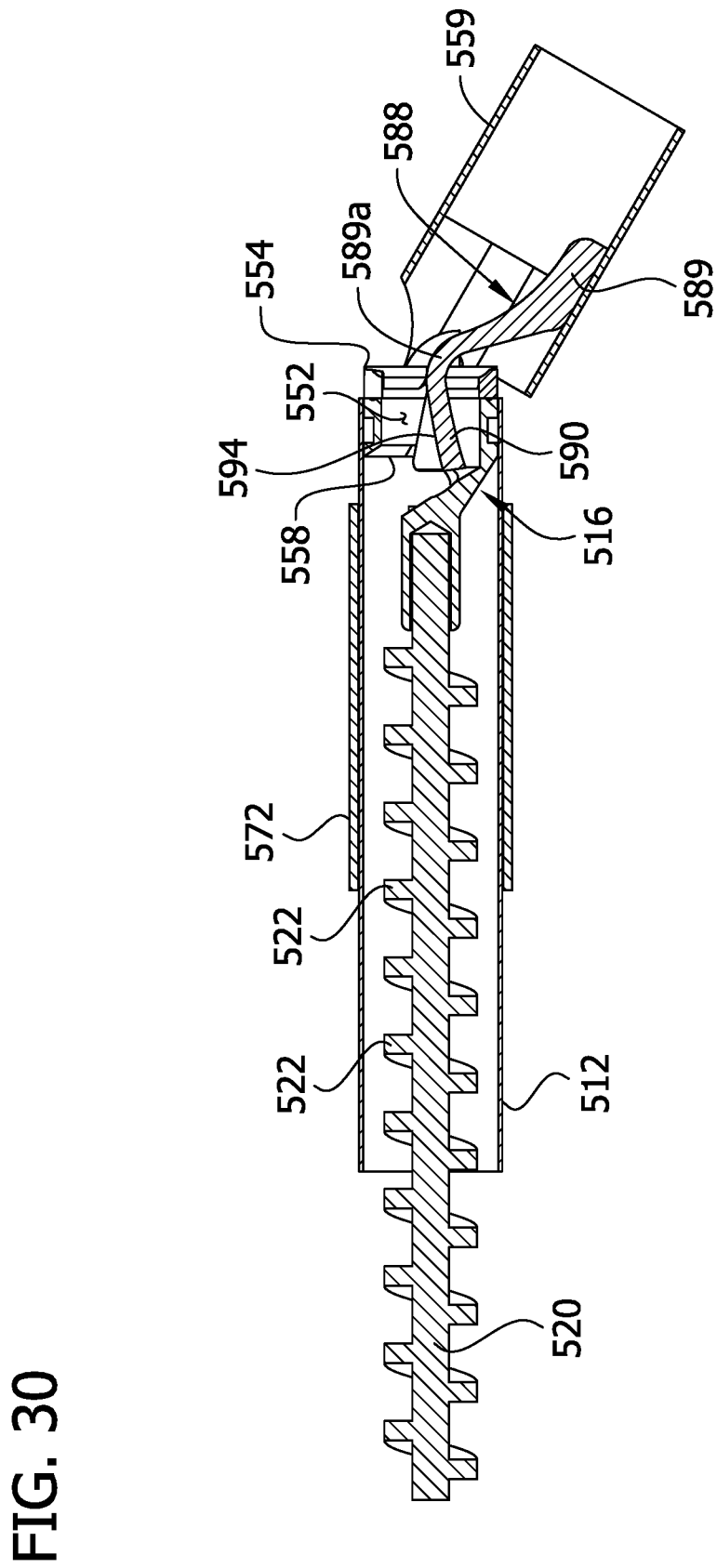
FIG. 30 is an enlarged longitudinal section of the distal end portion of the tissue-removing catheter of FIG. 29, including a cutter housing in an open position.

Referring to FIGS. 29 and 30, in one example the catheter 510 may further include a tissue director, generally indicated at 588, for directing tissue removed by the cutter 516 proximally within the axial cavity 552 of the cutter. The illustrated tissue director 588 is also configured for directing removed tissue circumferentially relative to axial cavity 552 toward the eccentric opening 558 (FIG. 30) to facilitate movement of the removed tissue through the cutter 516 where the removed tissue can be picked up by the helical thread 522. Although the illustrated tissue director 588 is associated with the catheter 510, it is understood that the tissue director may be incorporated in a different catheter having a deflectable distal tip or other deployment mechanism and a cutter that allows removed tissue to pass therethrough.

Figure 31:
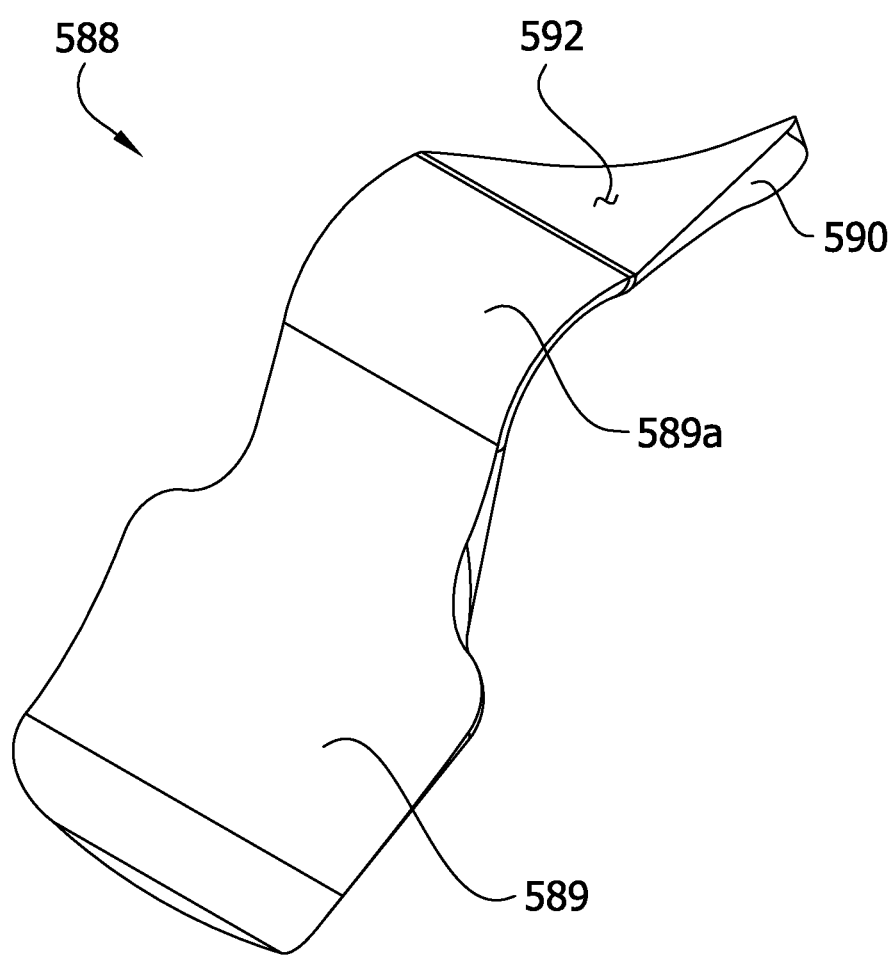
FIG. 31 is an enlarged perspective of the tissue director.

Referring to FIG. 30, the tissue director 588 includes a distal tongue portion 589 attached within the housing body 559 (or other deflectable distal tip member), and a proximal flute portion 590 extending proximally from the tongue portion and received in the axial cavity 552 of the cutter 516. The flute portion 590 is free from attachment to the cutter 516 so that the cutter 516 is rotatable about the flute portion. The flute portion 590 has a length $L_F$ (FIG. 32) extending generally axially within the axial cavity 552 from adjacent the distal tip 554 of the cutter 516 to adjacent the eccentric opening 558 (FIG. 30), and a width $W_F$ (FIG. 33) extending generally across the axial cavity (e.g., diametrically across the axial cavity). As shown best in FIGS. 31 and 32, the flute portion 590 defines a groove or fluting 592 extending along the length $L_F$ of the flute portion. The fluting 592 extends along a counterclockwise or left-handed helical path as viewed from the distal end of the catheter 510, and in the illustrated embodiment, the direction of the helical path of the fluting (e.g., counterclockwise direction) is the same as the direction that the cutter 516 rotates (e.g., counterclockwise).

Figure 32:
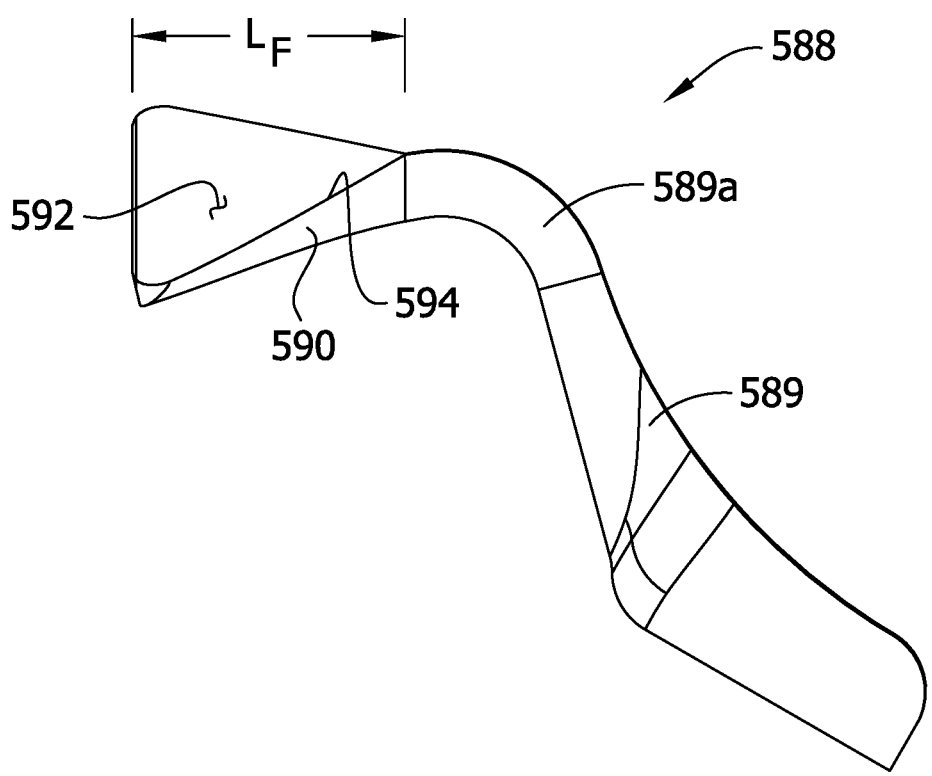
FIG. 32 is an enlarged left side elevational view of the tissue director.
Figure 33:
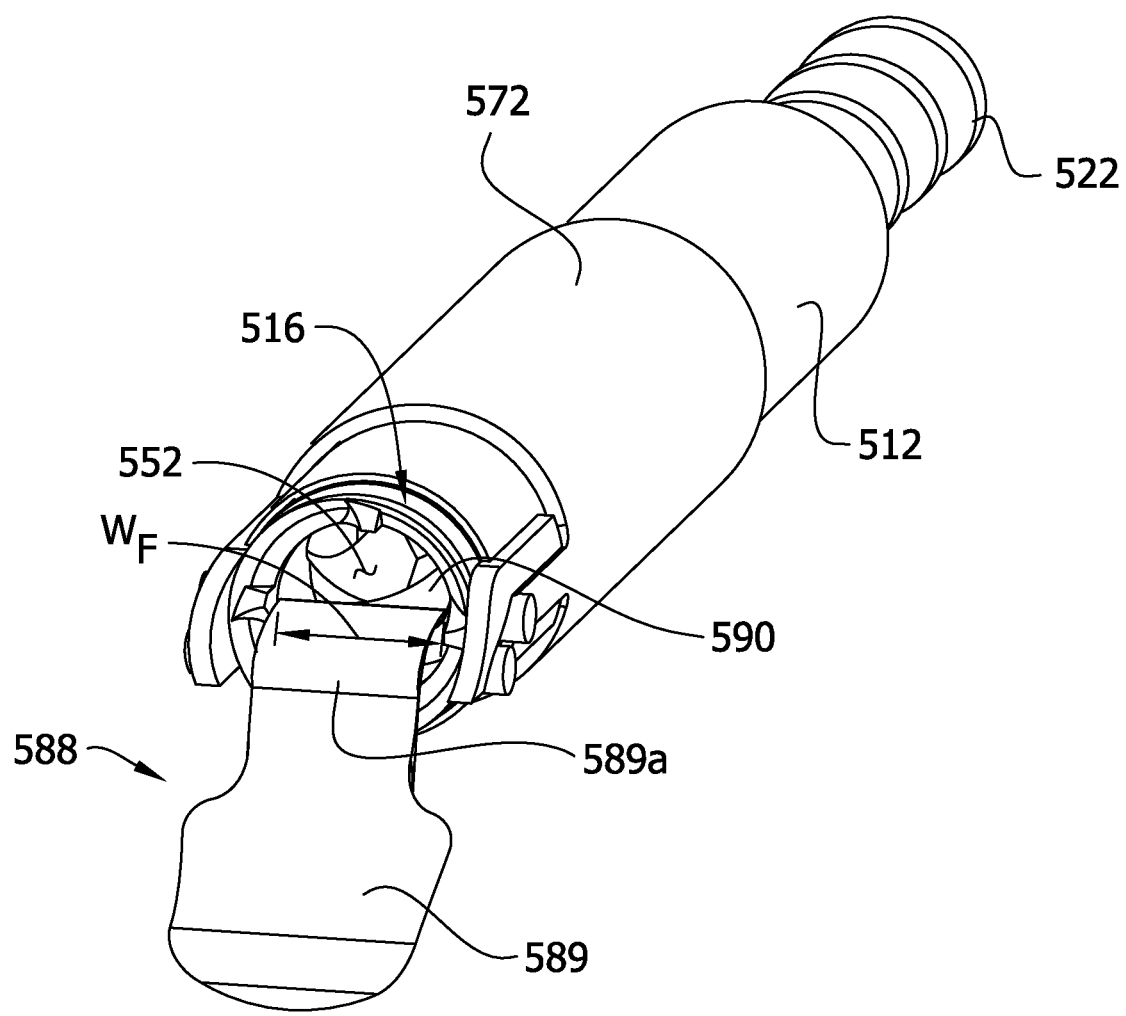
FIG. 33 is a perspective view of the tissue-removing catheter of FIG. 29, with the cutter housing removed.

As shown in FIG. 30, when the housing body 559 is open, the tongue portion 589 has a bend or curve 589a. When the housing body 559 is closed, the tongue portion 589 may straighten or buckle or otherwise be configured in a shape that allows the tissue director 588 to fit within the axial cavity 552 of the cutter 516. Accordingly, the tissue director 588 may be flexible along its length $L_F$, and in one embodiment, the tissue director is resiliently deflectable along its length and biased in the illustrated shape when the housing body 559 is open to properly position the flute portion 590 in the axial cavity, as shown in FIG. 30. As shown in FIGS. 30 and 32, when the housing body 559 is open, a leading longitudinal edge 594 of the flute portion gradually falls away from (i.e., slopes radially away from) the rotational axis of the cutter 516 and toward the interior wall defining the axial cavity 552. As tissue is removed by the rotating cutter 516, the flute portion 590 directs the removed tissue both circumferentially and proximally within the axial cavity 552 to inhibit the removed tissue from passing back through the open distal end 554 of the cutter.

Figure 34:
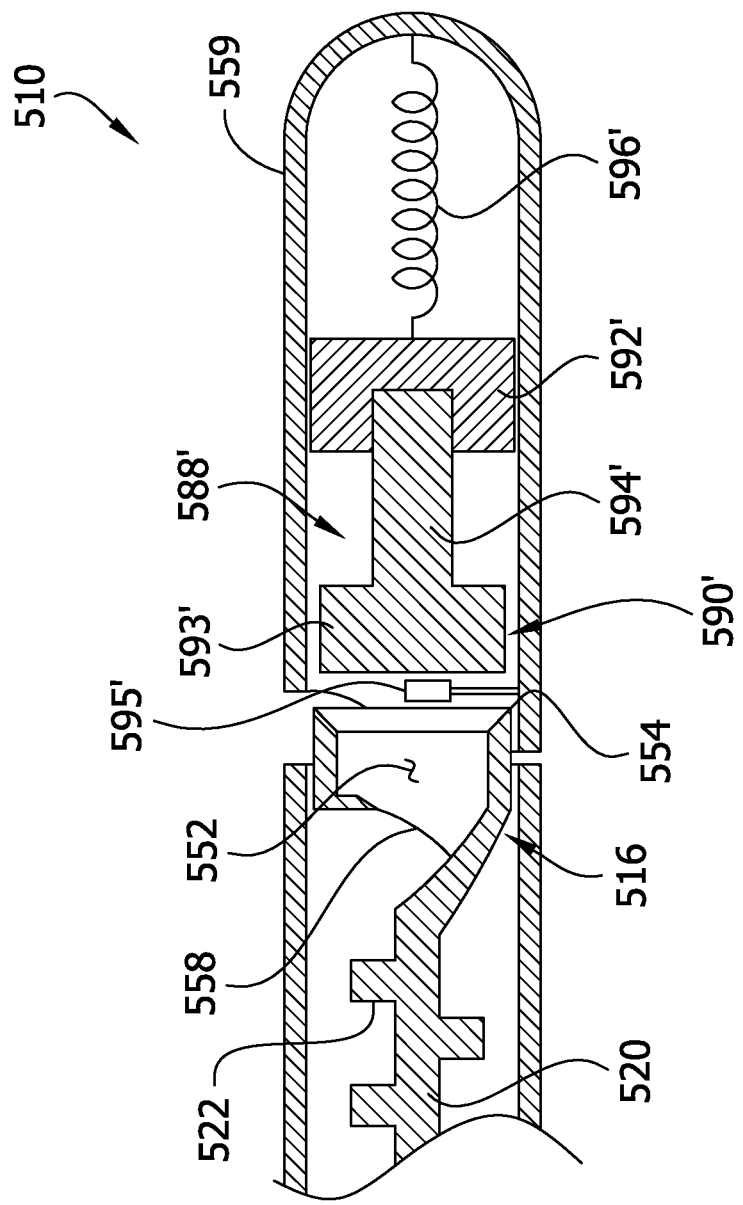
FIG. 34 is an enlarged longitudinal section of a distal end portion of of the tissue-removing catheter of the fifth embodiment, but further including another example of a tissue director, the cutter housing being in a closed position.
Figure 35:
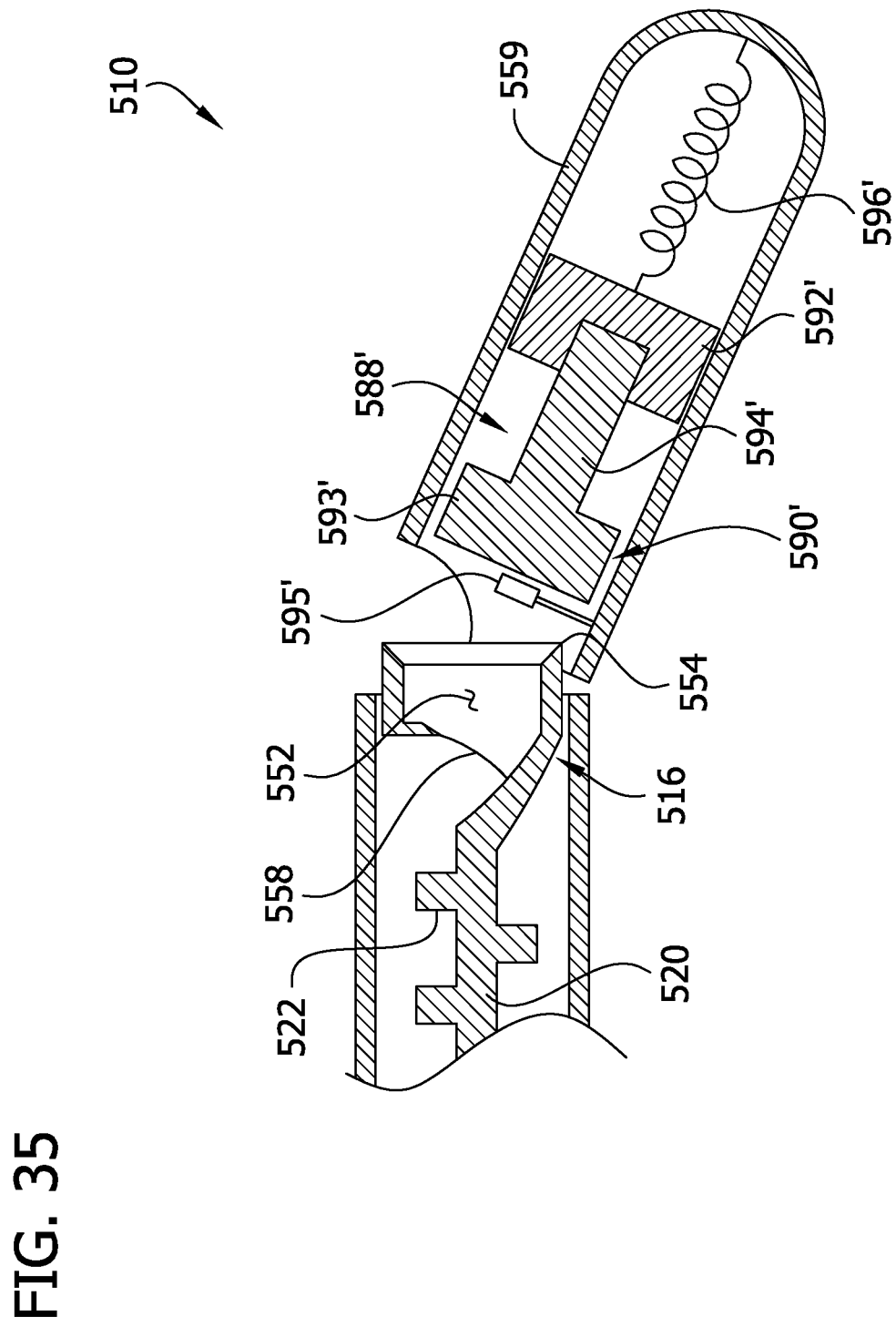
FIG. 35 is similar to FIG. 34, but with the cutter housing being in an open position.

Referring to FIGS. 34 and 35, another example of a tissue director, generally indicated at 588', is incorporated in the catheter 510 and is configured for directing tissue removed by the cutter 516 proximally toward the cutter and into the axial cavity 552 of the cutter. Although the Illustrated tissue director 588' is associated with the catheter 510, it is understood that the tissue director may be incorporated in a different catheter having a deflectable distal tip or other deployment mechanism. The tissue director 588' includes a rotatable tissue-directing member, generally indicated at 590', and a bearing member 592'. The tissue-directing member 590' includes a proximal head 593' located distal of and in opposing relationship with the cutter 516, and a stem 594' that is rotatably coupled to the bearing member 592' for rotation about its axis. The head 593' is generally disk-shaped and is operatively coupled to the cutter 516 so that rotation of the cutter drives rotation of the tissue director 590'. A face of the head 593' faces proximally and may have a shape or contour to facilitate directing removed tissue toward the cutter 516 as the head 593' rotates. In the illustrated embodiment, the head 593' is coupled to the cutter 516 by gearing 595'. In particular, the cutter 516 may include a gear (e.g., teeth) extending circumferentially adjacent the distal tip 554 and in engagement with the gearing 595', and the head 593' may also include a gear (e.g., teeth) extending circumferentially adjacent its proximal end and in engagement with the gearing 595'. In one embodiment, the gearing 595' is configured to counter-rotate the head 593' in a direction opposite that of the cutter 516. In another embodiment, which may not include the gearing 595', the head 593' may rotate in the same direction as the cutter 516. In another embodiment, the head 593' may be directly coupled to the cutter 516, such as by bringing the gears of the two components in engagement with one another.

In the illustrated embodiment, the bearing member 592' is movable longitudinally within the cutter housing body 559. In this embodiment, the tissue director 588' also includes a biasing member 596' (e.g., a spring) for biasing the bearing member 592' and/or the head 593', toward the cutter 516 to maintain the mechanical coupling between the cutter and the head 593' (e.g., maintain the engagement between the gearing 595' and the cutter and the head) when the cutter housing body 559 is open (FIG. 35). In another embodiment, the bearing member 596' and the head 593' may be fixed longitudinally within the cutter housing body 559 and positioned so that the bearing member head 593' couples to the cutter 516 when the cutter housing is open.

Figure 36:
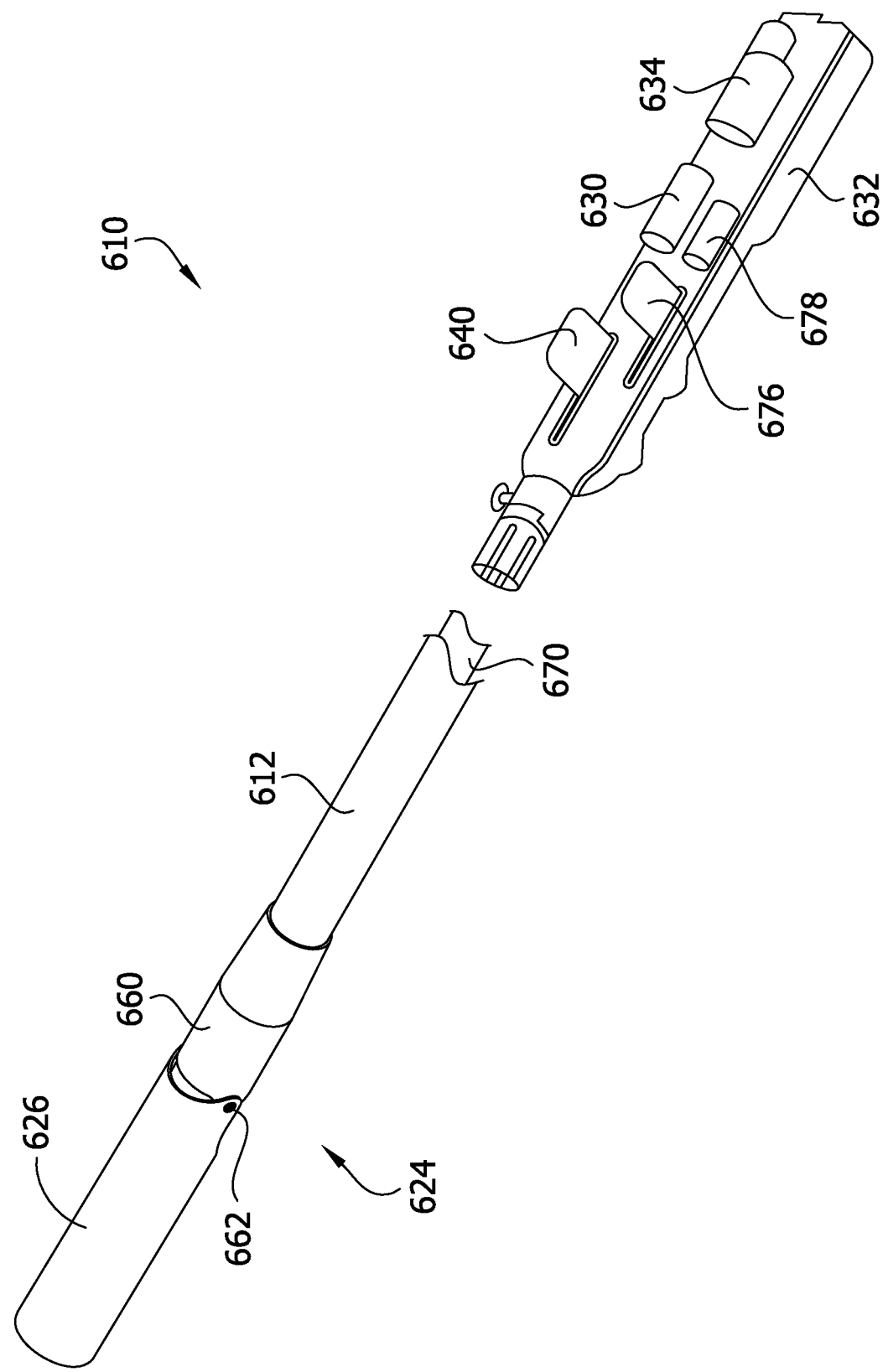
FIG. 36 is a fragmentary perspective of a sixth embodiment of a tissue-removing catheter, including a removable handle attachable to a proximal end of the catheter.
Figure 37:
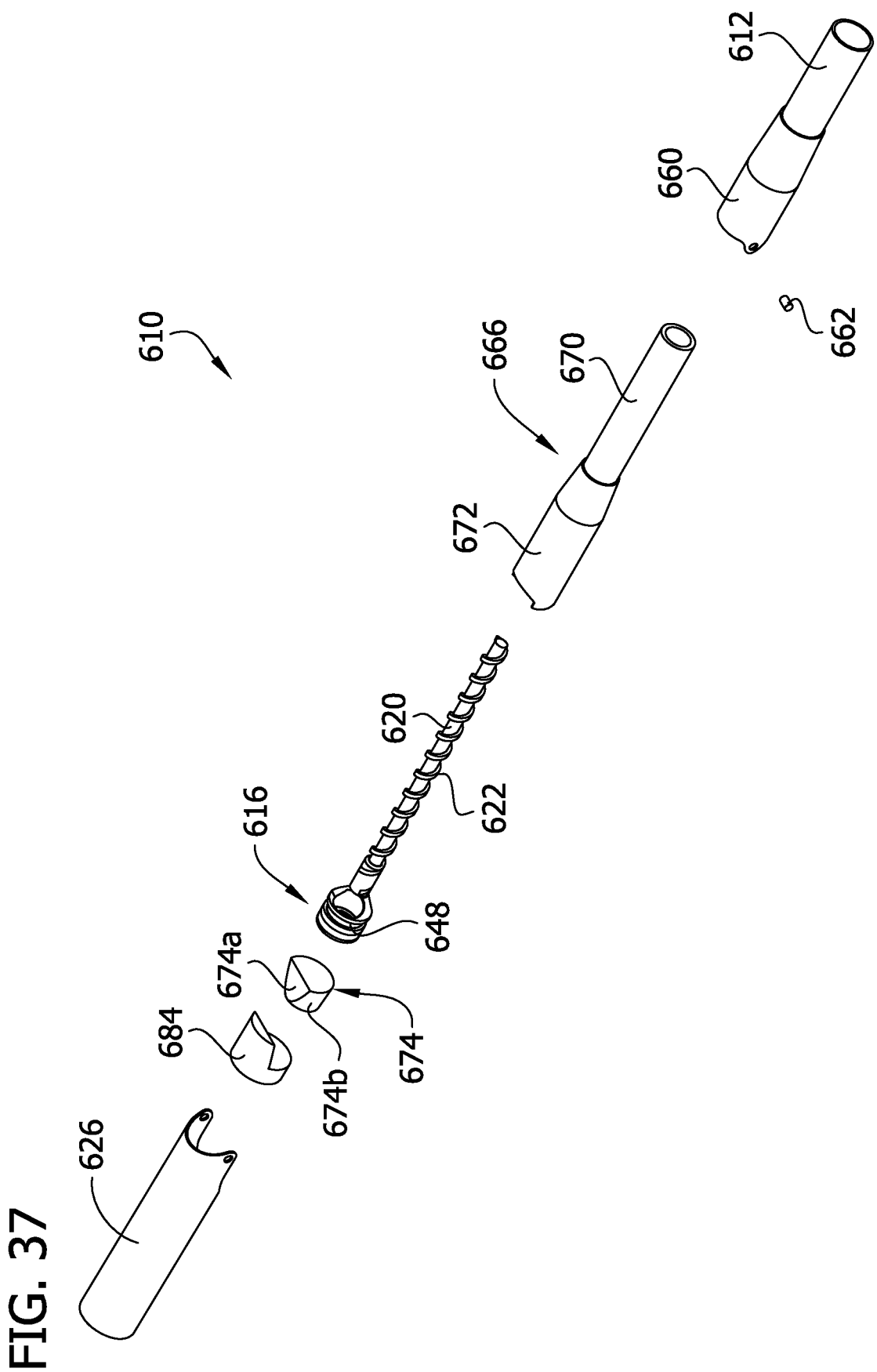
FIG. 37 is an exploded view of the tissue-removing catheter of FIG. 36.
Figure 38:
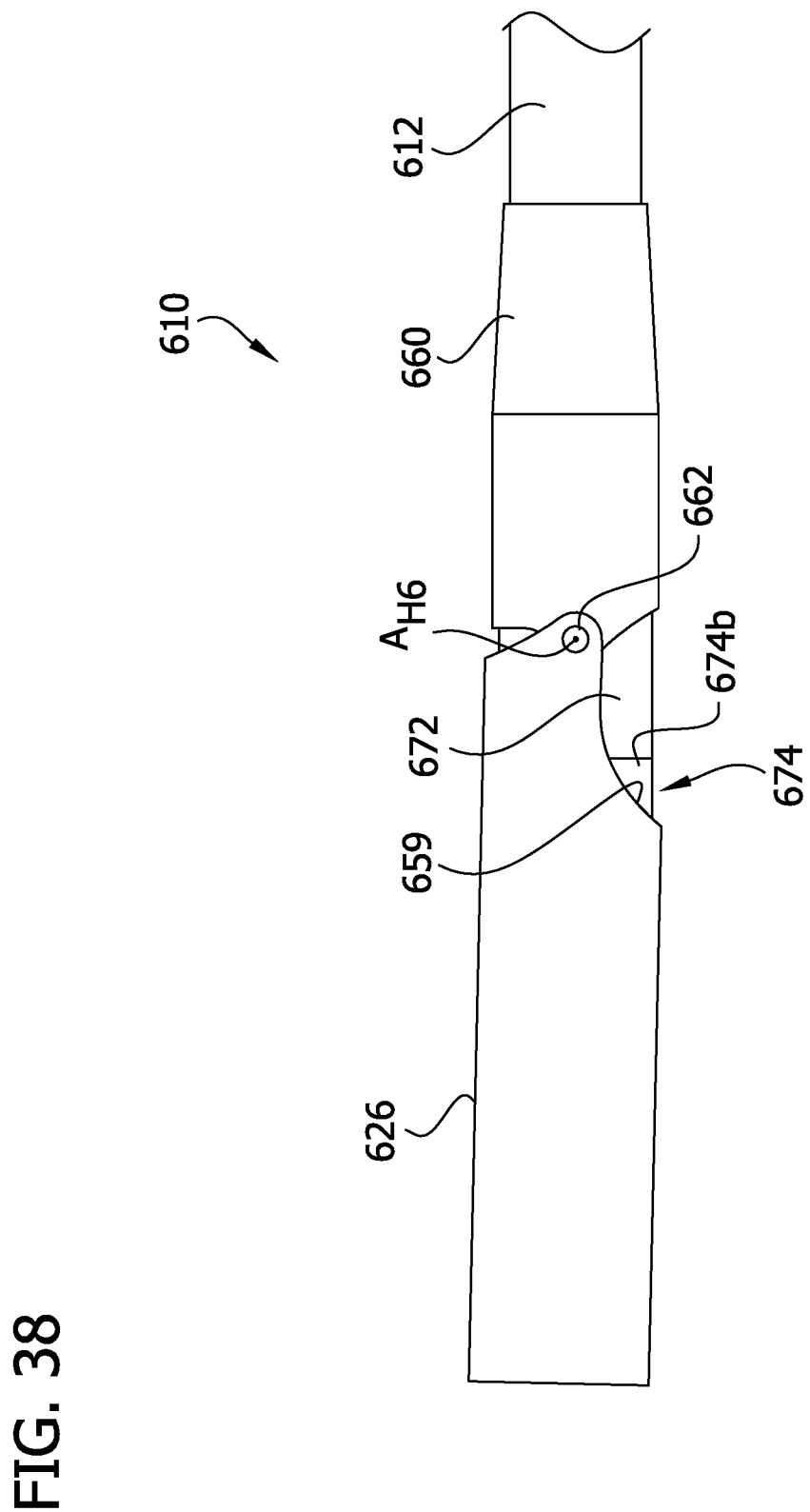
FIG. 38 is an enlarged, side elevation of a distal end portion of the tissue-removing catheter of FIG. 36, the cutter housing being in the closed position.
Figure 39:
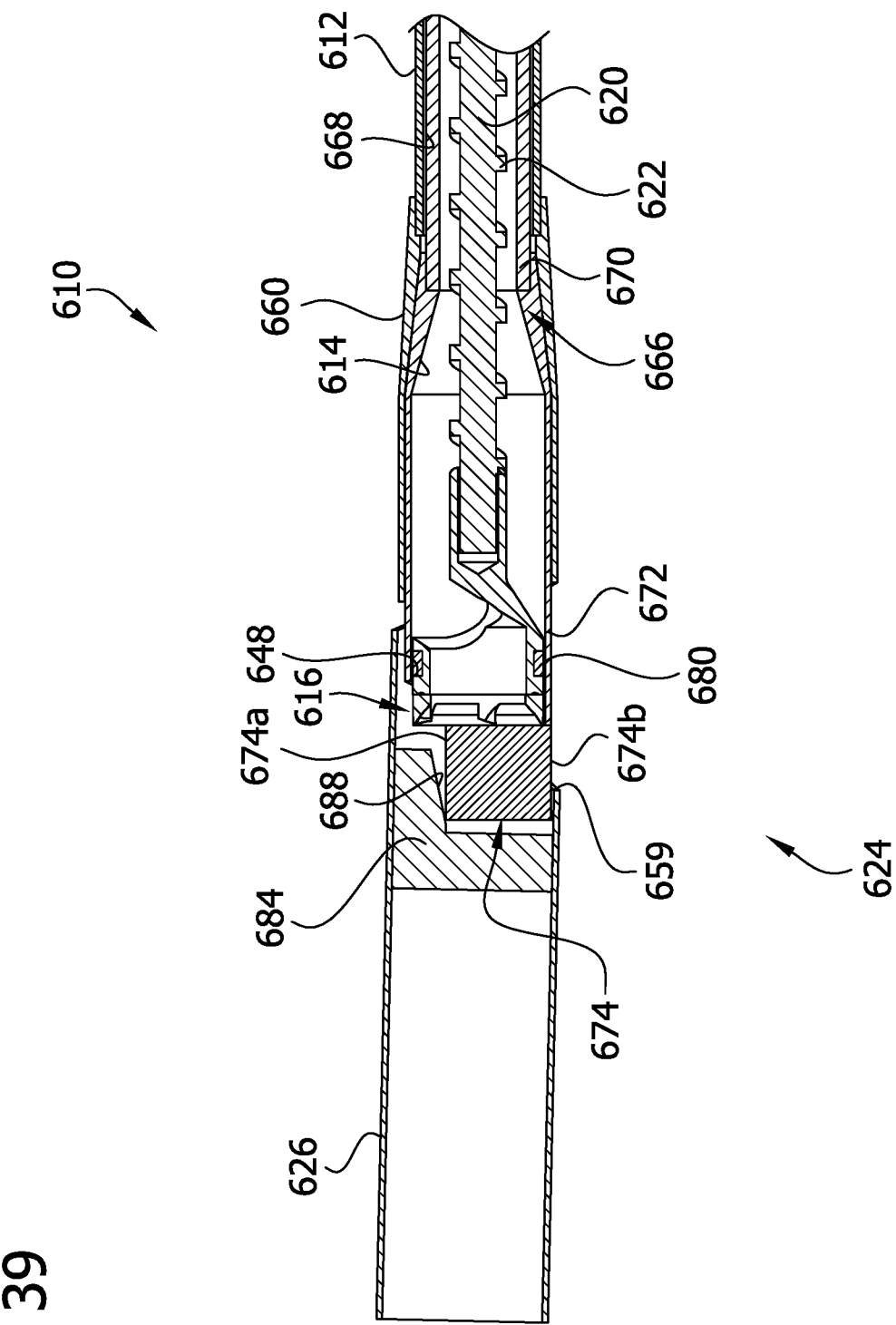
FIG. 39 is a longitudinal section of the catheter of FIG. 38.
Figure 40:
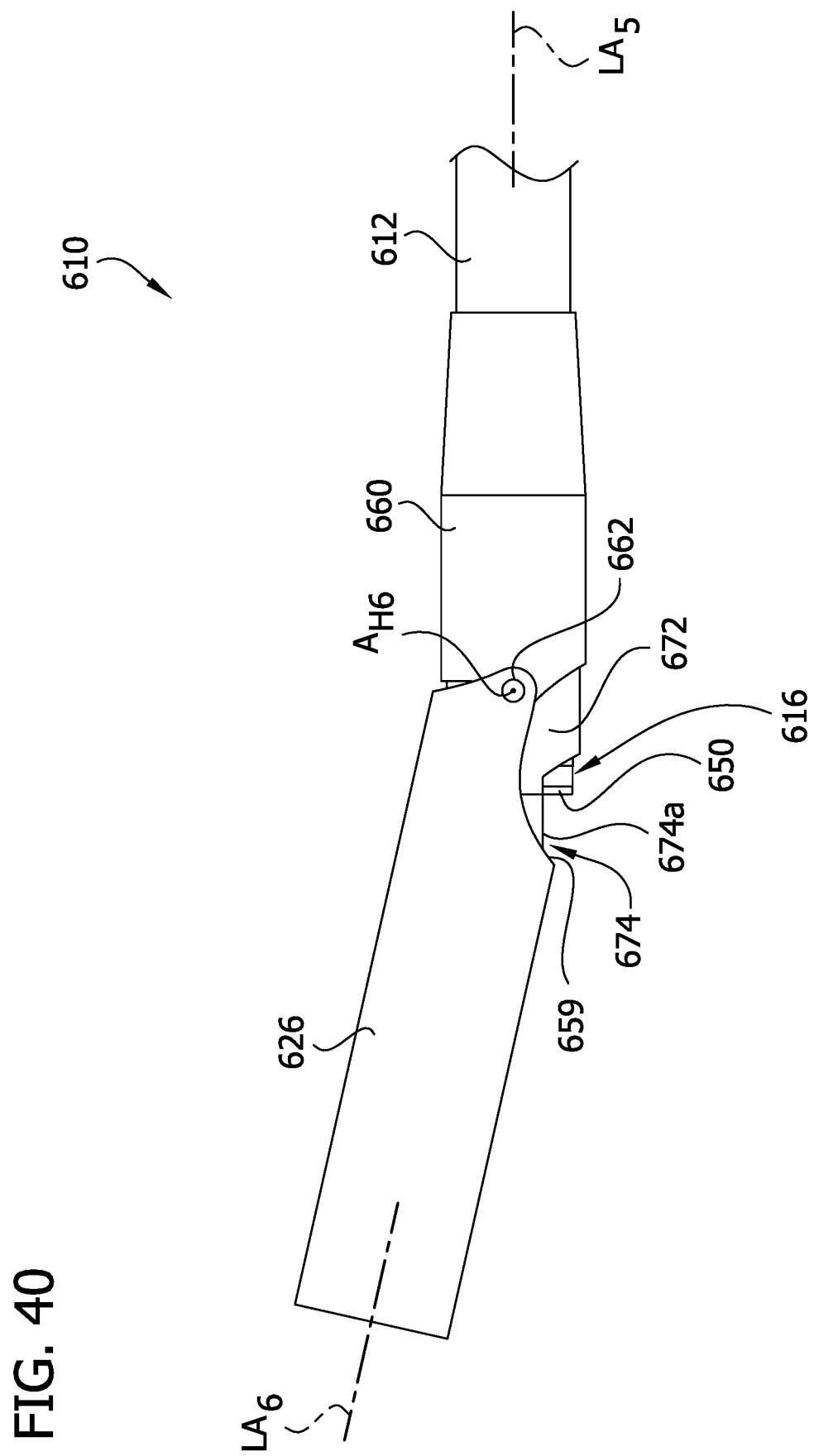
FIG. 40 is similar to FIG. 38, but with the cutter housing in the open position.
Figure 41:
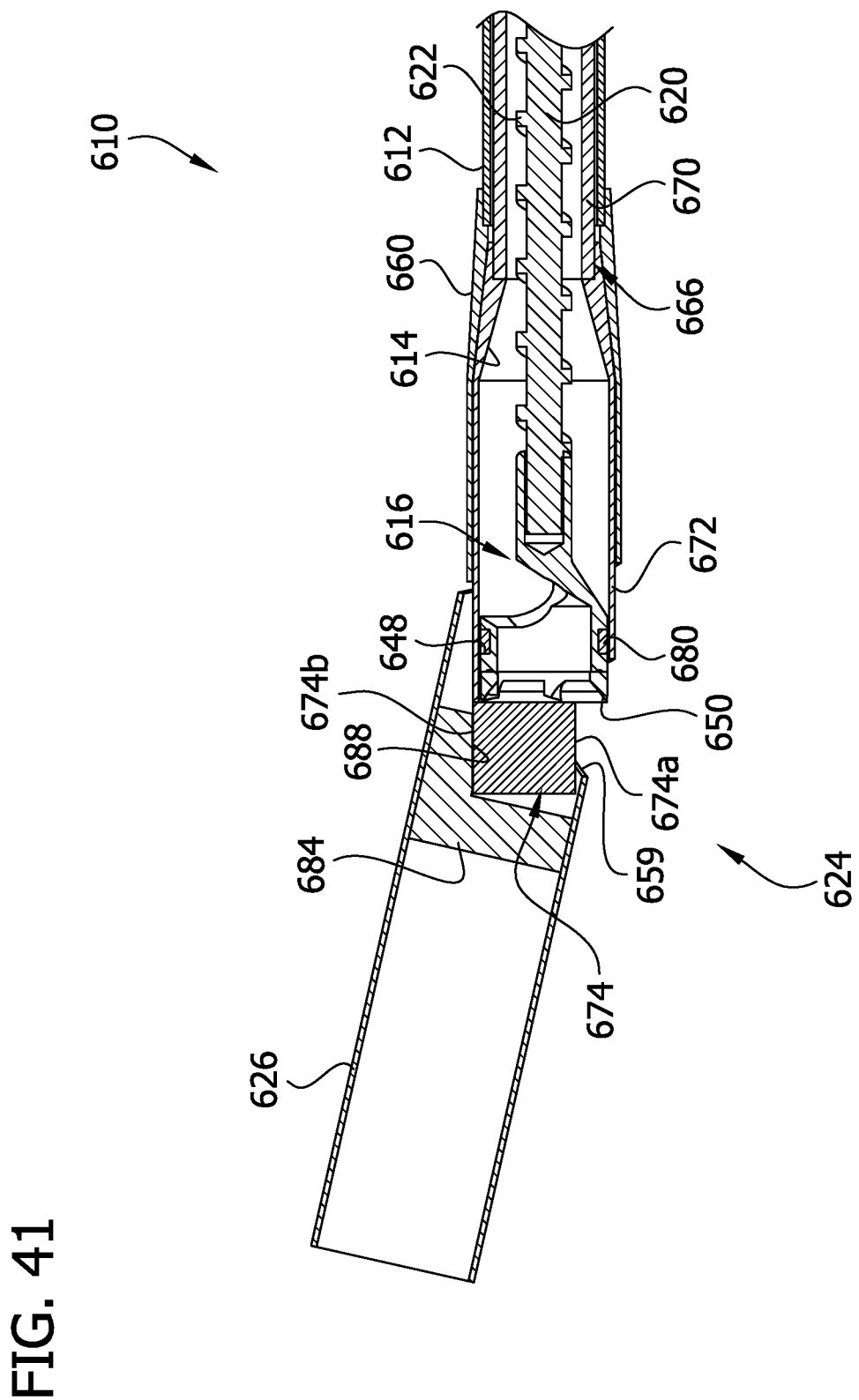
FIG. 41 is a longitudinal section of the catheter of FIG. 40.

Referring to FIGS. 36-41, a sixth embodiment of a tissue-removing catheter is generally indicated at 610. Briefly, the catheter 610 includes an elongate tubular catheter body 612 having opposite proximal and distal ends, a central longitudinal axis $LA_5$ (FIG. 40) extending between the distal and proximal ends, and an internal tissue-transport passage 614 (FIGS. 39 and 41) extending generally along the longitudinal axis of the body. The catheter body 612 may be similar to the catheter body 112 of the first catheter 110, and therefore, corresponding disclosure set forth with respect to catheter body of the first catheter is equally applicable to the present embodiment. Referring to FIGS. 37, 39, and 41, a rotatable cutter, generally indicated at 616, is operatively connected to the distal end of the catheter body 612 for removing tissue from a body lumen, and a driveshaft 620, which includes an external helical thread 622, drives rotation of the cutter 616 and also transports or moves removed tissue proximally within the tissue-transport passage 614 of the catheter body 612. The cutter 616 and the driveshaft 620 may be substantially similar to the cutter 516 and driveshaft 520 of the fifth embodiment, and therefore, corresponding disclosure set forth with respect to catheter body of the fifth catheter is equally applicable to the present embodiment. Moreover, as shown in FIG. 36, the driveshaft 620 is operatively connected to a cutter driver 630 (e.g., a cutter motor) in a handle 632 for imparting rotation of the driveshaft. The handle 632 also includes an actuator 640 (e.g., a lever) for activating the cutter driver 630 and a power source 634 for supplying power to the cutter driver. A deployment mechanism, generally indicated at 624, comprises a cutter housing 626 that is configurable between a closed position (FIGS. 36, 38, and 39), in which the cutter 616 is not exposed for cutting, and an open position (FIGS. 40 and 41), in which the cutter is exposed through a cutting window 659 defined by the cutter housing.

Referring to FIGS. 36-41, a housing adaptor 660 is secured to the distal end of the catheter body 612. For purposes of this disclosure, the housing adaptor 660 is considered part of the catheter body 612. A proximal end portion of the cutter housing 626 is pivotably connected to the housing adaptor 660 by pins 662 (only one pin is visible in FIGS. 36-38 and 40; the other pin is at a location diametrically opposite the visible pin). As explained below, the cutter housing 626 is selectively pivotable about the pins 662 for opening and closing the cutter housing 618.

Referring to FIGS. 37, 39, and 41, a cam shaft, generally indicated at 666, extends through a cam passage 668 extending longitudinally through the catheter body 612, including the housing adaptor 660. The cam shaft 666 includes a tubular torque shaft 670 (e.g., a torque tube), a cutter adaptor 672 fixedly secured to and extending longitudinally outward from a distal end of the torque shaft, and an eccentric 674 fixedly secured to a distal end of the cutter adaptor. The torque shaft 670 is rotatable about its longitudinal axis relative to the catheter body 612. A proximal end of the torque shaft 670 is operatively connected to the handle 632 for imparting rotation of the shaft about its longitudinal axis. In particular, referring to FIG. 36 the handle 632 may include an actuator 676 (e.g., a lever or knob) for imparting rotation to the torque shaft 670. In one example, the actuator 676 is a manual actuator for manually rotating the torque shaft 670. In another example, such as illustrated, the actuator 676 activates a cam motor 678 that is operatively connected to the torque shaft 670 to impart rotation to the torque shaft. The torque shaft 670 may be rotatable in other ways.

Rotation of the torque shaft 670 about its axis imparts rotation of the cutter adaptor 672 about the axis of the torque shaft, relative to the cutter 616 and the catheter body 612. The cutter adaptor 672 includes bearing pins 680 (FIGS. 39 and 41) received in a circumferential groove 648 on the cutter 616 to allow for rotation of the cutter adaptor (and the cam shaft 666) relative to the cutter, and vice versa. The tissue-transport passage 614 is defined by interior surfaces of the cutter adaptor 672 and the torque shaft 668. In the illustrated embodiment, tissue cut by the cutter 616 travels through the cutter 616 and into the tissue-transport passage 614, where the removed tissue is picked up by the rotating driveshaft 620 and transported proximally within the catheter body 612.

Rotation of the torque shaft 670 about its axis also imparts rotation of the eccentric 674 about the axis of the torque shaft 670 relative to the cutter housing 626. The eccentric 674 interacts with a cam follower 684 secured to (e.g., secured within) the cutter housing 626 to drive opening and closing of the cutter housing. Together, the eccentric 674 and the cam follower 684 constitute a cam mechanism. More specifically, when the cutter housing 626 is in the closed position, a generally flat surface 674a (e.g., a longitudinally truncated portion) opposes an engagement surface 688 of the cam follow 684, and an arcuate surface 674b of the eccentric is adjacent the cutter window 659. As the eccentric 674 rotates about the axis of the torque shaft 670, the engagement surface 688 of the cam follower 684 rides along an arcuate surface 674b of the eccentric, whereby the cutter housing 626 pivots or rotates about the hinge pins 662 (e.g., hinge axis $A_{H6}$), away from the cutter 616, and a portion of the cutting edge 650 of the cutter 616 is exposed through the cutter window 659. When the eccentric 674 is rotated about 180 degrees from its position when the cutter housing 626 is closed, the flat surface 674a is adjacent the cutter window, and the cutter housing is fully open, as shown in FIG. 40. In the fully open position, the longitudinal axis $LA_6$ of the cutter housing 626 extends at an offset angle relative to the longitudinal axis $LA_5$ of the catheter body 612. This offset angle may measure from about 15 degrees to about 45 degrees, or from about 20 degrees to about 30 degrees. As shown in FIG. 41, the radial extent of the flat surface 674a is less than that of the cutting edge 650 of the cutter 616, such that the eccentric does not cover the exposed portion of the cutting edge of the cutter when the cutter housing is in the open position. In one embodiment, amount by which the cutting edge 650 is exposed is adjustable by allowing the eccentric 674 to be rotated incrementally to different rotational positions, which would allow for selective adjustment of the offset angle. To close the cutter housing 626, the eccentric 674 is rotated to its initial position when the cutter housing is closed, such that the cutter housing pivots toward the cutter 616 about the pins 662.

An exemplary use of the catheter 610 may be similar to the exemplary use of the first catheter 110 set forth above, with the exception being that the cutter housing 626 is opened and closed by rotating the cam shaft 666, as set forth above.

Figure 42:
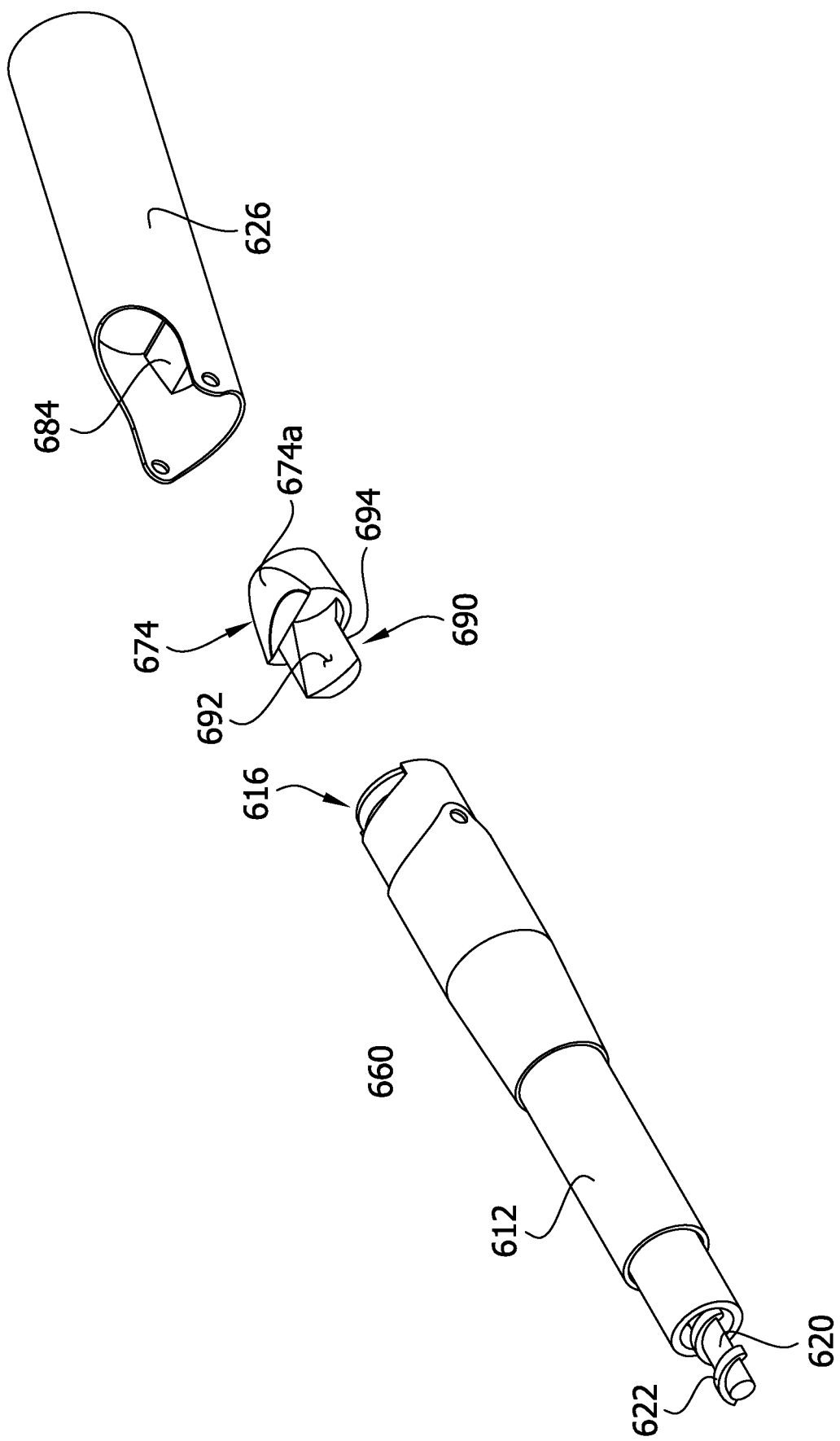
FIG. 42 is an exploded perspective view of the tissue-removing catheter of the sixth embodiment, but further including a tissue director.
Figure 43:
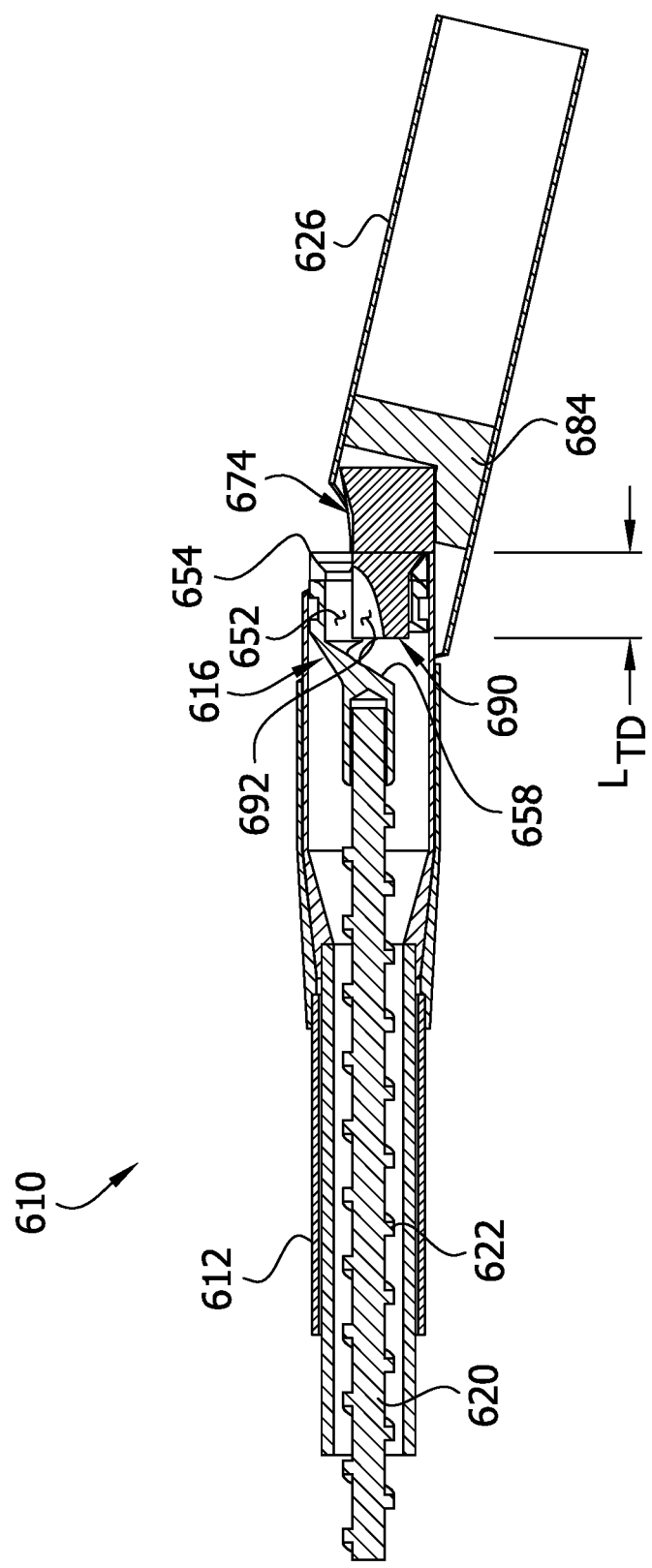
FIG. 43 is an enlarged longitudinal section of the distal end portion of the tissue-removing catheter of FIG. 42, including a cutter housing in an open position.

Referring to FIGS. 42 and 43, in one example the catheter 610 may further include a tissue director, generally indicated at 690, for directing tissue removed by the cutter 616 proximally within the axial cavity 652 of the cutter. The illustrated tissue director 690 is also configured for directing removed tissue circumferentially relative to axial cavity 652 toward the eccentric opening 658 (FIG. 43) to facilitate movement of the removed tissue through the cutter 616 where the removed tissue can be picked up by the helical thread 622. Although the illustrated tissue director 690 is associated with the catheter 610, it is understood that the tissue director may be incorporated in a different catheter having a deflectable distal tip or other deployment mechanism.

Figure 44:
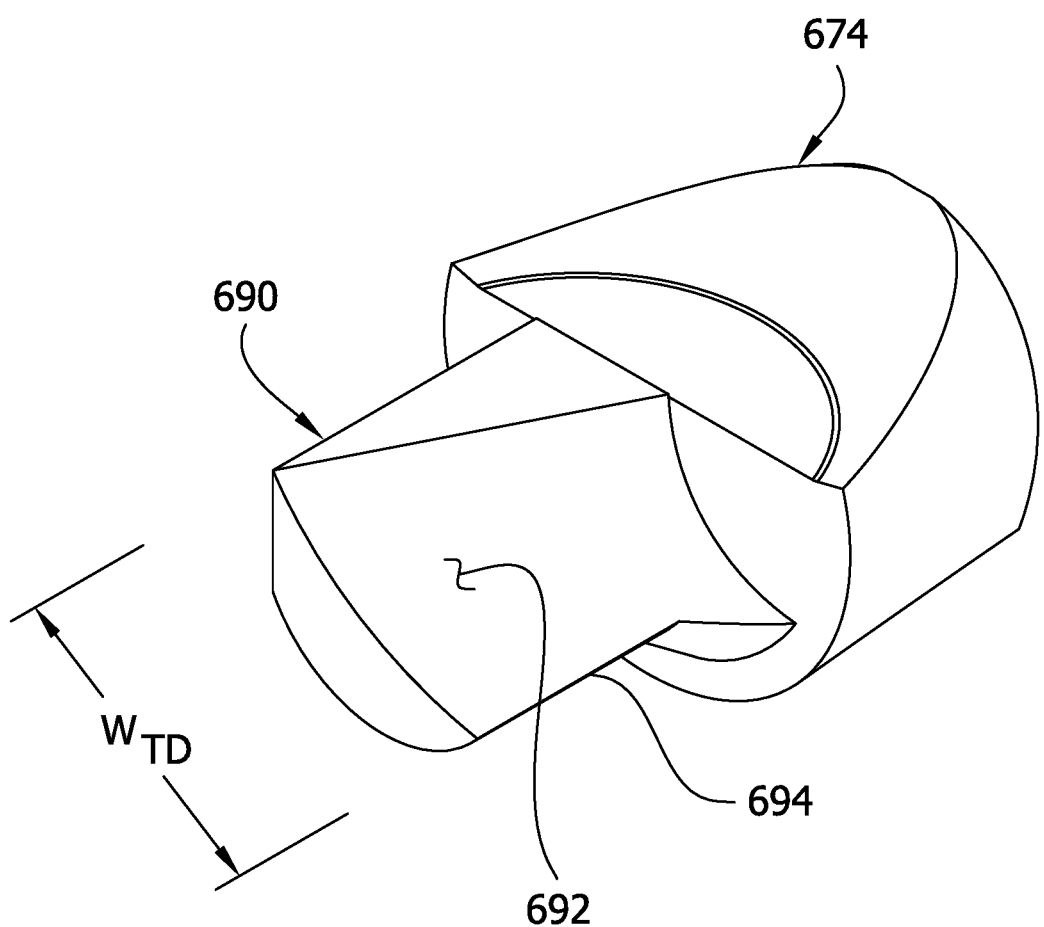
FIG. 44 is an enlarged right perspective of the tissue director.
Figure 45:
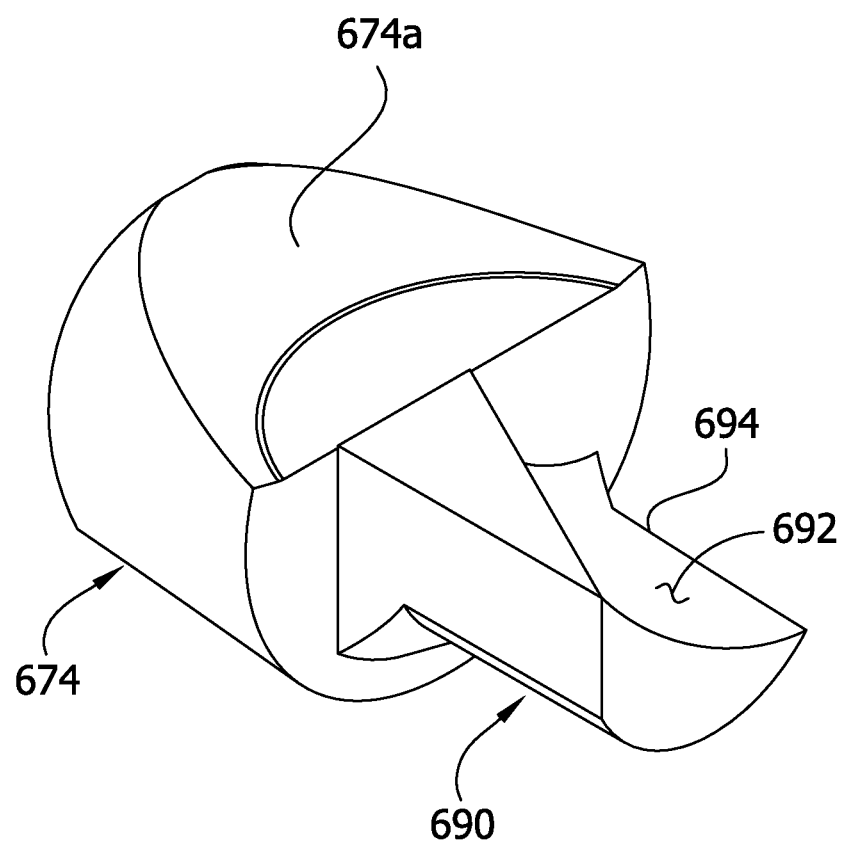
FIG. 45 is an enlarged left side perspective of the tissue director.
Figure 46:
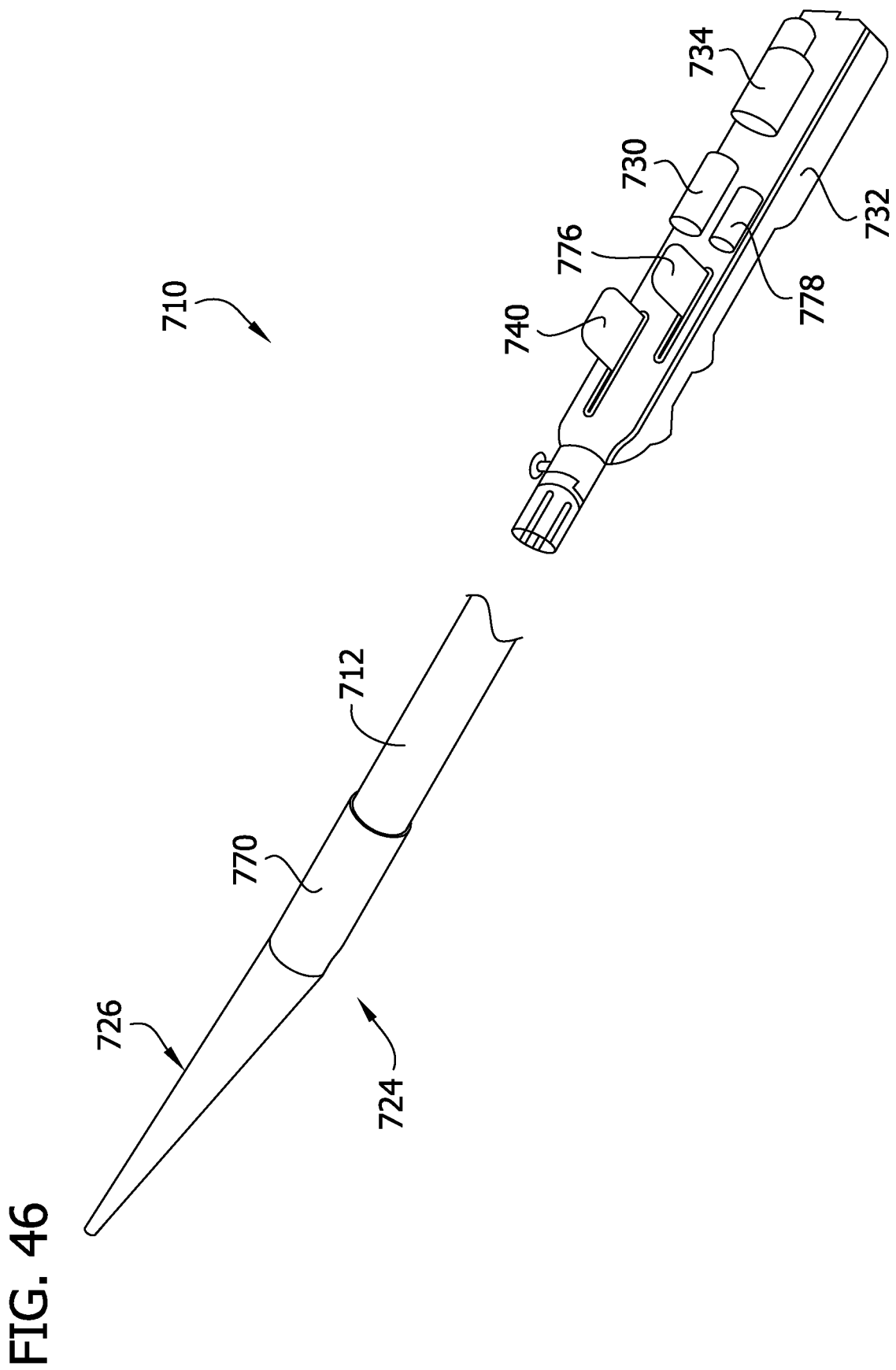
FIG. 46 is a fragmentary perspective of a seventh embodiment of a tissue-removing catheter, including a removable handle attachable to a proximal end of the catheter.

The illustrated tissue director 690 is secured to the eccentric 674 and extends proximally therefrom into the axial cavity 652 of the cutter 616. The tissue director 690 may be formed separately from and attached to the eccentric 674 or formed integrally with the eccentric. The tissue director 690 may be relatively rigid and free from attachment to the cutter 616 so that the cutter is rotatable about the tissue director. The tissue director 690 has a length $L_{TD}$ (FIG. 43) extending generally axially within the axial cavity 652 from adjacent the distal tip 654 of the cutter 616 to adjacent the eccentric opening 658, and a width $W_{TD}$ (FIG. 44) extending generally across the axial cavity (e.g., diametrically across the axial cavity). Referring to FIGS. 44 and 45, the tissue director 690 defines a groove or fluting 692 extending along the length $L_{TD}$ of the tissue director. The fluting 692 extends along a counterclockwise or left-handed helical path as viewed from the distal end of the catheter 610, and in the illustrated embodiment, the direction of the helical path of the fluting (e.g., counterclockwise direction) is the same as the direction that the cutter 616 rotates (e.g., counterclockwise). A leading longitudinal edge 694 of the flute portion gradually falls away from (i.e., slopes radially away from) the rotational axis of the cutter 616 and toward the interior wall defining the axial cavity 652.

As tissue is removed by the rotating cutter 616, the tissue director 690 directs the removed tissue both circumferentially and proximally within the axial cavity 652 to inhibit the removed tissue from passing back through the open distal end 654 of the cutter. It is understood that the tissue director 690 may be incorporated in other catheters other than the illustrated catheter 610.

Figure 47:
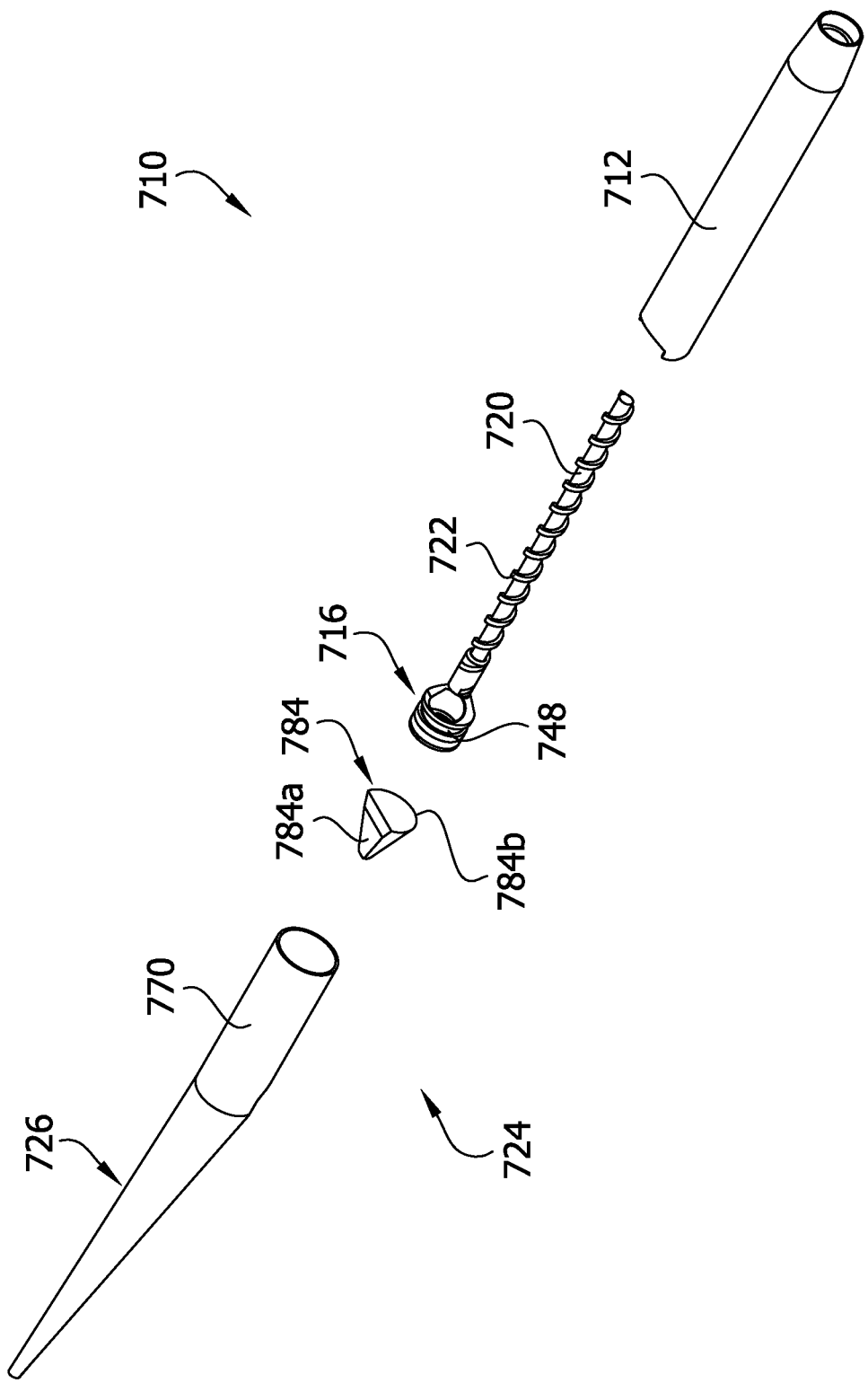
FIG. 47 is an exploded view of a distal end portion the tissue-removing catheter of FIG. 46.
Figure 48:
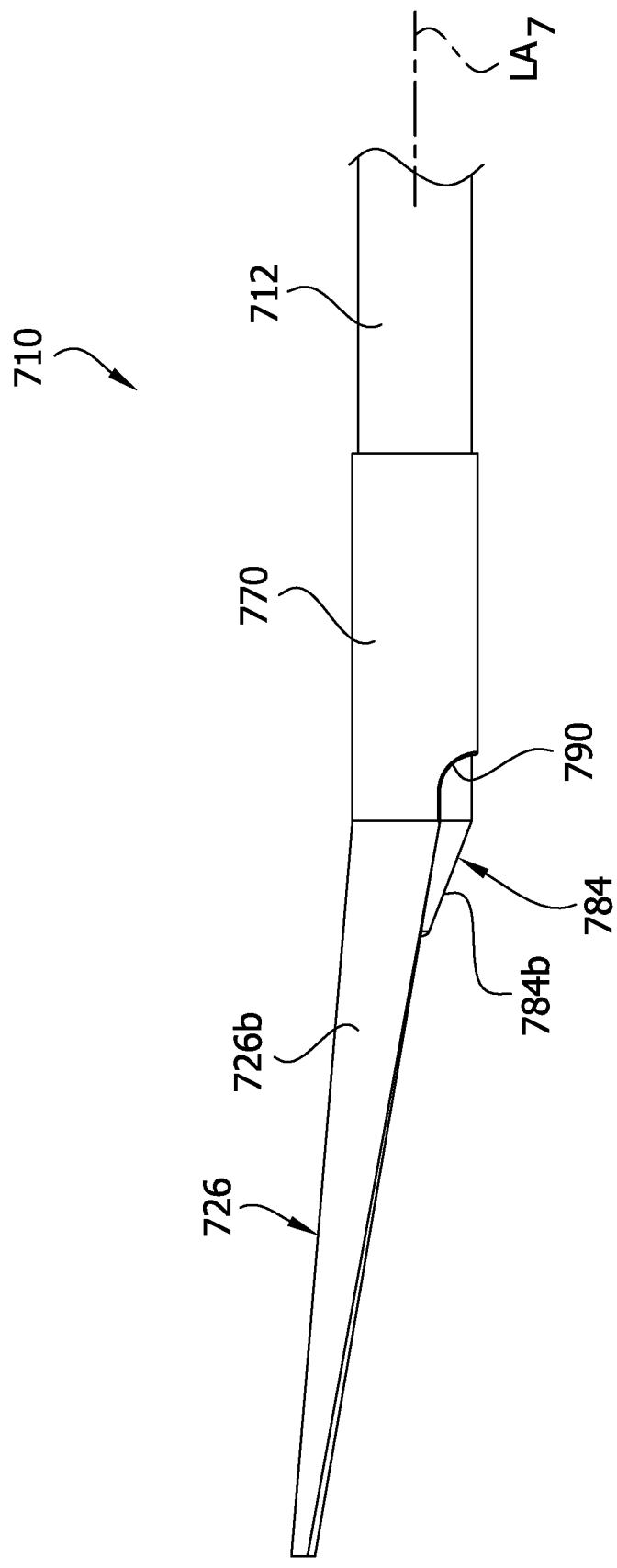
FIG. 48 is an enlarged, side elevational view of a distal end portion of the tissue-removing catheter, the cutter housing being in the closed position.
Figure 49:
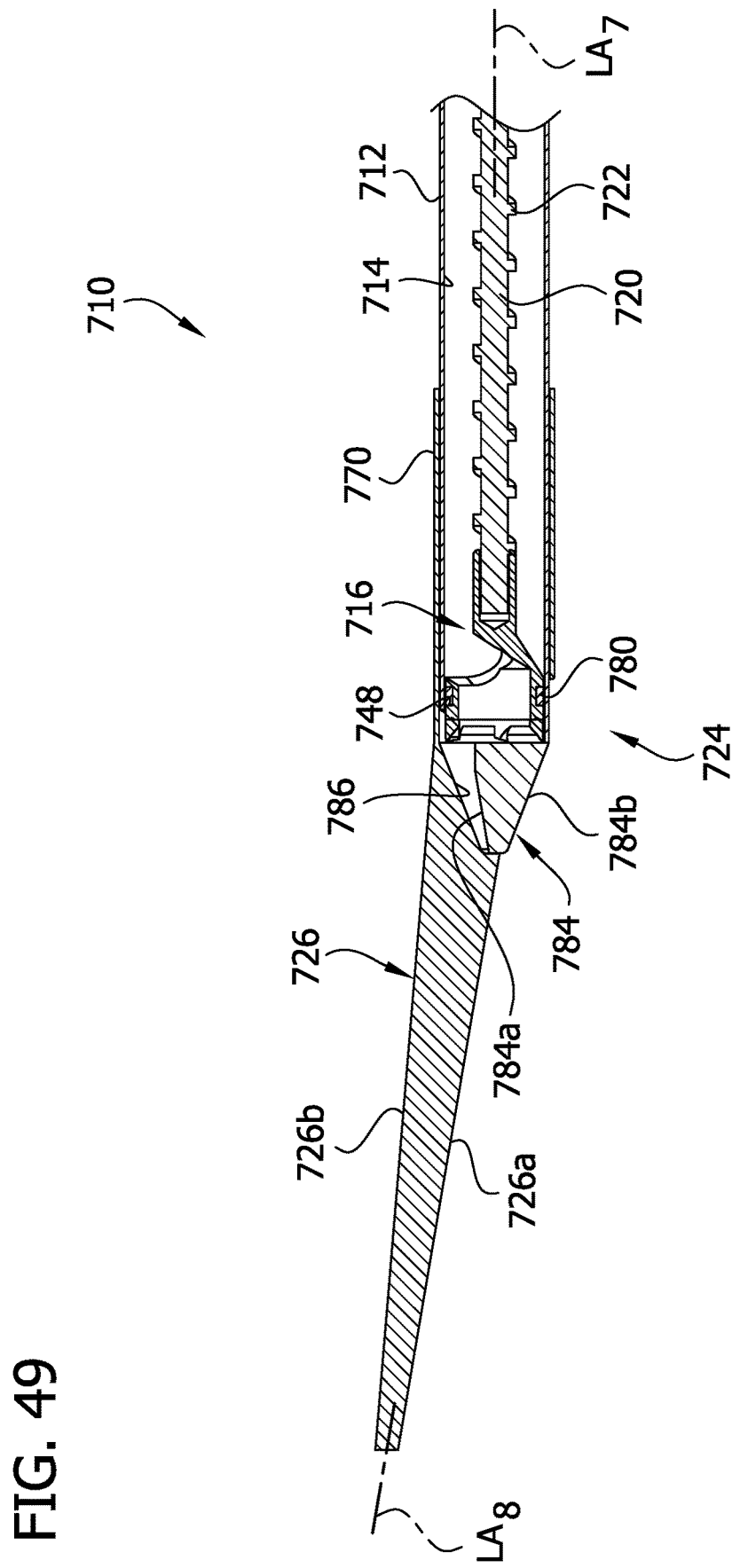
FIG. 49 is a longitudinal section of the catheter of FIG. 48.
Figure 50:
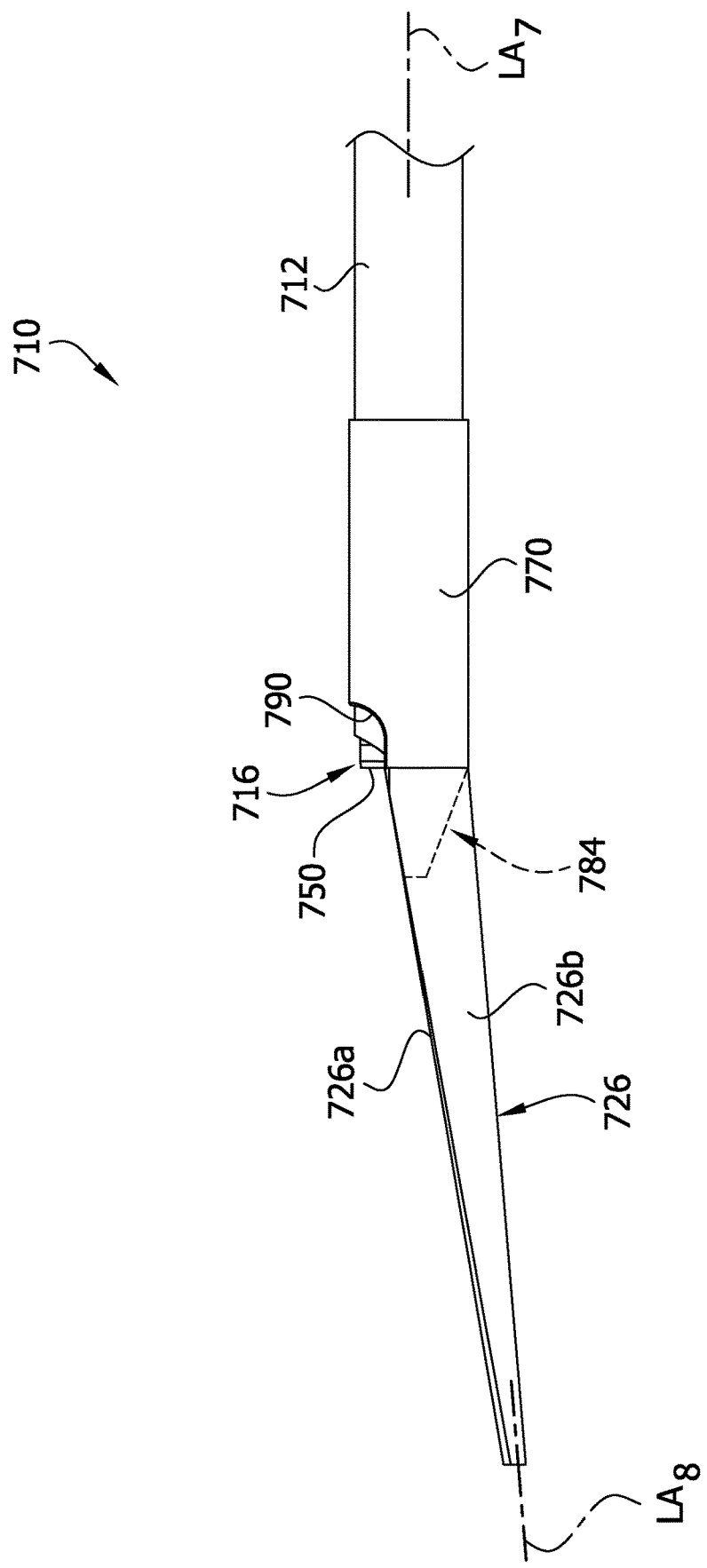
FIG. 50 is similar to FIG. 48, but with the cutter housing in the open position.
Figure 51:
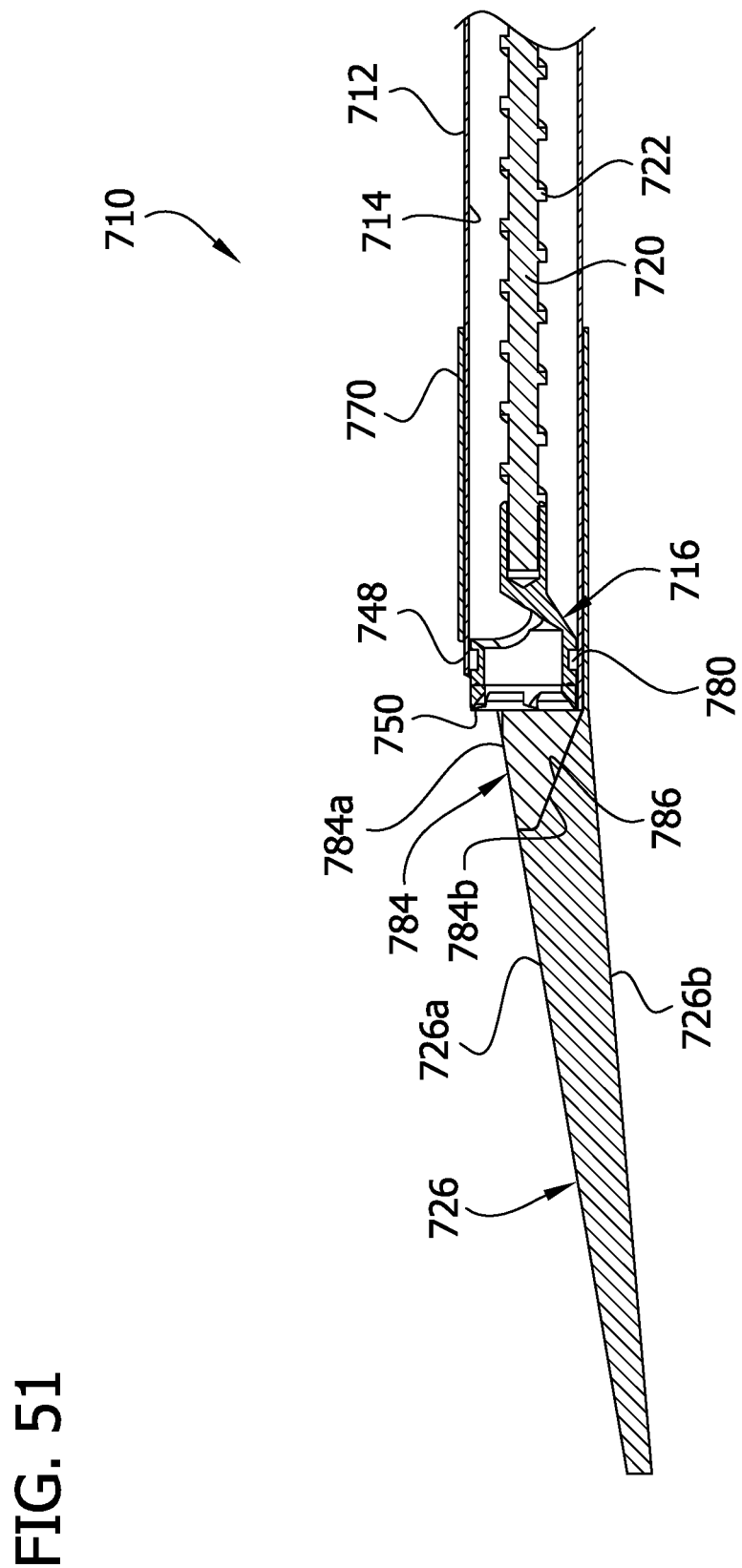
FIG. 51 is a longitudinal section of the catheter of FIG. 50.

Referring to FIGS. 46-53, a seventh embodiment of a tissue-removing catheter is generally indicated at 710. Briefly, the catheter 710 includes an elongate tubular catheter body 712 having opposite proximal and distal ends, a central longitudinal axis $LA_7$ (FIG. 48) extending between the distal and proximal ends, and an internal tissue-transport passage 714 (FIGS. 49 and 51) extending generally along the longitudinal axis of the body. The catheter body 712 may be similar to the catheter body 112 of the first catheter 110, and therefore, corresponding disclosure set forth with respect to catheter body of the first catheter is equally applicable to the present embodiment. Referring to FIGS. 47, 49, and 51, a rotatable cutter, generally indicated at 716, is operatively connected to the distal end of the catheter body 712 for removing tissue from a body lumen (e.g., a blood vessel), and a driveshaft 720, which includes an external helical thread 722, drives rotation of the cutter 716 and also transports or moves removed tissue proximally within the tissue-transport passage 714 of the catheter body 712. The cutter 716 and the driveshaft 720 may be substantially similar to the cutter 516 and driveshaft 520 of the fifth embodiment, and therefore, corresponding disclosure set forth with respect to catheter body of the fifth catheter is equally applicable to the present embodiment. Moreover, the driveshaft 720 is operatively connected to a cutter driver 730 (e.g., a cutter motor) in a handle 732 for imparting rotation of the driveshaft. The handle 732 also includes an actuator 740 (e.g., a lever) for activating the cutter driver 730 and a power source 734 for supplying power to the cutter driver. A deployment mechanism, generally indicated at 724, comprises a cutter housing 726 that is configurable between a closed position (FIGS. 46, 48, and 49), in which the cutter 716 is not exposed for cutting, and an open position (FIGS. 35 and 36), in which the cutter is exposed.

Referring to FIGS. 49 and 51, the catheter body 712 includes bearing pins 780 received in a circumferential groove 748 on the cutter 716 to allow for rotation of the cutter relative to the catheter body. The tissue-transport passage 714 is defined by interior surface of the catheter body 712. In the illustrated embodiment, tissue cut by the cutter 716 travels through the cutter 716 and into the tissue-transport passage 714, where the removed tissue is picked up by the rotating driveshaft 720 and transported proximally within the catheter body 712. For reasons explained below, a cone-shaped guard, generally indicated at 784, is fixedly secured to the distal end of the catheter body 712, immediately distal the cutter 716. The guard 784 is truncated longitudinally, whereby a truncated or flat longitudinal portion 784a of the guard has a radial extent, relative to the longitudinal axis $LA_7$ of the catheter body 712, that is less than the radial extent of the cutting edge 750 of the cutter 716. As such, the truncated longitudinal portion 786a does not cover a portion of the cutting edge 750 of the cutter 716.

A torque-transmitting member 770 (e.g., a torque tube) is coaxially received around the catheter body 712 and has a distal end that is fixedly secured to a proximal end of the cutter housing 726. Although not illustrated as such in the drawings, a proximal end of the torque-transmitting member 770 is operatively connected to the handle 732 for selectively imparting rotation of the torque-transmitting member about its axis relative to the catheter body 712. In particular, referring to FIG. 46 the handle 732 may include an actuator 776 (e.g., a lever or knob) for imparting rotation to the torque-transmitting member 770. In one example, the actuator 776 is a manual actuator for manually rotating the torque-transmitting member 770. In another example, such as illustrated, the actuator 776 activates a torque motor 778 that is operatively connected to the torque-transmitting member 770 to impart rotation to the torque tube. The torque-transmitting member 770 may be rotatable in other ways.

Figure 53:
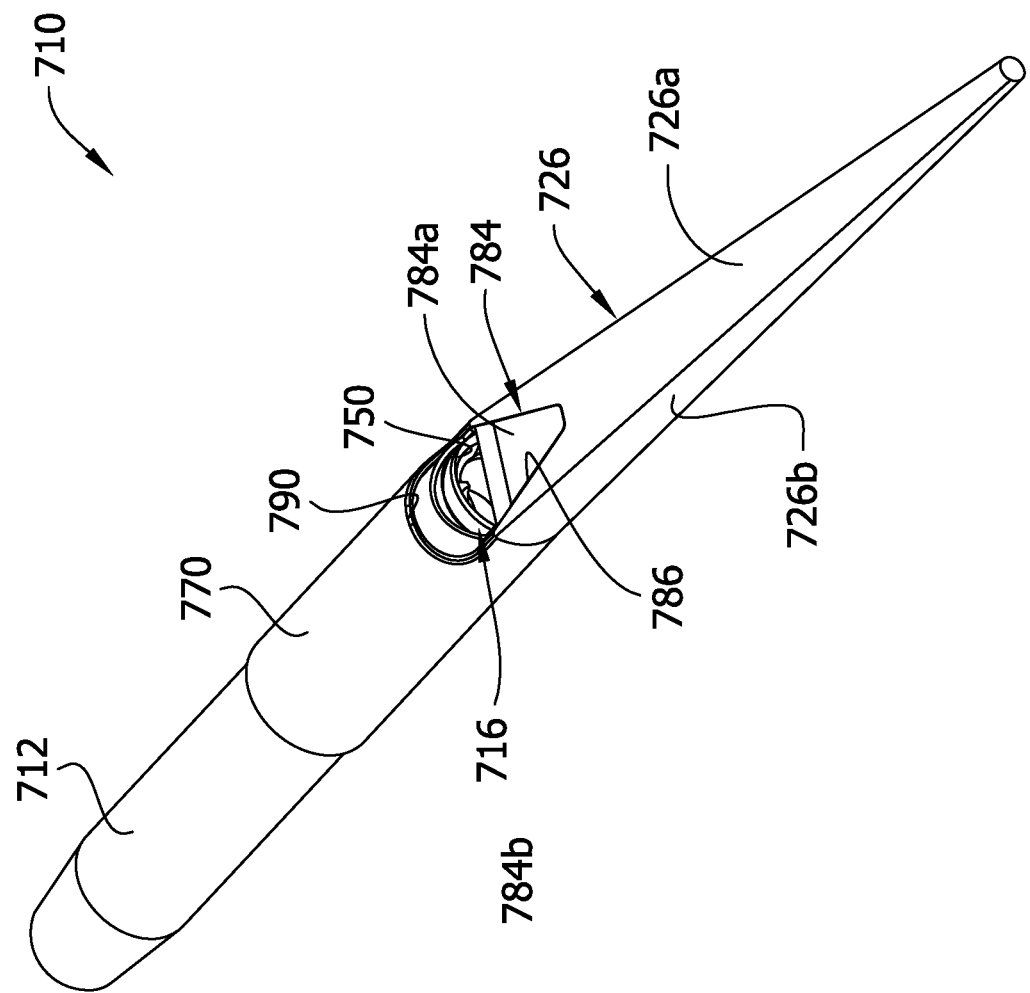
FIG. 53 is similar to FIG. 52, with the cutter housing in the open position.
Figure 54:
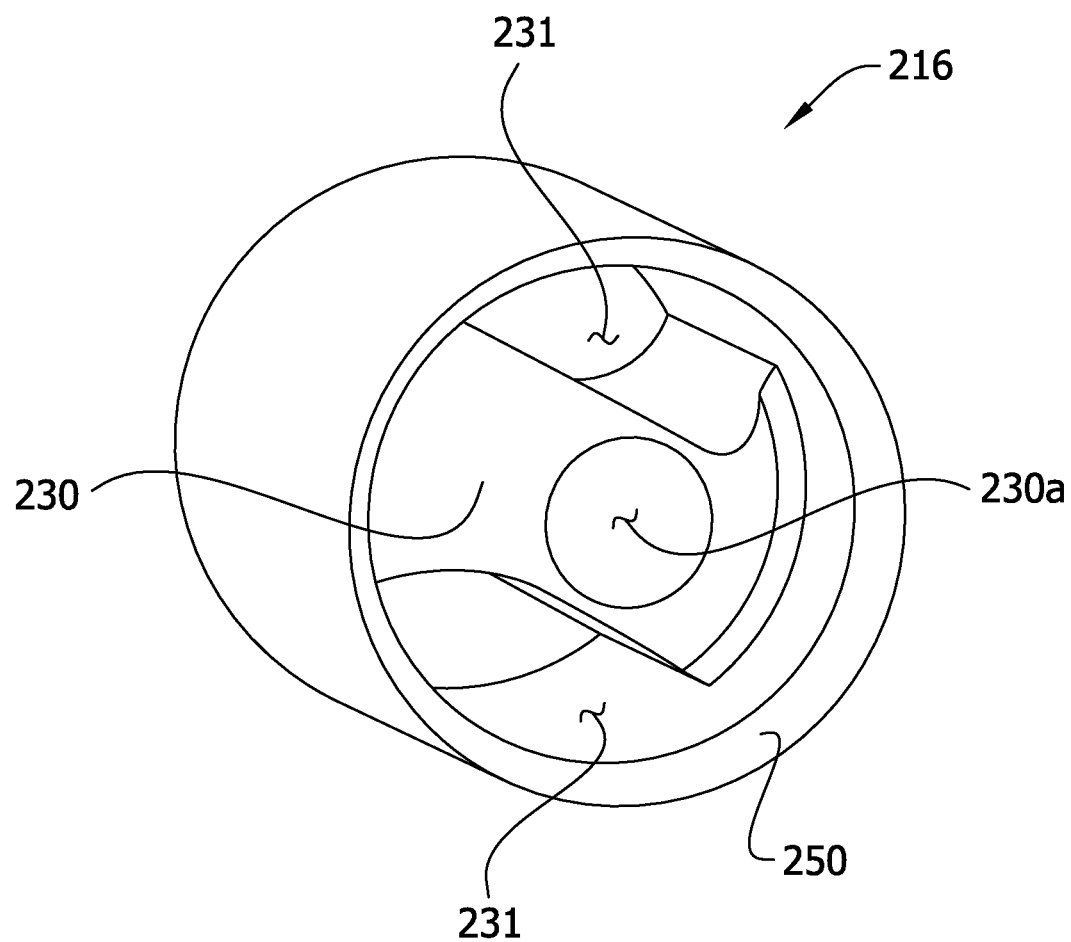
FIG. 54 is an enlarged perspective of a cutter of the tissue-removing catheter of FIGS. 1-13.
Figure 55:
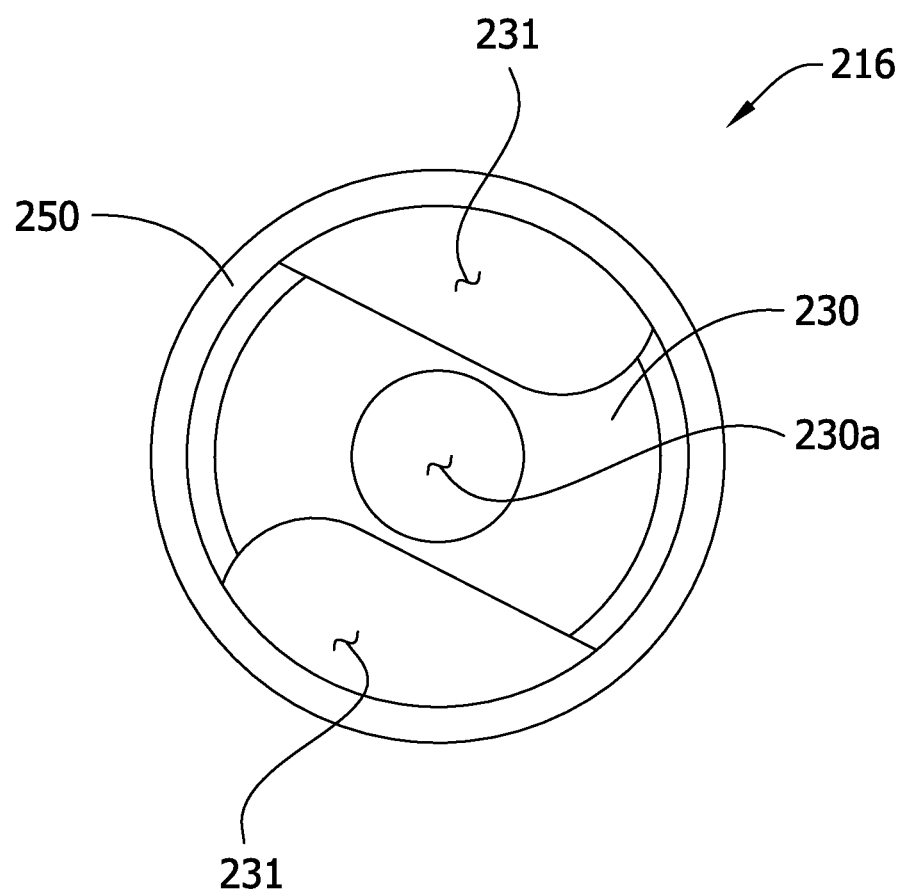
FIG. 55 is a front elevational view of the cutter of FIG. 54.

The cutter housing 726 has a longitudinal axis $LA_8$ (FIGS. 49 and 50) extending at an offset angle relative to the longitudinal axis of the catheter body 712. The cutter housing 726 has a generally cone shape, including a longitudinal flat or truncated portion 726a and an arcuate portion 726b. A radial extent of the truncated portion 726a is less than the radial extent of the cutting edge 750 of the cutter 716, with respect to the longitudinal axis $LA_7$ of the catheter body 712 so that a portion of the cutting edge adjacent to the truncated portion is not covered by the cutter housing 726. A clearance opening 786 extends generally longitudinally through a proximal end of the cutter housing 726 and radially through the truncated portion 726a. As shown in FIGS. 50, 51 and 53, the cone-shaped guard 784 is receivable in the clearance opening 786 when the cutter housing 726 is rotated to its open position. The size and shape of the clearance opening 786 are generally complementary to the cone-shaped guard 784. A clearance opening 790 (FIGS. 50 and 53) for the cutting edge 750 of the cutter 716 extends longitudinally through the distal end of the torque-transmitting member 770.

Figure 52:
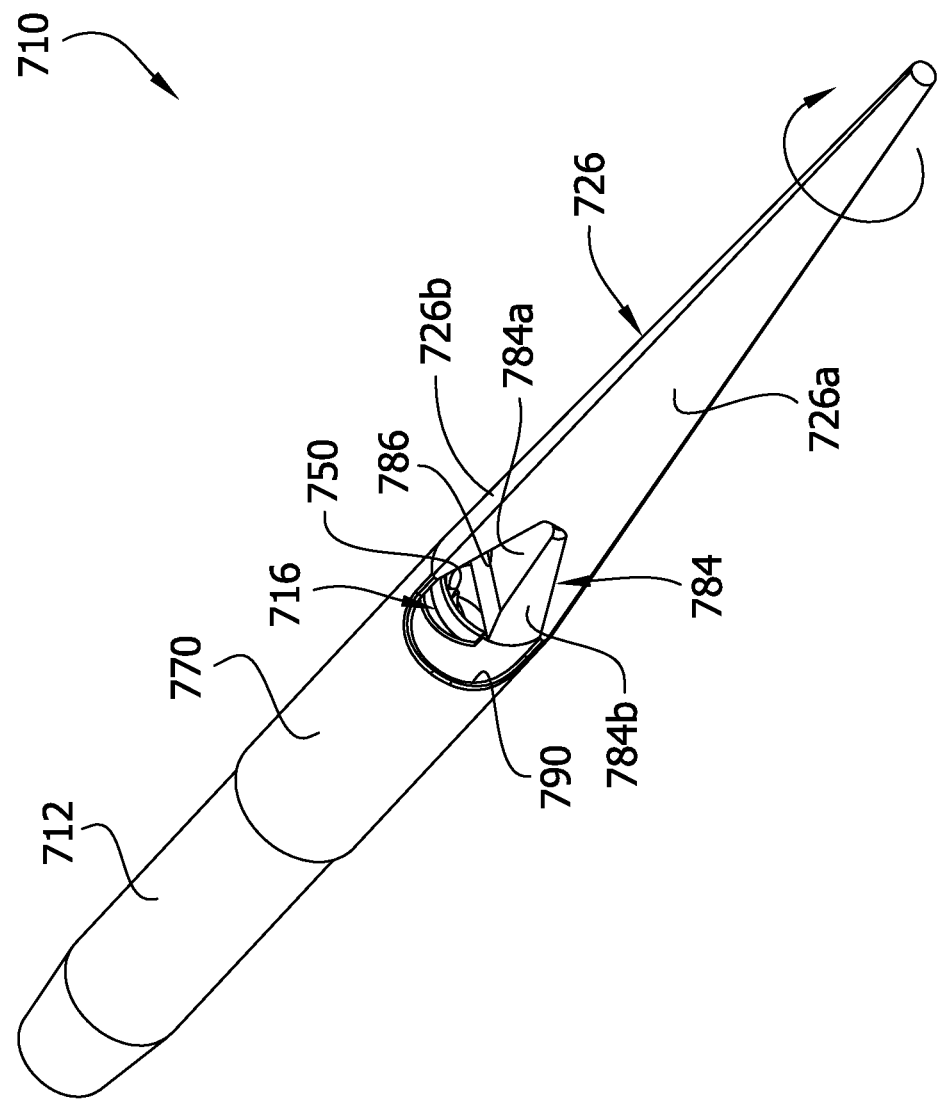
FIG. 52 is a front perspective of the catheter of FIG. 50, with the cutter housing being rotated from the closed position to the open position.

As shown in FIGS. 48 and 49, when the cutter housing 726 is in its closed position, the cutter guard 784 covers a portion of the cutting edge 750 of the cutter 716, as set forth above, and the cutter housing 726 covers the remainder of the cutting edge that is not covered by the cutter guard. To open the cutter housing 726 and expose a portion of the cutting edge 750, the cutter housing 726 is rotated by the torque-transmitting member 770 about the axis of the torque-transmitting member (which is generally coaxial with the longitudinal axis $LA_7$ of the catheter body 712), such as by using the actuator 776. Referring to FIG. 52, as the cutter housing 726 rotates (in the direction indicated in FIG. 52), the cutter guard 784 enters the clearance opening 786 (i.e., the cutter housing rotates about the cutter guard). The cutter housing 726 is in its open position when the truncated portion of the cutter housing is generally flush (e.g., coplanar) with the truncated portion of the cutter guard (FIGS. 51 and 53). In this position, a portion of the cutting edge 250 of the cutter 216 is exposed.

An exemplary use of the catheter 710 may be similar to the exemplary use of the first catheter 110 set forth above, with the exception being that the cutter housing 726 is opened and closed by rotating the torque-transmitting member 770, as set forth above.

Having described embodiments of the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter comprising:
    an elongate catheter body configured for insertion into a body lumen of a subject, the catheter body having opposite distal and proximal ends, a longitudinal axis extending between the distal and proximal ends;

a cutter located generally at the distal end of the catheter body adapted to remove tissue from the body lumen, the cutter having a proximal end portion, a distal end portion, and a longitudinal axis extending between the proximal and distal end portions;

a cutter housing adjacent the distal end of the catheter body, the cutter housing including a distal longitudinal portion located distal of the cutter, wherein the distal longitudinal portion is pivotable generally about a hinge axis, relative to the cutter between a closed position, in which the cutter is covered by the cutter housing, and an open position, in which at least a portion of the cutter is exposed;

a force-transmitting member extending along the catheter body and being longitudinally movable relative to the catheter body, wherein a distal end portion of the force-transmitting member is operatively connected to the distal longitudinal portion of the cutter housing such that distal movement of the force-transmitting member relative to the catheter body and the cutter imparts pivoting of the distal longitudinal portion of the cutter housing to its open position to expose the cutter; and a track located adjacent the distal end of the catheter body, the track defining a slot having an offset portion extending at an offset angle relative to the longitudinal axis of the catheter body, wherein the cutter housing is configured to track along the offset portion of the slot when the force-transmitting member is moved distally relative to the catheter body;

wherein the slot has a shape and the shape of the slot is the same when the cutter housing is in the open position and the closed position.

2. The tissue-removing catheter set forth in claim 1, wherein the cutter housing is pivotably secured to the force-transmitting member.

3. The tissue-removing catheter set forth in claim 2, wherein the force-transmitting member includes a sleeve slidably received over the catheter body, and a pair of slide arms extending longitudinally outward from a distal end of the sleeve, wherein the cutter housing is pivotably secured to the slide arms.

4. The tissue-removing catheter set forth in claim 3, wherein each of the slide arms includes a pivot pin received in a respective one of a pin opening defined the cutter housing.

5. The tissue-removing catheter set forth in claim 4, wherein the hinge axis extends through the pivot pins.

6. The tissue-removing catheter set forth in claim 3, wherein the slot comprises a pair of slots having respective offset portions, each slot further having a longitudinal portion in registration with an offset portion of said respective offset portions, wherein the pair of slide arms are slidably received in respective longitudinal portions of the slots.

7. The tissue-removing catheter set forth in claim 6, wherein the cutter housing includes housing pins received in respective slots, wherein the housing pins are configured to slidably translate in the respective offset portions of the slots.

8. The tissue-removing catheter set forth in claim 7, wherein the housing pins are configured to slidably translate in the respective longitudinal portions of the slots.

9. The tissue-removing catheter set forth in claim 1, wherein the track comprises a pair of tracks secured adjacent to and extending longitudinally outward from the distal end of the catheter body.

10. The tissue-removing catheter set forth in claim 9, wherein the tracks are diametrically opposite one another on the catheter body.

11. The tissue-removing catheter set forth in claim 1, wherein a longitudinal axis of the cutter housing extends at an offset angle relative to the longitudinal axis of the catheter body when the distal longitudinal portion of the cutter housing is pivoted about the hinge axis to its open position.

12. The tissue-removing catheter set forth in claim 11, wherein the offset angle measures from about 15 degrees to about 45 degrees.

13. The tissue-removing catheter set forth in claim 11, wherein the offset angle measures from about 20 degrees to about 30 degrees.

14. The tissue-removing catheter set forth in claim 1, wherein the cutter is rotatable relative to the catheter body about the longitudinal axis of the cutter.

15. The tissue-removing catheter set forth in claim 14, further comprising a cutter driveshaft operatively connected to the cutter for imparting rotation of the cutter about the longitudinal axis of the cutter.

16. The tissue-removing catheter set forth in claim 1, further comprising:
a handle coupled to the proximal end of the catheter body; and
an actuator coupled to the handle, wherein the actuator is operatively connected to the force-transmitting member and configured to impart longitudinal movement of the force-transmitting member relative to the catheter body.

17. The tissue-removing catheter set forth in claim 1, wherein the force-transmitting member comprises a sleeve received above the catheter body.

18. A method of removing tissue from a body lumen, the method comprising:
inserting a tissue-removing catheter into the body lumen, the tissue-removing catheter comprising
an elongate catheter body configured for insertion into the body lumen, the catheter body having opposite distal and proximal ends, a longitudinal axis extending between the distal and proximal ends,
a cutter located generally at the distal end of the catheter body adapted to remove tissue from the body lumen, the cutter having a proximal end portion, a distal end portion, and a longitudinal axis extending between the proximal and distal end portions,
a cutter housing adjacent the distal end of the catheter body, the cutter housing including a distal longitudinal portion located distal of the cutter, wherein the distal longitudinal portion is pivotable generally about a hinge axis, relative to the cutter between a closed position, in which the cutter is covered by the cutter housing, and an open position, in which at least a portion of the cutter is exposed,
a force-transmitting member extending along the catheter body and being longitudinally movable relative to the catheter body, wherein a distal end portion of the force-transmitting member is operatively connected to the distal longitudinal portion of the cutter housing such that distal movement of the force-transmitting member relative to the catheter body and the cutter imparts pivoting of the distal longitudinal portion of the cutter housing to its open position to expose the cutter, and a track located adjacent the distal end of the catheter body, the track defining a slot having an offset portion extending at an offset angle relative to the longitudinal axis of the catheter body, wherein the cutter housing is configured to track along the offset portion of the slot when the force-transmitting member is moved distally relative to the catheter body;

wherein the slot has a shape and the shape of the slot is the same when the cutter housing is in the open position and the closed position;

moving, after said inserting a tissue-removing catheter into the body lumen, the force-transmitting member distally relative to the catheter body and the cutter to impart pivoting of the distal longitudinal portion of the cutter housing to its open position to expose the cutter; and removing, after said moving the force-transmitting member, tissue from the body lumen using the cutter.

19. The method of removing tissue from a body lumen set forth in claim 18, wherein said removing tissue from the body lumen using the cutter comprises rotating the cutter relative to the catheter body.

20. The method of removing tissue from a body lumen set forth in claim 18, further comprising moving, after said removing tissue from the body lumen using the cutter, the force-transmitting member proximally relative to the catheter body and the cutter to impart pivoting of the distal longitudinal portion of the cutter housing to its closed position to cover the cutter.

\* \* \* \* \*